United States Patent
Galka et al.

(10) Patent No.: US 10,227,310 B2
(45) Date of Patent: *Mar. 12, 2019

(54) GHRELIN 0-ACYL TRANSFERASE INHIBITORS

(71) Applicant: Eli Lilly and Company, Indianapolis, IN (US)

(72) Inventors: Christopher Stanley Galka, Carmel, IN (US); Erik James Hembre, Indianapolis, IN (US); Nicholas Allan Honigschmidt, Lakeville, MN (US); Maria Angeles Martinez-Grau, Madrid (ES); Gema Ruano Plaza, Madrid (ES); Almudena Rubio, Carmel, IN (US); Stacy Jo Keding, Brownsburg, IN (US); Daryl Lynn Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/561,163

(22) PCT Filed: Apr. 13, 2016

(86) PCT No.: PCT/US2016/027180
§ 371 (c)(1),
(2) Date: Sep. 25, 2017

(87) PCT Pub. No.: WO2016/168225
PCT Pub. Date: Oct. 20, 2016

(65) Prior Publication Data
US 2018/0079729 A1    Mar. 22, 2018

(30) Foreign Application Priority Data
Apr. 15, 2015   (EP) .................................... 15382182

(51) Int. Cl.
C07D 401/06      (2006.01)
C07D 239/42      (2006.01)
C07D 401/12      (2006.01)
C07D 417/14      (2006.01)

(52) U.S. Cl.
CPC ......... *C07D 239/42* (2013.01); *C07D 401/06* (2013.01); *C07D 401/12* (2013.01); *C07D 417/14* (2013.01)

(58) Field of Classification Search
CPC .................................................. C07D 401/06
See application file for complete search history.

(56) References Cited

U.S. PATENT DOCUMENTS

2005/0070712 A1    3/2005   Kosogof et al.

FOREIGN PATENT DOCUMENTS

WO      2013/125732 A1    8/2013
WO      2015/073281 A1    5/2015

*Primary Examiner* — Bruck Kifle
(74) *Attorney, Agent, or Firm* — Macharri Vorndran-Jones

(57) ABSTRACT

The present invention provides novel GOAT inhibitors and their salts and pharmaceutical compositions thereof.

20 Claims, No Drawings

GHRELIN 0-ACYL TRANSFERASE INHIBITORS

The present invention relates to compounds useful for inhibiting ghrelin O-acyl transferase (GOAT), pharmaceutical compositions and methods for treating diseases related to GOAT activity.

GOAT belongs to the membrane-bound O-acyl transferase (MBOAT) family of enzymes. It converts desacyl-ghrelin (also known as unacylated ghrelin or UAG) to a biologically active form, acyl-ghrelin (AG), by transferring a fatty acid to the Ser3 residue of the desacylghrelin peptide. Acyl-ghrelin has been shown to increase food intake and increase adiposity in humans and in rodents. Infusion of AG in humans has also been shown to suppress glucose-induced insulin secretion. Elimination of the ghrelin gene has been shown to enhance insulin release to prevent or ameliorate glucose intolerance in high-fat diet fed ob/ob mice.

Small molecule GOAT inhibitors have been reported in the literature. See WO 2013/125732.

However, the prevalence of obesity and diabetes coupled with the variable effectiveness and responses to current treatments for obesity and diabetes necessitate that more treatment choices be available to patients. The present invention provides certain novel compounds that are GOAT inhibitors. Such new compounds could address the need for potent, effective treatment of obesity. It is further believed that a GOAT inhibitor may also be useful in reducing weight gain or weight regain as an adjunct to diet and/or exercise, other therapeutic medicinal agents or procedures designed to reducing weight gain or treat obesity. Similarly, a GOAT inhibitor may be useful in treating type 2 diabetes, singly or in combination with other treatments for type 2 diabetes.

The present invention provides a compound of formula

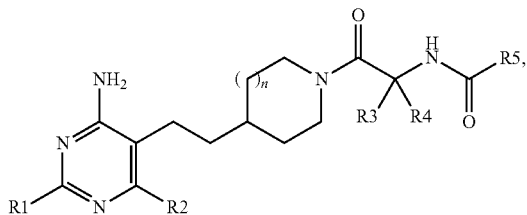

wherein
n is 1 or 2;
$R^1$ and $R^2$ are selected from —$CH_3$ and —Cl, so long as $R^1$ and $R^2$ are not both —$CH_3$ or both —Cl;
$R^3$ and $R^4$ are selected from —H and —$CH_3$, so long as $R^3$ and $R^4$ are not both —$CH_3$;
$R^5$ is selected from —$C_1$-$C_3$ alkyl optionally substituted with —OH or —$CF_3$; —$OC_1$-$C_4$ alkyl; $C_3$-$C_6$ cycloalkyl; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, pyrimidinyl, or pyrazinyl; and phenyl optionally substituted with —$OCH_3$;
provided that when n is 1, $R^1$ is —$CH_3$, $R^2$ is —Cl, $R^3$ is —$CH_3$, and $R^4$ is —H, then $R^5$ cannot be cyclopropyl or a pharmaceutically acceptable salt thereof.

The present invention provides a pharmaceutical composition comprising a compound of the invention, or a pharmaceutically acceptable salt thereof, with one or more pharmaceutically acceptable carriers, diluents, or excipients.

In a further embodiment, the composition is used in combination with one or more other therapeutic agents.

A further aspect of the present invention provides a method of reducing weight gain or weight regain or treating type 2 diabetes or obesity comprising administering a compound of the present invention, or a pharmaceutically acceptable salt thereof, to a patient in need thereof.

The present invention also provides a compound of the invention, or a pharmaceutically acceptable salt thereof, for use in therapy, in particular for reducing weight gain or weight regain or treating type 2 diabetes or obesity. Even further, the present invention provides a compound of the invention, or a pharmaceutically acceptable salt thereof, for use in reducing weight gain or weight regain or treating type 2 diabetes or obesity. Furthermore, the present invention provides the use of a compound of the invention, or a pharmaceutically acceptable salt thereof, in the manufacture of a medicament for reducing weight gain or weight regain or treating type 2 diabetes or obesity.

The present invention further provides a method of treating the sequelae of an ischemic event comprising administering a compound of the present invention, or a pharmaceutically acceptable salt thereof, to a patient in need thereof. In a further embodiment, the ischemic event is myocardial ischemia or cardiac ischemia or cerebral ischemia.

In yet another aspect, the present invention provides a compound of the invention, or a pharmaceutically acceptable salt thereof, for use in therapy, in particular for treating the sequelae of an ischemic event. Even further, the present invention provides a compound of the invention, or a pharmaceutically acceptable salt thereof, for use in treating the sequelae of an ischemic event. Furthermore, the present invention provides the use of a compound of the invention, or a pharmaceutically acceptable salt thereof, in the manufacture of a medicament for treating the sequelae of an ischemic event. In a further embodiment, the ischemic event is myocardial ischemia or cardiac ischemia or cerebral ischemia.

The present invention further provides a method of treating addiction disorders comprising administering a compound of the present invention, or a pharmaceutically acceptable salt thereof, to a patient in need thereof. In a further embodiment, the addiction disorder involves consummatory behaviors, such as alcohol intake, smoking, overeating, or use of illicit drugs.

The present invention provides a method to ameliorate the consequences of stress that promote addictive behaviors comprising administering a compound of the present invention, or a pharmaceutically acceptable salt thereof, to a patient in need thereof. In a further embodiment, the addictive behaviors involve consummatory behaviors, such as alcohol, smoking, overeating, or use of illicit drugs.

The present invention also provides a compound of the invention, or a pharmaceutically acceptable salt thereof, for use in therapy, in particular for treating addiction disorders. Even further, the present invention provides a compound of the invention, or a pharmaceutically acceptable salt thereof, for use in treating addiction disorders. Furthermore, the present invention provides the use of a compound of the invention, or a pharmaceutically acceptable salt thereof, in the manufacture of a medicament for treating addiction disorders. In a further embodiment, the addiction disorder involves consummatory behaviors, such as alcohol, smoking, overeating, or use of illicit drugs.

The present invention also provides a compound of the invention, or a pharmaceutically acceptable salt thereof, for use in therapy, in particular for ameliorating the consequences of stress that promote addictive behaviors. In a further embodiment, the addiction disorder involves consummatory behaviors, such as alcohol, smoking, overeating, or use of illicit drugs. Even further, the present invention provides a compound of the invention, or a pharmaceutically acceptable salt thereof, for use in ameliorating the consequences of stress that promote addictive behaviors. Furthermore, the present invention provides the use of a compound of the invention, or a pharmaceutically acceptable salt thereof, in the manufacture of a medicament for ameliorating the consequences of stress that promote addictive behaviors. In a further embodiment, the addictive behaviors involve consummatory behaviors, such as alcohol, smoking, overeating, or use of illicit drugs.

The present invention also encompasses intermediates and processes useful for the synthesis of a compound of the present invention.

The term "treating" (or "treat" or "treatment") as used herein refers to restraining, slowing, stopping, or reversing the progression or severity of an existing symptom, condition or disorder.

As used herein, the term "reducing weight gain" refers to diminishing the increase in weight of a patient. The term "reducing weight regain" refers to diminishing the increase in weight of a patient experiencing rebound in weight after weight loss. Weight regain may be due to a rebound effect following cessation of weight loss achieved via diet, exercise, behavior modification, or approved therapies. For avoidance of doubt weight gain or weight regain as used herein refers to weight gain or weight regain induced by food intake or eating habits and does not refer to non-food related weight gain such as build up of fluids, weight due to water retention, muscle mass, or inflammation.

An "ischemic event" as used herein refers to an insufficient supply of blood to an organ or body part. The decrease in blood flow reduces the supply of oxygen to the affected organ or body part. An ischemic event may also be known as ischemia. One skilled in the art will know that ischemia can affect different organs or parts of the body, for example the heart, such as myocardial ischemia or cardiac ischemia, or the brain, such as cerebral ischemia.

"Addiction disorders" as used herein describes excessive maladaptive behaviors for which an individual exhibits an inability to control despite negative consequences. Of particular relevance to the present invention are addiction disorders involving consummatory behaviors such as alcohol intake, smoking, overeating, and use of illicit drugs. This invention normalizes aberrant incentive and reward neural substrates that are dysregulated in individuals with addictive disorders. Stress is often a precipitating agent in the etiology and maintenance of addictive disorders; this invention provides a method to ameliorate the consequences of stress that promote addictive behaviors.

A compound of the present invention may react to form pharmaceutically acceptable salts. Pharmaceutically acceptable salts and common methodology for preparing them are well known in the art. See, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977.

The skilled artisan will appreciate that the compounds of the invention, or pharmaceutically acceptable salts thereof, are comprised of a core that contains at least one chiral center, represented by * in (I) below:

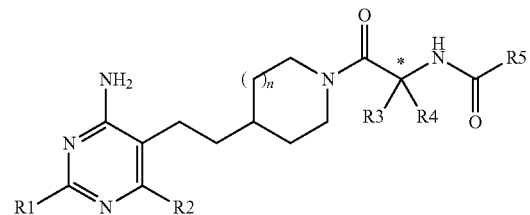

Preferred compounds of the invention are represented by (II), wherein $R^3$ is —H and $R^4$ is —$CH_3$:

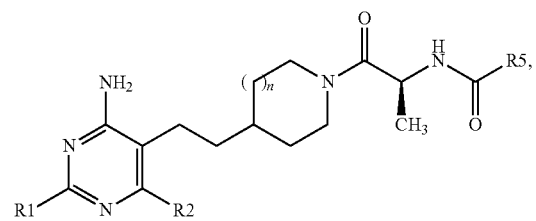

or pharmaceutically acceptable salts thereof.

The skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers of compounds of the invention are a preferred embodiment of the invention.

A compound of the present invention is preferably formulated as pharmaceutical compositions administered by a variety of routes, such as oral administration. Such pharmaceutical compositions and processes for preparing the same are well known in the art. See, e.g., *Remington: The Science and Practice of Pharmacy* (A. Gennaro, et al., eds., 21st ed., Mack Publishing Co., 2005). More particularly preferred, is a pharmaceutical composition comprising a compound of the invention represented by the formula

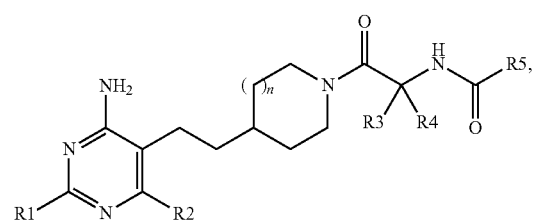

wherein
n is 1 or 2;
$R^1$ and $R^2$ are selected from —$CH_3$ and —Cl, so long as $R^1$ and $R^2$ are not both —$CH_3$ or both —Cl;
$R^3$ and $R^4$ are selected from —H and —$CH_3$, so long as $R^3$ and $R^4$ are not both —$CH_3$;
$R^5$ is selected from —$C_1$-$C_3$ alkyl optionally substituted with —OH or —$CF_3$; —$OC_1$-$C_4$ alkyl; $C_3$-$C_6$ cycloalkyl; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, pyrimidinyl, or pyrazinyl; and phenyl optionally substituted with —$OCH_3$;
provided that when n is 1, $R^1$ is —$CH_3$, $R^2$ is —Cl, $R^3$ is —$CH_3$, and $R^4$ is —H, then $R^5$ cannot be cyclopropyl or a pharmaceutically acceptable salt thereof and one or more pharmaceutically acceptable carriers or diluents.

Although all of the exemplified compounds of the invention are GOAT inhibitors, certain classes of compounds are preferred. The following paragraphs describe such preferred classes:
a) n is 1;
b) n is 2;
c) $R^1$ is —$CH_3$ and $R^2$ is —Cl;
d) $R^1$ is —Cl and $R^2$ is-$CH_3$;
e) $R^3$ is —$CH_3$ and $R^4$ is —H;
f) $R^3$ and $R^4$ are —H;
g) $R^5$ is —$C_1$-$C_3$ alkyl optionally substituted with —OH or —$CF_3$; —$OC_1$-$C_4$ alkyl; cyclopropyl; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, pyrimidinyl, or pyrazinyl; or phenyl optionally substituted with —$OCH_3$;
h) $R^5$ is —$C_1$-$C_3$ alkyl optionally substituted with —OH or —$CF_3$; —$OCH_3$ or —$OC(CH_3)_3$; cyclopropyl; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, pyrimidinyl, or pyrazinyl; or phenyl optionally substituted with —$OCH_3$;
i) $R^5$ is —$OC_1$-$C_4$ alkyl;
j) $R^5$ is —$OCH_3$ or —$OC(CH_3)_3$;
k) $R^5$ is pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$;
l) $R^5$ is pyrazolyl, oxazolyl, thiazolyl, or thiadiazolyl, wherein pyrazolyl, oxazolyl, or thiazolyl each may be optionally substituted one time with —$CH_3$ or —$CH_2CH_3$;
m) $R^5$ is pyrazolyl, which may be optionally substituted two times with —$CH_3$;
n) $R^5$ is pyrazolyl, which may be optionally substituted one time with —$CH_2CH_3$;
o) $R^5$ is pyridinyl, pyridazinyl, pyrimidinyl, or pyrazinyl;
p) $R^5$ is phenyl optionally substituted with —$OCH_3$;
q) $R^5$ is cyclopropyl;
r) $R^5$ is —$C_1$-$C_3$ alkyl optionally substituted with —OH or —$CF_3$;
s) $R^5$ is —$C_1$-$C_3$ alkyl optionally substituted with —OH or —$CF_3$; —$OC_1$-$C_4$ alkyl; cyclopropyl; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, or pyrazinyl; or phenyl optionally substituted with —$OCH_3$;
t) $R^5$ is —$C_1$-$C_3$ alkyl optionally substituted with —OH or —$CF_3$; —$OCH_3$ or —$OC(CH_3)_3$; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, or pyrazinyl; or phenyl optionally substituted with —$OCH_3$;
u) $R^5$ is pyridinyl, pyridazinyl, or pyrazinyl; or phenyl optionally substituted with —$OCH_3$;
v) $R^5$ is —$C_1$-$C_3$ alkyl optionally substituted with —OH or —$CF_3$ or —$OCH_3$ or —$OC(CH_3)_3$;
w) $R^5$ is pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$;
x) $R^5$ is pyridinyl, pyridazinyl, or pyrazinyl; or phenyl optionally substituted with —$OCH_3$;
y) $R^5$ is pyrazolyl, oxazolyl, or thiazolyl, wherein each may be optionally substituted one to two times with —$CH_3$ or —$CH_2CH_3$;
z) $R^5$ is pyridinyl or pyridazinyl; or phenyl optionally substituted with —$OCH_3$;
aa) $R^5$ is pyridinyl or pyridazinyl;
bb) $R^5$ is —$OC(CH_3)_3$;
cc) $R^5$ is —$CH_3$, or —$CH_2CH_3$, optionally substituted with —OH; —$OCH_3$ or —$OC(CH_3)_3$; cyclopropyl; pyrrolidinyl, optionally substituted with —$C(O)CH_3$; pyrazolyl, oxazolyl, or thiazolyl, wherein each may be optionally substituted with —$CH_3$ or —$CH_2CH_3$; pyridinyl, or pyridazinyl; or phenyl optionally substituted with —$OCH_3$;
dd) $R^5$ is cyclopropyl; pyrrolidinyl, optionally substituted with —$C(O)CH_3$; pyrazolyl, oxazolyl, or thiazolyl, wherein each may be optionally substituted with —$CH_3$ or —$CH_2CH_3$; pyridinyl, or pyridazinyl; or phenyl optionally substituted with —$OCH_3$;
ee) $R^5$ is cyclopropyl; pyrrolidinyl, optionally substituted with —$C(O)CH_3$;
ff) $R^5$ is pyrazolyl, oxazolyl, or thiazolyl, wherein each may be optionally substituted with —$CH_3$ or —$CH_2CH_3$; pyridinyl, or pyridazinyl; or phenyl optionally substituted with —$OCH_3$;
gg) $R^5$ is pyrazolyl, oxazolyl, or thiazolyl, wherein each may be optionally substituted with —$CH_3$ or —$CH_2CH_3$;
hh) $R^5$ is —$CH_3$ or —$CH_2CH_3$, optionally substituted with —OH; —$OCH_3$ or —$OC(CH_3)_3$;
ii) $R^5$ is —$CH_3$, or —$CH_2CH_3$, optionally substituted with —OH;
jj) $R^5$ is —$OCH_3$ or —$OC(CH_3)_3$;
kk) $R^5$ is —$C_1$-$C_3$ alkyl optionally substituted with —$CF_3$; —$OCH_3$ or —$OC(CH_3)_3$, pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, or pyrazinyl; or phenyl optionally substituted with —$OCH_3$;
ll) $R^5$ is —$C_1$-$C_3$ alkyl optionally substituted with —$CF_3$; —$OCH_3$, or —$OC(CH_3)_3$; pyrazolyl, oxazolyl, thiazolyl, or thiadiazolyl, wherein pyrazolyl, oxazolyl, or thiazolyl each may be optionally substituted one to two times with —$CH_3$ or —$CH_2CH_3$; pyridinyl, pyridazinyl, or pyrazinyl; or phenyl optionally substituted with —$OCH_3$;
mm) $R^5$ is —$C_1$-$C_3$ alkyl optionally substituted with —$CF_3$; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, or pyrazinyl; or phenyl optionally substituted with —OCH₃;

nn) R⁵ is pyrazolyl, oxazolyl, or thiazolyl, wherein each may be optionally substituted with —CH₃; or phenyl optionally substituted with —OCH₃;

oo) R⁵ is pyrazolyl or oxazolyl, wherein each may be optionally substituted with —CH₃;

pp) R⁵ is —CH₃, —OCH₃ pyrazolyl, or thiazolyl, wherein pyrazolyl or thiazolyl may be optionally substituted with —CH₃;

qq) R⁵ is not cyclopropyl when R¹ is —CH₃ and R² is —Cl;

rr) When R³ or R⁴ is —CH₃, the configuration of the carbon atom with said —CH₃ is (S); and ss) the compound of the present invention is the free base.

A preferred embodiment of the present invention relates to compounds of the formula,

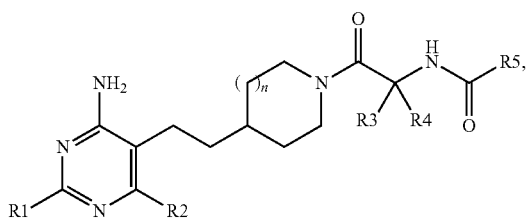

wherein
n is 1 or 2;
R¹ and R² are selected from —CH₃ and —Cl, so long as R¹ and R² are not both —CH₃ or both —Cl;
R³ and R⁴ are selected from —H and —CH₃ so long as R³ and R⁴ are not both —CH₃;
R⁵ is selected from —C₁-C₃ alkyl optionally substituted with —OH or —CF₃; —OC₁-C₄ alkyl; cyclopropyl; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, pyrimidinyl, or pyrazinyl; and phenyl optionally substituted with —OCH₃;
provided that when n is 1, R¹ is —CH₃, R² is —Cl, R³ is —CH₃, and R⁴ is —H, then R⁵ cannot be cyclopropyl; or a pharmaceutically acceptable salt thereof. In a further embodiment, when R³ or R⁴ is —CH₃, the configuration of the carbon atom with said —CH₃ is (S).

Another preferred embodiment of the present invention relates to compounds wherein, n is 1 or 2; R¹ and R² are selected from —CH₃ and —Cl, so long as R¹ and R² are not both —CH₃ or both —Cl; R³ and R⁴ are selected from —H and —CH₃ so long as R³ and R⁴ are not both —CH₃; R⁵ is selected from —C₁-C₃ alkyl optionally substituted with —OH or —CF₃; —OCH₃ or —OC(CH₃)₃; cyclopropyl; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, pyrimidinyl, or pyrazinyl; and phenyl optionally substituted with —OCH₃; provided that when n is 1, R¹ is —CH₃, R² is —Cl, R³ is —CH₃, and R⁴ is —H, then R⁵ cannot be cyclopropyl; or a pharmaceutically acceptable salt thereof. In a further embodiment, when R³ or R⁴ is —CH₃, the configuration of the carbon atom with said —CH₃ is (S).

Another preferred embodiment of the present invention relates to compounds of the formula,

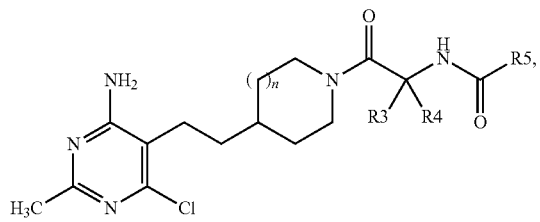

wherein
n is 1 or 2; R³ and R⁴ are selected from —H and —CH₃, so long as R³ and R⁴ are not both —CH₃; R⁵ is selected from —C₁-C₃ alkyl optionally substituted with —OH or —CF₃; —OCH₃ or —OC(CH₃)₃; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, pyrimidinyl, or pyrazinyl; and phenyl optionally substituted with —OCH₃; or a pharmaceutically acceptable salt thereof. In a further embodiment, when R³ or R⁴ is —CH₃, the configuration of the carbon atom with said —CH₃ is (S).

In another preferred embodiment, n is 1 or 2; R³ and R⁴ are selected from —H and —CH₃, so long as R³ and R⁴ are not both —CH₃; R⁵ is —C₁-C₃ alkyl optionally substituted with —OH or —CF₃ or —OCH₃ or —OC(CH₃)₃; or a pharmaceutically acceptable salt thereof. In a further embodiment, when R³ or R⁴ is —CH₃, the configuration of the carbon atom with said —CH₃ is (S).

In another preferred embodiment, n is 1 or 2; R³ and R⁴ are selected from —H and —CH₃, so long as R³ and R⁴ are not both —CH₃; R⁵ is pyrazolyl, oxazolyl, thiazolyl, or thiadiazolyl, wherein pyrazolyl, oxazolyl, or thiazolyl each may be optionally substituted one to two times with —CH₃ or —CH₂CH₃; or a pharmaceutically acceptable salt thereof. In a further embodiment, when R³ or R⁴ is —CH₃, the configuration of the carbon atom with said —CH₃ is (S).

In yet another preferred embodiment, n is 1 or 2; R³ and R⁴ are selected from —H and —CH₃, so long as R³ and R⁴ are not both —CH₃; R⁵ is pyridinyl, pyridazinyl, pyrimidinyl, or pyrazinyl; or phenyl optionally substituted with —OCH₃; or a pharmaceutically acceptable salt thereof. In a further embodiment, when R³ or R⁴ is —CH₃, the configuration of the carbon atom with said —CH₃ is (S).

In a further preferred embodiment, of the present invention relates to compounds of the formula, n is 1 or 2; R³ and R⁴ are selected from —H and —CH₃, so long as R³ and R⁴ are not both —CH₃; R⁵ is pyridinyl, pyridazinyl, pyrimidinyl, or pyrazinyl; or a pharmaceutically acceptable salt thereof. In a further embodiment, when R³ or R⁴ is —CH₃, the configuration of the carbon atom with said —CH₃ is (S).

In yet a further preferred embodiment, n is 1 or 2; R³ and R⁴ are selected from —H and —CH₃, so long as R³ and R⁴ are not both —CH₃; R⁵ is phenyl optionally substituted with —OCH₃; or a pharmaceutically acceptable salt thereof. In a further embodiment, when R³ or R⁴ is —CH₃, the configuration of the carbon atom with said —CH₃ is (S).

Another preferred embodiment of the present invention relates to compounds of the formula,

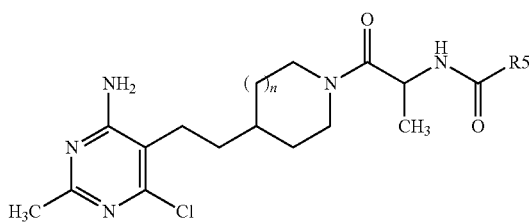

n is 1 or 2; R⁵ is —OCH₃ or —OC(CH₃)₃; or a pharmaceutically acceptable salt thereof. In a further embodiment, the configuration of the carbon atom with the —CH₃ group attached is (S).

Another preferred embodiment of the present invention relates to compounds of the formula,

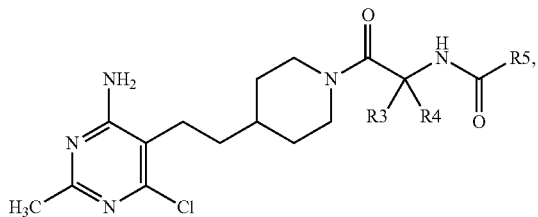

wherein R³ and R⁴ are selected from —H and —CH₃, so long as R³ and R⁴ are not both —CH₃; R⁵ is pyrazolyl, oxazolyl, thiazolyl, or thiadiazolyl, wherein pyrazolyl, oxazolyl, or thiazolyl each may be optionally substituted one to two times with —CH₃ or —CH₂CH₃; or a pharmaceutically acceptable salt thereof. In a further embodiment, when R³ or R⁴ is —CH₃, the configuration of the carbon atom with said —CH₃ is (S).

In yet another preferred embodiment, R³ and R⁴ are selected from —H and —CH₃, so long as R³ and R⁴ are not both —CH₃; R⁵ is pyridinyl, pyridazinyl, pyrimidinyl, or pyrazinyl; or phenyl optionally substituted with —OCH₃; or a pharmaceutically acceptable salt thereof. In a further preferred embodiment, n is 1 or 2; R⁵ is pyridinyl, pyridazinyl, pyrimidinyl, or pyrazinyl; or a pharmaceutically acceptable salt thereof. In a further embodiment, the configuration of the carbon atom with the —CH₃ group attached is (S).

Another preferred embodiment of the present invention relates to compounds of the formula,

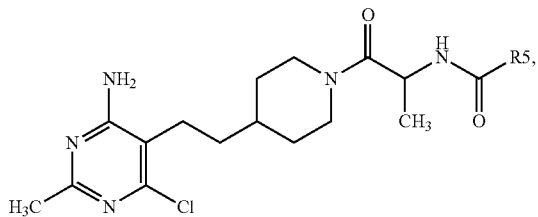

wherein R⁵ is phenyl optionally substituted with —OCH₃; or a pharmaceutically acceptable salt thereof. In yet another preferred embodiment, R⁵ is —OCH₃ or —OC(CH₃)₃; or —C₁-C₃ alkyl optionally substituted with —OH or —CF₃; or a pharmaceutically acceptable salt thereof. In a further embodiment, the configuration of the carbon atom with the —CH₃ group attached is (S).

In another preferred embodiment, R⁵ is —C₁-C₃ alkyl optionally substituted with —OH or —CF₃; or a pharmaceutically acceptable salt thereof. In a further embodiment, the configuration of the carbon atom with the —CH₃ group attached is (S).

In a further preferred embodiment, R⁵ is —OCH₃ or —OC(CH₃)₃; or a pharmaceutically acceptable salt thereof. In a further embodiment, the configuration of the carbon atom with the —CH₃ group attached is (S).

Another preferred embodiment of the present invention relates to compounds of the formula,

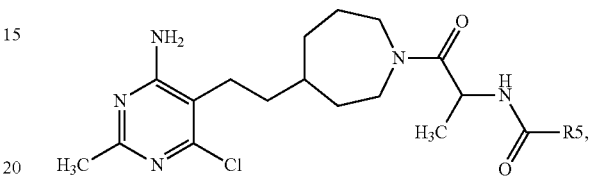

wherein R⁵ is pyrazolyl, oxazolyl, or thiazolyl, wherein each may be optionally substituted one to two times with —CH₃ or —CH₂CH₃; or a pharmaceutically acceptable salt thereof. In a further embodiment, the configuration of the carbon atom with the —CH₃ group attached is (S).

In yet another preferred embodiment, R⁵ is pyridinyl, pyridazinyl, or phenyl optionally substituted with —OCH₃; or a pharmaceutically acceptable salt thereof. In a further preferred embodiment, R⁵ is pyridinyl or pyridazinyl; or a pharmaceutically acceptable salt thereof. In a further embodiment, the configuration of the carbon atom with the —CH₃ group attached is (S).

In yet a further preferred embodiment, R⁵ is phenyl optionally substituted with —OCH₃; or a pharmaceutically acceptable salt thereof. In another preferred embodiment, R⁵ is —OC(CH₃)₃; or a pharmaceutically acceptable salt thereof. In a further embodiment, the configuration of the carbon atom with the —CH₃ group attached is (S).

Another preferred embodiment of the present invention relates to compounds of the formula,

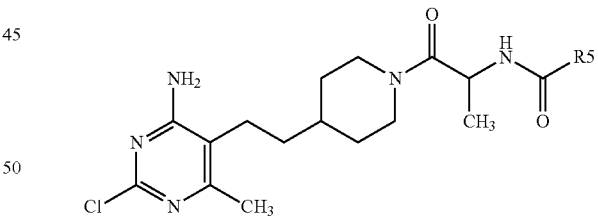

R⁵ is selected from —CH₃, or —CH₂CH₃, optionally substituted with —OH; —OCH₃ or —OC(CH₃)₃; cyclopropyl; pyrrolidinyl, optionally substituted with —C(O)CH₃; pyrazolyl, oxazolyl, or thiazolyl, wherein each may be optionally substituted with —CH₃ or —CH₂CH₃; pyridinyl, or pyridazinyl; and phenyl optionally substituted with —OCH₃; or a pharmaceutically acceptable salt thereof. In a further embodiment, the configuration of the carbon atom with the —CH₃ group attached is (S).

In yet another preferred embodiment, R⁵ is cyclopropyl; pyrrolidinyl, optionally substituted with —C(O)CH₃; pyrazolyl, oxazolyl, or thiazolyl, wherein each of pyrazolyl, oxazolyl, or thiazolyl may be optionally substituted with —CH₃ or —CH₂CH₃; pyridinyl, or pyridazinyl; or phenyl optionally substituted with —OCH₃; or a pharmaceutically acceptable salt thereof. In a further embodiment, the configuration of the carbon atom with the —CH₃ group attached is (S).

In a further preferred embodiment, $R^5$ is pyrazolyl, oxazolyl, or thiazolyl, wherein each may be optionally substituted with —CH₃ or —CH₂CH₃; pyridinyl, or pyridazinyl; or phenyl optionally substituted with —OCH₃; or a pharmaceutically acceptable salt thereof.

In a further embodiment, the configuration of the carbon atom with the —CH₃ group attached is (S).

In another embodiment, $R^5$ is pyrazolyl, oxazolyl, or thiazolyl, wherein each pyrazolyl, oxazolyl, or thiazolyl may be optionally substituted with —CH₃ or —CH₂CH₃; pyridinyl, or pyridazinyl; or a pharmaceutically acceptable salt thereof. In a further embodiment, the configuration of the carbon atom with the —CH₃ group attached is (S).

In another embodiment, $R^5$ is pyrazolyl, oxazolyl, or thiazolyl, wherein each may be optionally substituted with —CH₃ or —CH₂CH₃; or a pharmaceutically acceptable salt thereof. In a further embodiment, the configuration of the carbon atom with the —CH₃ group attached is (S).

In yet another embodiment, $R^5$ is pyridinyl or pyridazinyl; or a pharmaceutically acceptable salt thereof. In a further embodiment, $R^5$ is phenyl optionally substituted with —OCH₃; or a pharmaceutically acceptable salt thereof. In another preferred embodiment, $R^5$ is cyclopropyl; or a pharmaceutically acceptable salt thereof. In a further embodiment, the configuration of the carbon atom with the —CH₃ group attached is (S).

In yet another preferred embodiment, $R^5$ is —CH₃ or —CH₂CH₃, optionally substituted with —OH; or —OCH₃ or —OC(CH₃)₃; or a pharmaceutically acceptable salt thereof. In a further embodiment, the configuration of the carbon atom with the —CH₃ group attached is (S).

In a further embodiment, $R^5$ is —CH₃ or —CH₂CH₃, optionally substituted with —OH; or a pharmaceutically acceptable salt thereof. In a further embodiment, the configuration of the carbon atom with the —CH₃ group attached is (S).

In yet a further embodiment, $R^5$ is —OCH₃ or —OC(CH₃)₃; or a pharmaceutically acceptable salt thereof. In a further embodiment, the configuration of the carbon atom with the —CH₃ group attached is (S).

A preferred embodiment of the present invention relates to compounds of the formula,

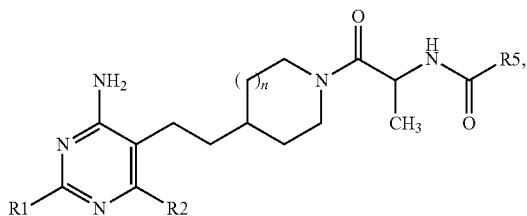

wherein
n is 1 or 2;
$R^1$ and $R^2$ are selected from —CH₃ and —Cl, so long as $R^1$ and $R^2$ are not both —CH₃ or both —Cl;
$R^5$ is selected from —C₁-C₃ alkyl optionally substituted with —CF₃; —OCH₃ or —OC(CH₃)₃; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, or pyrazinyl; and phenyl optionally substituted with —OCH₃; or a pharmaceutically acceptable salt thereof. In a further embodiment, the configuration of the carbon atom with the —CH₃ group attached is (S).

A preferred embodiment of the present invention relates to compounds of the formula,

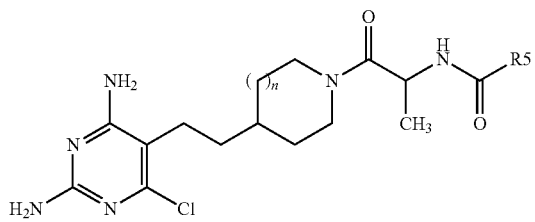

wherein
n is 1 or 2;
$R^5$ is selected from —C₁-C₃ alkyl optionally substituted with —CF₃; —OCH₃, or —OC(CH₃)₃; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, or pyrazinyl; and phenyl optionally substituted with —OCH₃; or a pharmaceutically acceptable salt thereof. In a further embodiment, the configuration of the carbon atom with the —CH₃ group attached is (S).

In a further preferred embodiment, n is 1 or 2; $R^5$ is selected from —C₁-C₃ alkyl optionally substituted with —CF₃; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, or pyrazinyl; and phenyl optionally substituted with —OCH₃; or a pharmaceutically acceptable salt thereof. In a further embodiment, the configuration of the carbon atom with the —CH₃ group attached is (S).

A preferred embodiment of the present invention relates to compounds of the formula,

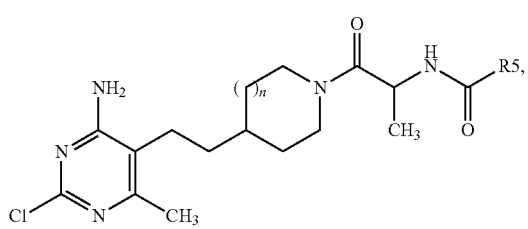

wherein $R^5$ is pyrazolyl, oxazolyl, or thiazolyl, wherein each may be optionally substituted with —CH₃; or phenyl optionally substituted with —OCH₃; or a pharmaceutically acceptable salt thereof. In a further embodiment, the configuration of the carbon atom with the —CH₃ group attached is (S).

A preferred embodiment of the present invention relates to compounds of the formula,

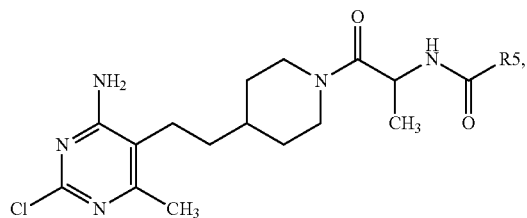

wherein R[5] is pyrazolyl or oxazolyl, wherein each may be optionally substituted with —CH₃; or a pharmaceutically acceptable salt thereof. In a further embodiment, the configuration of the carbon atom with the —CH₃ group attached is (S).

Another preferred embodiment of the present invention relates to compounds of the formula,

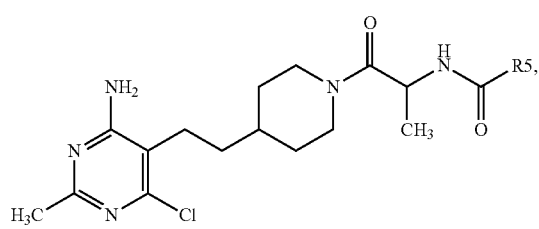

wherein R[5] is —CH₃; —OCH₃; or pyrazolyl or thiazolyl, wherein pyrazolyl or thiazolyl may be optionally substituted with —CH₃; or a pharmaceutically acceptable salt thereof. In a further embodiment, the configuration of the carbon atom with the —CH₃ group attached is (S).

A further preferred embodiment of the present invention relates to compounds of the formula:

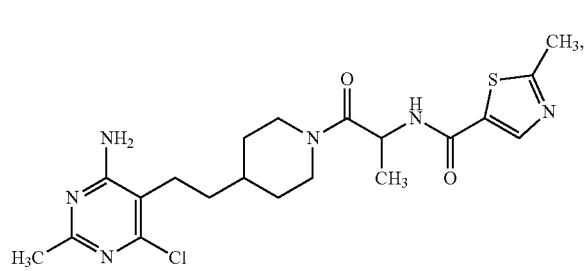 [SMILES: Cc1nc(N)c(CCC2CCN(C(=O)C(C)NC(=O)c3cnc(C)s3)CC2)c(Cl)n1]

or a pharmaceutically acceptable salt thereof.

An especially preferred embodiment of the present invention relates to the compound,

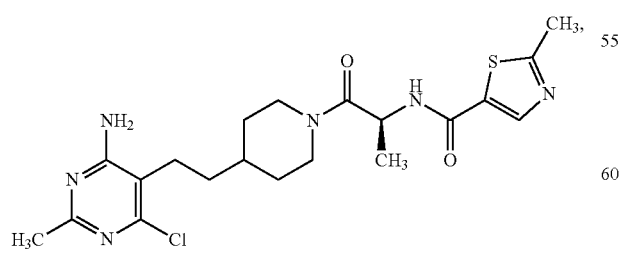

or a pharmaceutically acceptable salt thereof.

An especially preferred embodiment of the present invention relates to the compound,

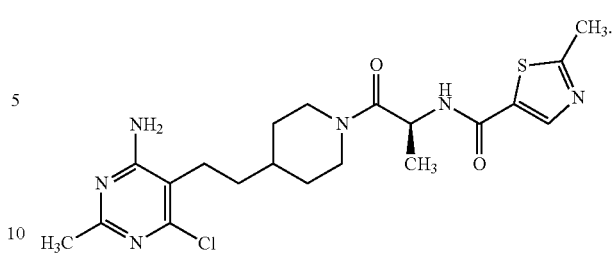

Another preferred embodiment of the present invention relates to compounds of the formula,

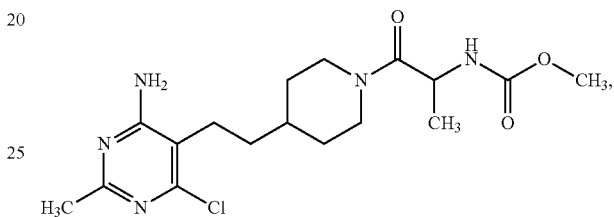

or a pharmaceutically acceptable salt thereof.

Another especially preferred embodiment of the present invention relates to the compound,

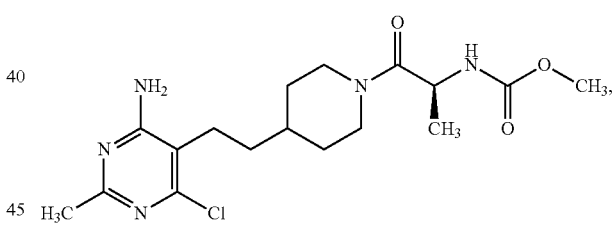

or a pharmaceutically acceptable salt thereof.

Another especially preferred embodiment of the present invention relates to the compound,

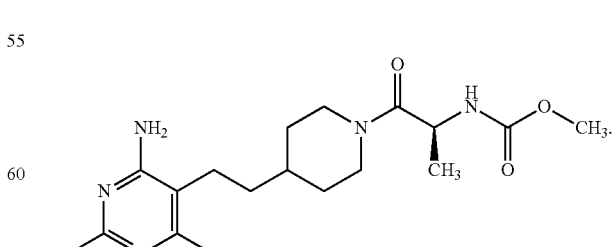

Another preferred embodiment of the present invention relates to compounds of the formula,

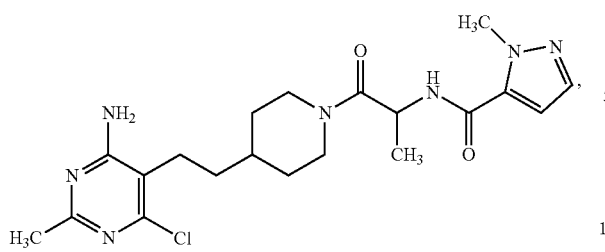

or a pharmaceutically acceptable salt thereof.

Another especially preferred embodiment of the present invention relates to the compound,

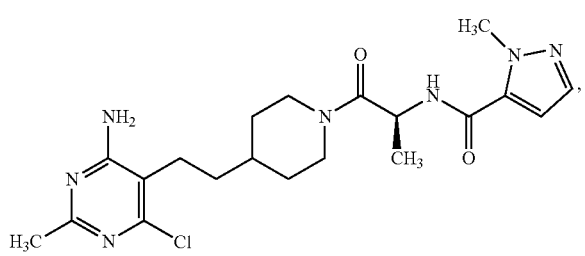 [SMILES: Cc1nc(N)c(CCC2CCN(C(=O)[C@H](C)NC(=O)c3ccnn3C)CC2)c(Cl)n1]

or a pharmaceutically acceptable salt thereof.

Another especially preferred embodiment of the present invention relates to the compound,

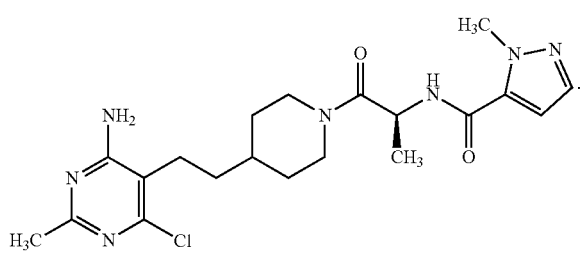 [SMILES: Cc1nc(N)c(CCC2CCN(C(=O)[C@H](C)NC(=O)c3ccnn3C)CC2)c(Cl)n1]

Another preferred embodiment of the present invention relates to compounds of the formula,

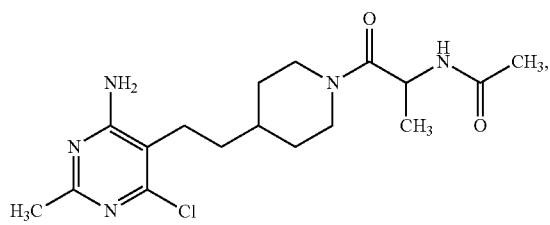 [SMILES: CC(=O)NC(C)C(=O)N1CCC(CCc2c(N)nc(C)nc2Cl)CC1]

or a pharmaceutically acceptable salt thereof.

Another especially preferred embodiment of the present invention relates to the compound,

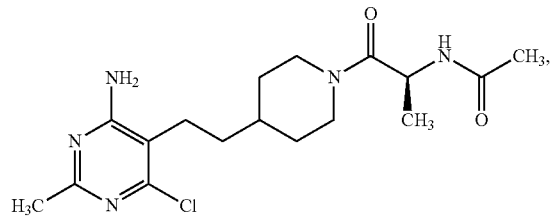 [SMILES: CC(=O)N[C@@H](C)C(=O)N1CCC(CCc2c(N)nc(C)nc2Cl)CC1]

or a pharmaceutically acceptable salt thereof.

Another especially preferred embodiment of the present invention relates to the compound,

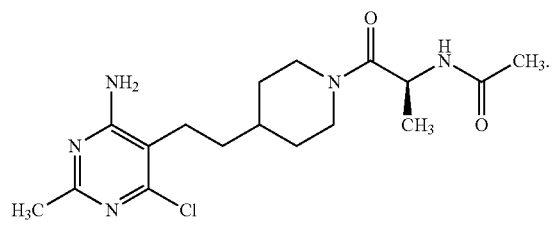 [SMILES: CC(=O)N[C@@H](C)C(=O)N1CCC(CCc2c(N)nc(C)nc2Cl)CC1]

The compound of the present invention is generally effective over a wide dosage range. For example, dosages per day fall within the range of about 0.03 to about 30 mg/Kg of body weight. In some instances dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

It is well known in the art that agents for the treatment of diabetes and/or obesity may be combined with other agents for the treatment of diabetes and/or obesity. The compound of the invention, or a pharmaceutically acceptable salt thereof, may be co-administered, simultaneously or sequentially, with other effective treatment(s) for diabetes or obesity. The compound of the invention, or a pharmaceutically acceptable salt thereof, alone or in combination with other effective treatment(s) may be administered, simultaneously or sequentially, following approved medical procedures such as bariatric surgeries, for example, gastric bypass surgery or adjustable gastric banding procedures.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds or salts of the present invention. The products of each step in the Schemes below can be recovered by conventional methods well known in the art, including extraction, evaporation, precipitation, chromatography, filtration, trituration, and crystallization. In the Schemes below, all substituents unless otherwise indicated, are as previously defined. The reagents and starting materials are readily available to one of ordinary skill in the art.

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain stereochemical centers have been left unspecified and certain substituents have been eliminated in the following schemes for the sake of clarity and are not intended to limit the teaching of the schemes in any way. Single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as single a enantiomer or diastereomer. The single enantiomer or diastereomer may be prepared beginning with chiral reagents or by stereoselective or stereospecific synthetic techniques. Alternatively, the single enantiomer or diastereomer may be isolated from mixtures by standard chiral chromatographic or crystallization techniques. The skilled artisan will appreciate that in some circumstances the elution order of enantiomers or diastereomers may be different due to different chromatographic columns and mobile phases.

Certain abbreviations are defined as follows: "ACN" refers to acetonitrile; "BSA" refers to Bovine Serum Albumin; "DCC" refers to 1,3-dicyclohexylcarbodiimide; "DCM" refers to dichloromethane; "DIC" refers to diisopropylcarbodiimide; "DIPEA" refers to diisopropylethylamine or N-ethyl-N-isopropyl-propan-2-amine; "DMAP" refers to dimethylaminopyridine; "DMF" refers to dimethylformamide; "DMSO" refers to dimethylsulfoxide; "EDCI" refers to 1-(3-dimethylaminopropyl)-3-ethylcarbodiimide hydrochloride; "EDTA" refers to ethylenediaminetetraacetic acid; "ee" refers to enantiomeric excess; "ELISA" refers to enzyme-linked immuno assay, "EtOAc" refers to ethyl acetate; "EtOH" refers to ethanol or ethyl alcohol; "Ex" refers to example; "FBS" refers to retal bovine serum; "HATU" refers to (dimethylamino)-N,N-dimethyl (3H-[1,2,3]triazolo[4,5-b]pyridin-3-yloxy)methaniminium hexafluorophosphate; "HOAt" refers to 1-hydroxy-7-azobenzotriazole; "HOBt" refers to 1-hydroxylbenzotriazole hydrate; "HBTU" refers to refers to 2-(1H-benzotriazole-1-yl)-1,1,3,3-tetramethyluronium hexafluorophosphate; "HPLC" refers to High Performance Liquid Chromatography; "HRP" refers to horseradish peroxidase; "IC$_{50}$" refers to the concentration of an agent that produces 50% of the maximal inhibitory response possible for that agent; "IPA" refers to isopropyl alcohol; "LC-ES/MS" refers to Liquid Chromatography-Electrospray Mass Spectrometry; "MeOH" refers to MeOH or methyl alcohol; "MS" refers to Mass Spectrometry; "min" refers to minute or minutes; "OAc" refers to acetate; "PBS" refers to phosphate buffered saline; "PG" refers to protecting group; "Prep" refers to preparation; "PyBOP" refers to benzotriazol-1-yloxytripyrrolidino-phosphonium hexafluorophosphate; "PyBrop" refers to bromo-tris-pyrrolidino phosphoniumhexafluoro phosphate; "RT" refers to room temperature; "SCX" refers to strong cation exchange; "SFC" refers to supercritical fluid chromatography; "SPE" refers to solid phase extraction; "TEA" refers to triethylamine "TFA" refers to trifluoroacetic acid; "TMB" refers to 3,3',5,5'-tetramethylbenzidine; and "T$_R$" refers to time of retention.

In the Schemes below, all substituents unless otherwise indicated, are as previously defined. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

Scheme 1

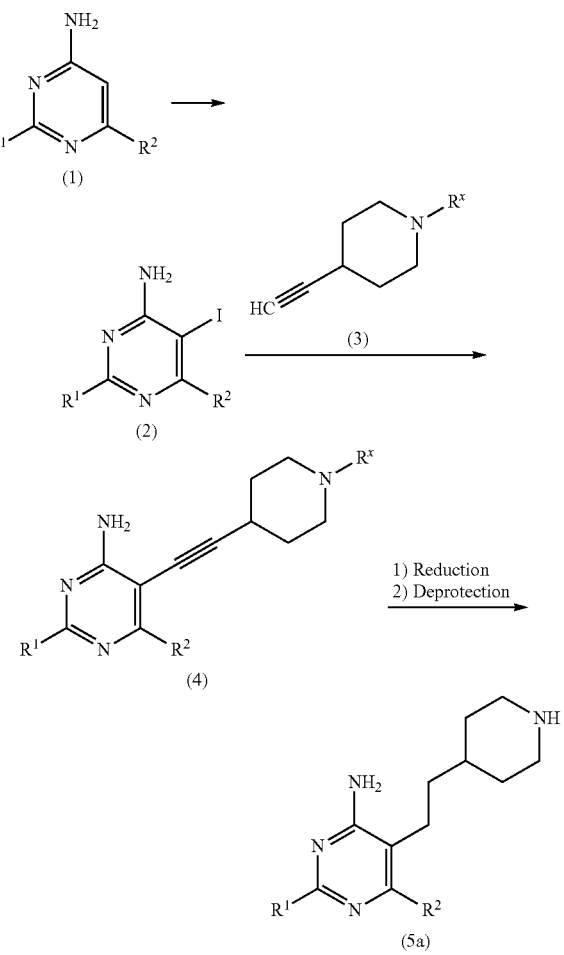

In scheme 1, R$^x$ is an appropriate amine protecting group. Amine protecting groups are well known and appreciated in the art, and may include carbamates and amides. One skilled in the art is familiar with alternative reagents and procedures to add and remove said protecting groups.

Compound (2) may be prepared by treating compound (1) with a halogenating agent, such as iodine monochloride, $I_2$, or N-iodosuccinimide. One skilled in the art will recognize that there are a number of methods of heteroaromatic halogenation. In a further step, compound (4) may be prepared by coupling compound (2) with commercially available alkyne (3) under standard coupling conditions, for example, utilizing a palladium derived organometallic reagent such as $Pd(PPh_3)_2Cl_2$, $Pd(OAc)_2$, or $Pd_2(dba)_3$ in the presence of a catalyst, such as CuI, and a base, such as $Et_3N$, DIPEA, $K_2CO_3$ or $Cs_2CO_3$. Alternatively, the corresponding free amine of compound (3) may be purchased and protected by an appropriate amine protecting group. Compound (4) may be reduced by catalytic hydrogenation in the presence of a transition metal catalyst such as platinum oxide. One skilled in the art would recognize that there are other methods to reduce an alkyne in the presence of an aryl halide. The amine protecting group may then be removed under conditions well known in the art, such as under appropriate acidic or basic conditions to provide compound (5a).

In scheme 2, $R^z$ is an appropriate enolate activation group. Enolate activation groups are well known and appreciated in the art. Compound (7) may be prepared from compound (2) and silylated acetylene (6) by performing a coupling similar to the coupling for compound (3) in scheme 1 above, followed by deprotection of the alkyne. The skilled artisan is familiar with methods to prepare alternative silyl acetylenes.

The activated enolate, compound (8), may be prepared from the corresponding ketone by using an appropriate base, such as LiHMDS or LDA, and the appropriate activating agent such as N-phenylbis(trifluoromethane-sulfonimide) or nonafluorobutanesulfonyl fluoride. In a further step, compound (9) can be prepared by coupling compound (7) and compound (8). The coupling takes place in the presence of a catalytic amount of a palladium catalyst, such as bis(triphenylphosphine)palladium(I) chloride and copper(I) iodide. The skilled artisan is familiar with other coupling conditions, such as those included for compound (4) in Scheme 1 above. Finally, compound (5b) may be prepared from compound (9) by reducing the alkyne and deprotecting the amine as in the method described for preparation of compound (5a) from compound (4) in scheme 1 above.

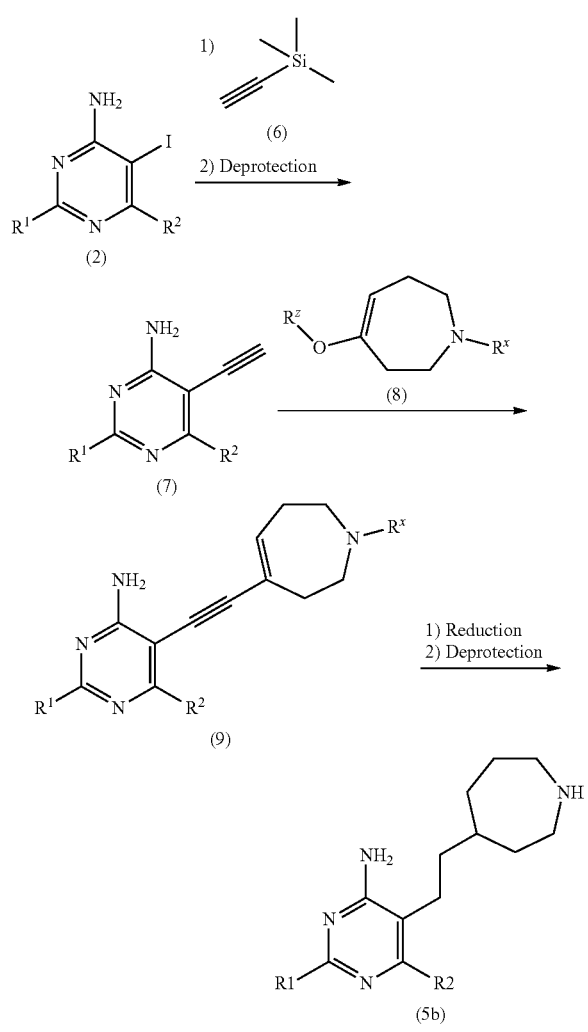

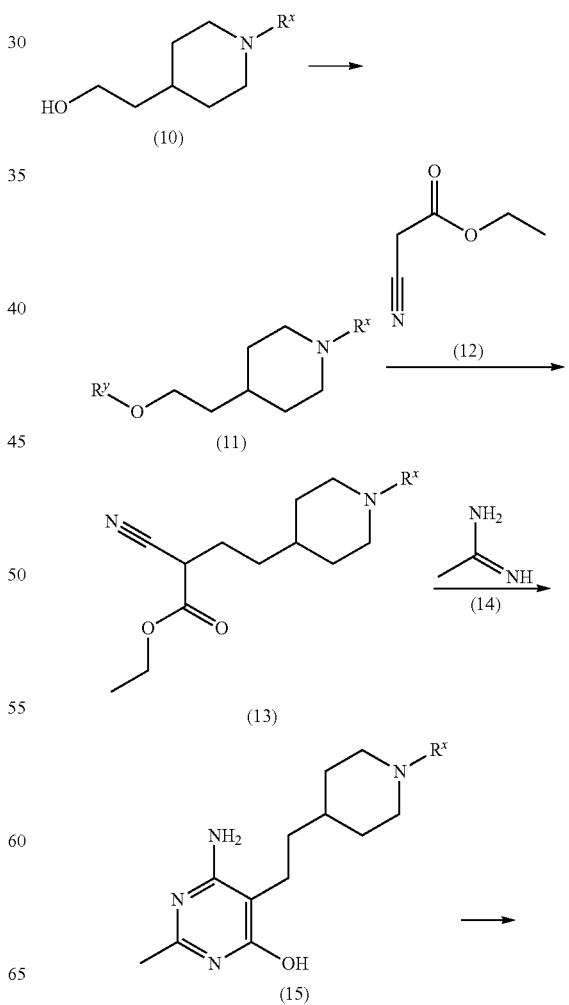

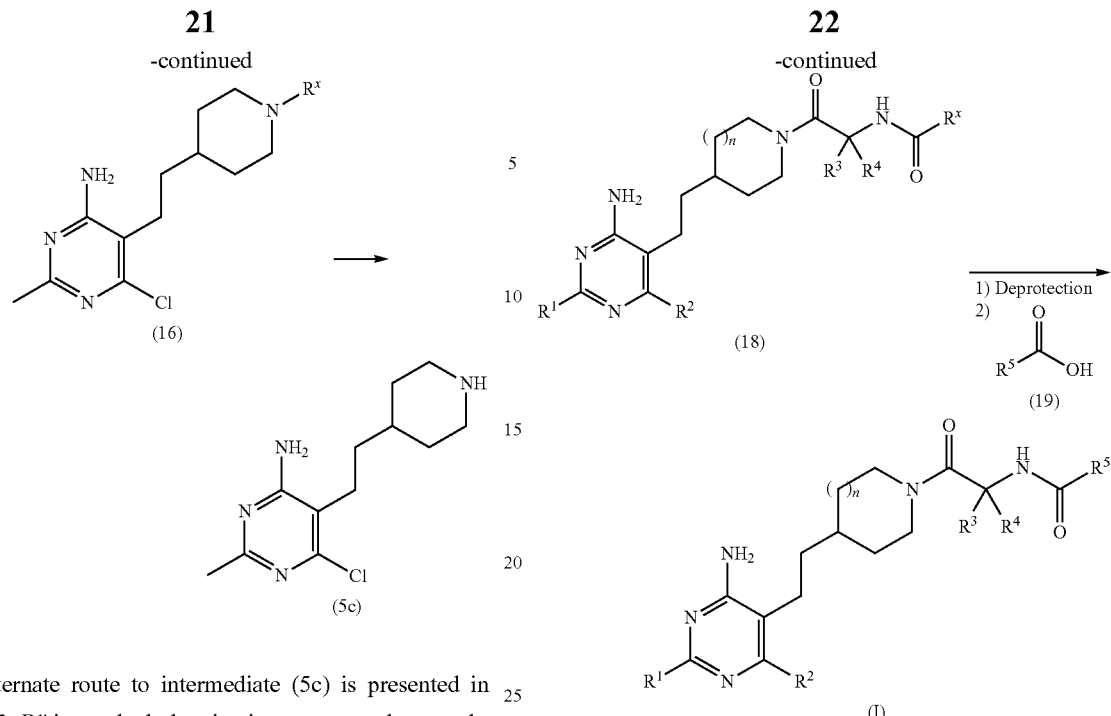

An alternate route to intermediate (5c) is presented in Scheme 3. $R^y$ is an alcohol activation group, such as methanesulfonate, para-toluenesulfonate, or trifluoromethanesulfonate. Compound (11) is prepared from compound (10) by adding an appropriate base, such as triethylamine, pyridine, or DIPEA, followed by the addition of an appropriate sulfonyl chloride. In a further step, compound (13) may be prepared by reacting compound (11) with the anion of compound (12) which is prepared using an appropriate base such as sodium ethoxide, NaH, or n-butyl lithium. Compound (15) is prepared by treating compound (13) with compound (14) in the presence of a base, such as sodium ethoxide in ethanol. In a further step, compound (16) may be prepared by chlorination of compound (15) using an appropriate chlorinating agent, such as $POCl_3$ or $SOCl_2$. Optionally, a catalytic amount of DMF may be added to facilitate chlorination. Finally, compound (5c) may be prepared from compound (16) by deprotecting as in the method described for preparation of compound (5a) from compound (4) in scheme 1 above.

Scheme 4

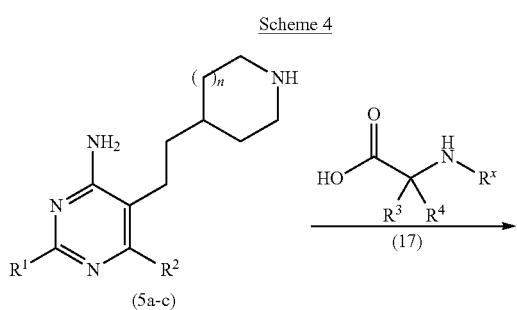

Compound (18) may be synthesized by reacting compound (5a-c) with compound (17), under standard coupling conditions. One skilled in the art will recognize that there are a number of methods and reagents for amide formation resulting from the reaction of carboxylic acids and amines. The coupling of compound (5a-c) with compound (17) can be effected in the presence of a suitable coupling reagent and a suitable amine base, such as DIPEA or trimethylamine. Suitable coupling reagents may include carbodiimides, such as DCC, DIC, EDCI, and other coupling reagents, such as HOBt and HOAt. Additionally, uronium or phosphonium salts of non-nucleophilic anions, such as HATU, HBTU, PYBOP®, and PYBROP® can be used in place of the more traditional coupling reagents. Additives such as DMAP may be used to enhance the reaction. Alternatively, compound (5a-c) can be acylated using substituted acyl chlorides in the presence of a base, such as triethylamine or pyridine.

The amine resulting from deprotection of compound (18) may be reacted with compound (19) under standard amide coupling conditions, including those previously described in the preparation (18), to give a compound of Formula (I). The skilled artisan will recognize that there are alternative methods to prepare a compound of Formula (I) from deprotected compound (18), including reacting with an acid chloride in the presence of an organic base, such as triethylamine, or with an anhydride in the presence of a base and a catalyst, such as DMAP.

In an optional step, a pharmaceutically acceptable salt of a compound of Formula (I) can be formed by reaction of an appropriate free base of Formula (I) with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The designations "isomer 1" and "isomer 2" refer to the compounds that elute from chiral chromatography first and second, respectively, and if chiral chromatography is initiated early in the synthesis, the same designation is applied to subsequent intermediates and examples.

The R or S configuration of the compound of the invention may be determined by standard techniques such as X-ray analysis and correlation with chiral-HPLC retention time. The naming of the following Preparations and Example is generally performed using the IUPAC naming feature in MDL ACCELRYS® Draw version 4.0.NET.

LC-ES/MS is carried on an AGILEN™ HP1100 liquid chromatography system. Electrospray mass spectrometry measurements (acquired in positive mode) are performed on a Mass Selective Detector quadrupole mass spectrometer interfaced to the HP1100 HPLC system using XTERRA® MS C18 columns 2.1×50 mm, 3.5 μm operated to 50° C. The mobile phase is 10 mM ammonium bicarbonate pH 9 (solvent A) and ACN (solvent B). Two mobile phase gradient programs are used:

Gradient program 1 is 5% of solvent A for 0.25 min, gradient from 5-100% of solvent B in 3 min and 100% of solvent B for 0.5 min. The flow rate is 1.1 mL/min and the UV wavelength is set to 214 nm.

Gradient program 2 is from 10-100% of solvent B in 3 min and at 100% of solvent B for 0.75 min. The flow rate is 1.0 mL/min and the UV wavelength is set to 214 nm.

Preparation 1

2-Chloro-5-iodo-6-methyl-pyrimidin-4-amine

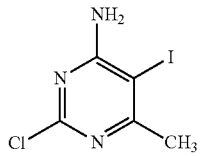

Add a 1M solution of iodine monochloride in DCM (243.77 mL, 243.77 mmol) to a solution of 2-chloro-6-methyl-pyrimidin-4-amine (5.0 g, 34.82 mmol) in MeOH (17 mL) at room temperature. Stir the mixture at room temperature for 16 hours. Upon reaction completion, remove solvent under vacuum to 30 mL, cool to 0° C. and add a 10% aqueous sodium thiosulphate solution (175 mL). Stir the mixture for 10 min and adjust to pH=10 using 2N sodium hydroxide. Extract the mixture with EtOAc (3×100 mL). Dry the organic phase over $Na_2SO_4$, filter and concentrate under reduced pressure. Purify the material using silica gel chromatography eluting with 0-30% acetone in hexane. Concentrate the purified fractions to give the title compound as an off-white solid (6.2 g, 66%). LC-ES/MS m/z ($^{35}Cl/^{37}Cl$) 270/272 (M+H), $T_R$=1.38 min, gradient program 1.

Preparation 2

6-Chloro-5-iodo-2-methyl-pyrimidin-4-amine

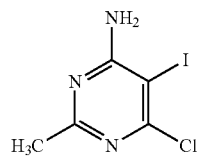

Cool a flask containing 6-chloro-2-methyl-pyrimidin-4-amine (35.3 g, 245 mmol) in methanol (350 mL) to 0-5° C. Add a solution of iodine monochloride (275 g, 1.69 mol) in MeOH over a period of 40 min using an addition funnel. Allow the mixture to slowly warm to room temperature. Stir the mixture at room temperature for 16 hours. Upon reaction completion, cool and add a 20% aqueous sodium sulfite solution (2.3 L). Adjust to pH=6 to 7 using aqueous 5N sodium hydroxide. Filter the solid and wash with water (100 mL). Dry the material under vacuum to obtain the title compound as an off-white solid (56.0 g, 85%). $^1$H NMR (400 MHz, DMSO-$d_6$) δ 7.94 (s, br, 1H), 6.78 (s, br, 1H), 2.27 (s, 3H).

Preparation 3 tert-Butyl 4-[2-(4-amino-2-chloro-6-methyl-pyrimidin-5-yl)ethynyl]piperidine-1-carboxylate

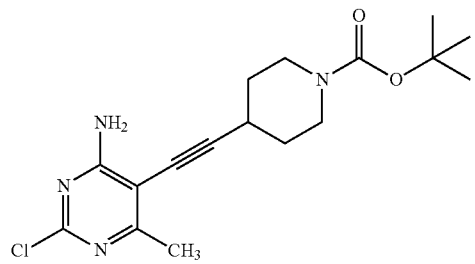 [SMILES: Cc1nc(Cl)nc(N)c1C#CC1CCN(C(=O)OC(C)(C)C)CC1]

Dissolve 2-chloro-5-iodo-6-methyl-pyrimidin-4-amine (30 g, 111.3 mmol), 4-ethynyl-piperidine-1-carboxylic acid tert-butyl ester (34.95 g, 166.99 mmol), bis(triphenylphosphine)palladium(II) chloride (15.63 g, 22.27 mmol) and copper(I) iodide (2.12 g, 11.13 mmol) in TEA (445 mL). Degas the mixture with nitrogen for 15 min. Heat the mixture to 80° C. for 24 hours and then at room temperature for 2 days. Dilute the material with EtOAc (1000 mL) and filter through a plug of diatomaceous earth, wash with EtOAc (500 mL). Wash the organic layer with saturated aqueous sodium chloride (2×300 mL). Dry the organic solution over $Na_2SO_4$, filter, and concentrate under reduced pressure. Purify the material using silica gel chromatography eluting with hexane/EtOAc (1:1). Concentrate the purified fractions to give the title compound as a pale orange powder (24.2 g, 62%). LC-ES/MS m/z ($^{35}Cl/^{37}Cl$) 351/353 (M+H), $T_R$=2.10 min, gradient program 2.

Preparation 4 tert-Butyl 4-[2-(4-amino-6-chloro-2-methyl-pyrimidin-5-yl)ethynyl]piperidine-1-carboxylate

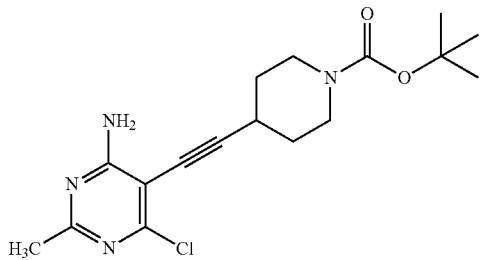 [SMILES: Cc1nc(N)c(C#CC2CCN(C(=O)OC(C)(C)C)CC2)c(Cl)n1]

Dissolve 6-chloro-5-iodo-2-methyl-pyrimidin-4-amine (20 g, 74.22 mmol), 4-ethynyl-piperidine-1-carboxylic acid tert-butyl ester (18.64 g, 89.06 mmol), and diisopropylamine (10.44 mL, 74.22 mmol) in THF (200 mL) in a 3-neck flask. Alternately evacuate and charge the flask with nitrogen three times. Add bis(triphenylphosphine)palladium(II) chloride (2.63 g, 3.71 mmol) and copper(I) iodide (0.713 g, 3.71 mmol) to the solution. Heat the mixture to 50-55° C. for 16 hours. Cool the mixture to room temperature and add more bis(triphenylphosphine)palladium(II) chloride (1.31 g, 1.86 mmol), copper(I) iodide (0.356 g, 1.86 mmol) and 4-ethynyl-piperidine-1-carboxylic acid tert-butyl ester (1.55 g, 7.42 mmol). Heat the mixture to 60° C. for 3.5 hours. Cool the reaction to room temperature and concentrate under reduced pressure. Dilute the mixture with DCM (300 mL) and wash with saturated aqueous ammonium chloride (100 mL), water (100 mL) and saturated aqueous sodium chloride (100 mL). Dry the organic solution over MgSO$_4$, filter, and concentrate under reduced pressure. Purify the residue by chromatography (800 g silica gel column) eluting with 20-100% EtOAc in hexane. Concentrate the purified fractions to give the title compound as a pale orange powder (22.6 g, 86%). LC-ES/MS m/z ($^{35}$Cl/$^{37}$Cl) 351.2/353.1 (M+H).

Preparation 5 tert-Butyl 4-[2-(4-amino-2-chloro-6-methyl-pyrimidin-5-yl)ethyl]piperidine-1-carboxylate

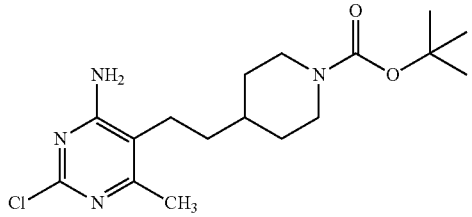 [SMILES: Cc1nc(Cl)nc(N)c1CCC1CCN(C(=O)OC(C)(C)C)CC1]

Combine tert-butyl 4-[2-(4-amino-2-chloro-6-methyl-pyrimidin-5-yl)ethynyl]piperidine-1-carboxylate (25.0 g, 71.26 mmol) and platinum(IV) oxide (2.0 g, 7.13 mmol) in EtOH (285 mL). Stir under 60 psi of hydrogen for 4 hours. Filter the reaction mixture through a plug of diatomaceous earth, rinse with EtOH and remove the solvent under reduced pressure. Dissolve the crude mixture with EtOH (285 mL) and add again platinum(IV) oxide (2.0 g, 7.13 mmol). Stir under 80 psi of hydrogen for 8 hours. Monitor the reaction carefully to avoid a potential side product resulting from removal of the 2-chloro. Filter the reaction mixture through a plug of diatomaceous earth washing with EtOH (250 mL) and remove solvent under reduced pressure. Purify the material using silica gel chromatography eluting with hexane/EtOAc (1:1). Combine the purified fractions and concentrate under reduced pressure to obtain the title compound as colorless oil (17 g, 67%). LC-ES/MS m/z ($^{35}$Cl/$^{37}$Cl) 355/357 (M+H), T$_R$=2.00 min, gradient program 2.

Preparation 6 tert-Butyl 4-[2-(4-amino-6-chloro-2-methyl-pyrimidin-5-yl)ethyl]piperidine-1-carboxylate

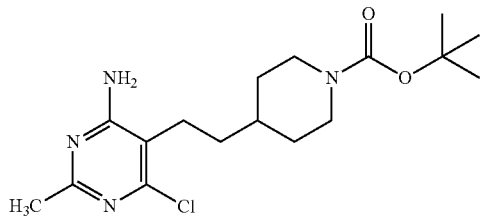 [SMILES: Cc1nc(N)c(CCC2CCN(C(=O)OC(C)(C)C)CC2)c(Cl)n1]

Combine tert-butyl 4-[2-(4-amino-6-chloro-2-methyl-pyrimidin-5-yl)ethynyl]piperidine-1-carboxylate (4.30 g, 12.26 mmol) and platinum(IV) oxide (0.139 g, 0.61 mmol) in EtOH (81 mL) and EtOAc (40 mL). Alternately evacuate and charge the flask with hydrogen (balloon pressure) and agitate at room temperature for 8 hours. Monitor the reaction carefully to avoid a potential side product resulting from removal of the chloride in the molecule. Note that the product is more soluble in the solvent mixture than the starting alkyne. Filter the mixture through a SPE cartridge (ISOLUTE® HM-N) rinsing with MeOH. Concentrate the solution under reduced pressure. Into the flask add silica 1-propanethiol (4 g, loading=1.28 mmol/g, SILIABOND® Thiol) to remove residual palladium from the previous coupling reaction and EtOAc (300 mL). Stir the material at room temperature for 3 days. Filter the solid and concentrate the filtrate under reduced pressure. Repeat the hydrogenation on the resulting residue as follows. Charge the flask containing the residue with platinum(IV) oxide (0.139 g, 0.61 mmol), EtOH (81 mL) and EtOAc (40 mL). Alternately evacuate and charge the flask with hydrogen using a hydrogen balloon and agitate at room temperature for 8 hours. Filter through diatomaceous earth, rinsing with MeOH, and concentrate the filtrate under reduced pressure. Repeat the hydrogenation on the resulting residue as follows. Charge the flask containing the residue with platinum(IV) oxide (0.139 g, 0.61 mmol), EtOH (81 mL) and EtOAc (40 mL). Alternately evacuate and charge the flask with hydrogen using a hydrogen balloon and agitate at room temperature for 8 hours. Filter through diatomaceous earth, rinsing with MeOH and concentrate the filtrate under reduced pressure onto silica gel (20 g). Purify the material by chromatography (120 g silica gel column) eluting with 70-100% EtOAc in hexane. Combine the purified fractions and concentrate under reduced pressure. Dilute the residue with DCM and hexane and concentrate under reduced pressure three times.

Dry the material under vacuum to obtain the title compound as a white solid (3.20 g, 73%). LC-ES/MS m/z ($^{35}$Cl/$^{37}$Cl) 355.2/357.2 (M+H).

Preparation 7

2-Chloro-6-methyl-5-[2-(4-piperidyl)ethyl]pyrimidin-4-amine

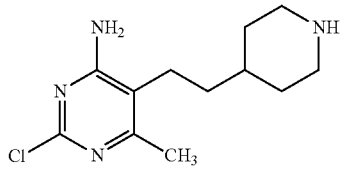 [SMILES: Cc1nc(Cl)nc(N)c1CCC1CCNCC1]

Dissolve tert-butyl 4-[2-(4-amino-2-chloro-6-methyl-pyrimidin-5-yl)ethyl]piperidine-1-carboxylate (5.0 g, 14.09 mmol) in 1,4-dioxane (141 mL) and add 4M hydrogen chloride in 1,4-dioxane (70.45 mL, 281.79 mmol). Stir the solution for 2 hours at room temperature. Concentrate the mixture under reduced pressure. Purify the material by SCX (50 g×5 columns) using 5 column volumes of MeOH and then 5 column volumes of 2N ammonia in MeOH to obtain the title compound (3.22 g, 90%). LC-ES/MS m/z ($^{35}$Cl/$^{37}$Cl) 255/257 (M+H), $T_R$=0.36 min, gradient program 2.

Preparation 8

6-Chloro-2-methyl-5-[2-(4-piperidyl)ethyl]pyrimidin-4-amine

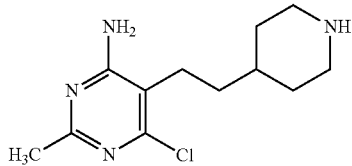

Dissolve tert-butyl 4-[2-(4-amino-6-chloro-2-methyl-pyrimidin-5-yl)ethyl]piperidine-1-carboxylate (3.2 g, 9.0 mmol) in DCM (60 mL). Add TFA (45 mL, 596.3 mmol) dropwise over 15 min and stir the solution at room temperature for 1 hour. Concentrate the reaction mixture under vacuum. Dissolve the resulting residue in MeOH (10 mL) and apply to a SCX column (50 g). Wash the column with water (100 mL), MeOH (100 mL) and elute the desired product with 2M ammonia in MeOH (400 mL). Concentrate under reduced pressure, azeotrope with 1:1 DCM/hexane (3×250 mL) and dry the resulting residue under reduced pressure to obtain the title compound as an off-white solid (2.23 g, 97%). LC-ES/MS m/z ($^{35}$Cl/$^{37}$Cl) 255.2/257.2 (M+H).

Preparation 9

6-Chloro-2-methyl-5-[2-(4-piperidyl)ethyl]pyrimidin-4-amine hydrochloride

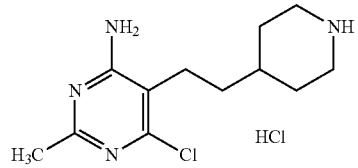

Dissolve tert-butyl 4-[2-(4-amino-6-chloro-2-methyl-pyrimidin-5-yl)ethyl]piperidine-1-carboxylate (29.0 g, 81.72 mmol) in 1,4-dioxane (145 mL) and add 4M hydrogen chloride in 1,4-dioxane (204.2 mL, 817.1 mmol). Stir the solution for 18 hours at room temperature. Concentrate the mixture under reduced pressure, slurry in diethyl ether (250 mL), filter, and dry the resultant solid under vacuum to give the title compound as a crude white solid (29 g) of sufficient purity for use without further purification. LC-ES/MS m/z ($^{35}$Cl/$^{37}$Cl) 255.2/257.2 (M+H).

Preparation 10 tert-Butyl N-[(1S)-2-[4-[2-(4-amino-2-chloro-6-methyl-pyrimidin-5-yl)ethyl]-1-piperidyl]-1-methyl-2-oxo-ethyl]carbamate

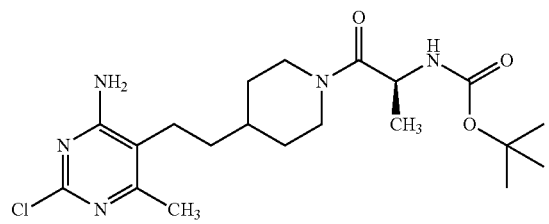 [SMILES: Cc1nc(Cl)nc(N)c1CCC1CCN(C(=O)[C@H](C)NC(=O)OC(C)(C)C)CC1]

Add TEA (5.25 mL, 37.68 mmol), 1-hydroxybenzotriazole (2.05 g, 15.07 mmol) and 1-(3-dimethylaminopropyl)-3-ethylcarbodiimide hydrochloride (2.89 g, 15.07 mmol) to a mixture of 2-chloro-6-methyl-5-[2-(4-piperidyl)ethyl]pyrimidin-4-amine (3.2 g, 12.56 mmol) and (2S)-2-(tert-butoxycarbonylamino)propanoic acid (2.85 g, 15.07 mmol) in DMF (63 mL). Stir the resulting mixture at room temperature overnight. Add water (50 mL) and extract with EtOAc (3×200 mL). Wash the organic layer with saturated aqueous sodium chloride (3×100 mL), dry over Na$_2$SO$_4$ and remove solvent under reduced pressure. Purify the material by chromatography, (silica gel) eluting with 20-80% EtOAc in hexane to obtain the title compound as a white solid (5.15 g, 96%). LC-ES/MS m/z ($^{35}$C/$^{37}$Cl) 426/428 (M+H), $T_R$=1.89 min, gradient program 1.

Preparation 11 tert-Butyl N-[2-[4-[2-(4-amino-6-chloro-2-methyl-pyrimidin-5-yl)ethyl]-1-piperidyl]-2-oxo-ethyl]carbamate

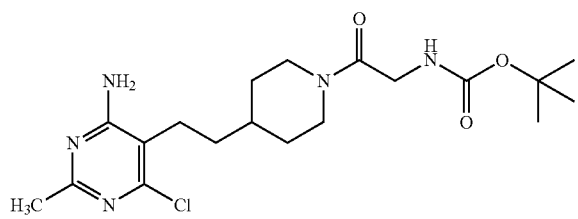 [SMILES: Cc1nc(N)c(CCC2CCN(C(=O)CNC(=O)OC(C)(C)C)CC2)c(Cl)n1]

Dissolve 6-chloro-2-methyl-5-[2-(4-piperidyl)ethyl]pyrimidin-4-amine (3.0 g, 11.78 mmol), N-(tert-butoxycarbonyl)glycine (2.29 g, 12.95 mmol), 1-hydroxy-7-azabenzotriazole (1.8 g, 2.95 mmol), 1-(3-dimethylaminopropyl)-3-ethylcarbodiimide hydrochloride (2.75 g, 14.13 mmol) and TEA (4.9 mL, 35.3 mmol) in THF (235 mL). Stir the resulting mixture at room temperature under nitrogen for 12 hours. Dilute the mixture with EtOAc (60 mL), water (10 mL) and stir for 10 min. Precharge a hydromatrix column (25 g) with EtOAc (40 mL) under atmospheric pressure, apply the reaction mixture to the hydromatrix column and allow mixture to stand for 10 min. Rinse column with EtOAc (3×20 mL) under low vacuum. Combine and concentrate all column eluents under reduced pressure. Purify the crude mixture by chromatography (330 g silica gel column) eluting with 0-10% MeOH in EtOAc and evaporate desired fractions. Azeotrope resulting solid with 1:1 DCM/hexane (3×100 mL) and dry under vacuum to obtain the title compound as a white solid (4.4 g, 91%). LC-ES/MS m/z ($^{35}$Cl/$^{37}$Cl) 412.3/414.3 (M+H).

Preparation 12

(2S)-2-Amino-1-[4-[2-(4-amino-2-chloro-6-methyl-pyrimidin-5-yl)ethyl]-1-piperidyl]propan-1-one dihydrochloride

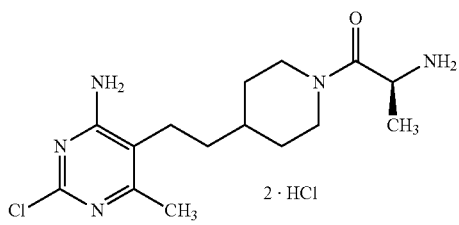 [SMILES: Cc1nc(Cl)nc(N)c1CCC1CCN(C(=O)[C@H](C)N)CC1]

Dissolve tert-butyl N-[(1S)-2-[4-[2-(4-amino-2-chloro-6-methyl-pyrimidin-5-yl)ethyl]-1-piperidyl]-1-methyl-2-oxo-ethyl]carbamate (5.15 g, 12.1 mmol) in 1,4-dioxane (121 mL). Add 4M hydrogen chloride in 1,4-dioxane (45.3 mL, 181.4 mmol) and stir for 3 hours at room temperature. Concentrate the mixture under reduced pressure to obtain the title compound as a white solid (4.63 g, 96%). LC-ES/MS m/z ($^{35}$Cl/$^{37}$Cl) 326/328 (M+H), $T_R$=1.39 min, gradient program 1.

Preparation 13

(2S)-2-Amino-1-[4-[2-(4-amino-6-chloro-2-methyl-pyrimidin-5-yl)ethyl]-1-piperidyl]propan-1-one

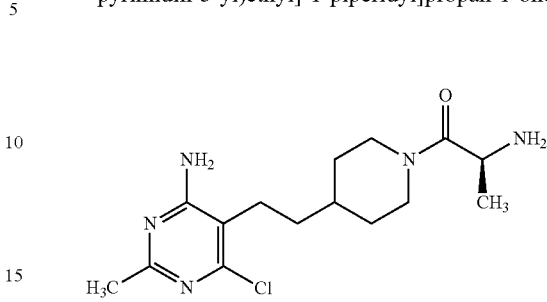

Dissolve tert-butyl N-[(1S)-2-[4-[2-(4-amino-6-chloro-2-methyl-pyrimidin-5-yl)ethyl]-1-piperidyl]-1-methyl-2-oxo-ethyl]carbamate (15.78 g, 37.05 mmol) in DCM (185 mL). Add TFA (185 mL) in a dropwise manner over 3 min and stir the solution overnight. Analyze the reaction by LC-MS (low pH) to show complete conversion. Slowly add MeOH (400 mL) due to exothermic mixing. Prewash three SCX columns (50 g) with water (20 mL) and then MeOH (20 mL). Divide the reaction mixture into three equal portions and load equally onto the SCX columns. Wash each column with water (40 mL), MeOH (40 mL) and elute the desired product with 2M ammonia in MeOH (60 mL). Concentrate under reduced pressure, azeotrope with DCM/hexane (1:1) three times, and place under vacuum to obtain the title compound as a white foam (10.29 g, 84%). LC-ES/MS m/z ($^{35}$Cl/$^{37}$Cl) 326.2/328.2 (M+H).

Preparation 14

(2S)-2-Amino-1-[4-[2-(4-amino-6-chloro-2-methyl-pyrimidin-5-yl)ethyl]-1-piperidyl]propan-1-one hydrochloride

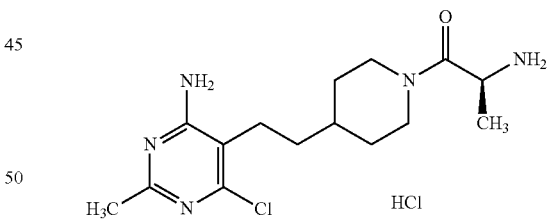

Dissolve tert-butyl N-[(1S)-2-[4-[2-(4-amino-6-chloro-2-methyl-pyrimidin-5-yl)ethyl]-1-piperidyl]-1-methyl-2-oxo-ethyl]carbamate (28.75 g, 67.49 mmol) in 1,4-dioxane (143.7 mL). Add 4M hydrogen chloride in 1,4-dioxane (168.7 mL, 674.9 mmol) and stir for 10 min. Add MeOH (20 mL) and stir the mixture for 3 hours with vigorous stirring. Concentrate the mixture under reduced pressure, dilute the solid with diethyl ether (200 mL) and stir overnight. Filter the material rinsing with diethyl ether (2×25 mL). Dry the material via suction for 15 min and then under vacuum for 1 hour at 45° C. to obtain the title compound as a crude white powder (27.7 g) of sufficient purity for use without further purification. LC-ES/MS m/z ($^{35}$Cl/$^{37}$Cl) 326.1/328.2 (M+H).

Preparation 15

2-Amino-1-[4-[2-(4-amino-6-chloro-2-methyl-pyrimidin-5-yl)ethyl]-1-piperidyl]ethanone

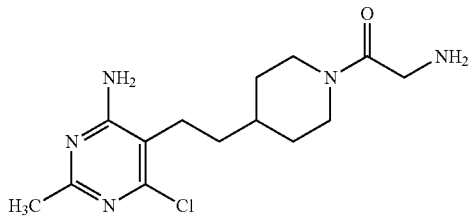 [SMILES: Cc1nc(N)c(CCC2CCN(C(=O)CN)CC2)c(Cl)n1]

Dissolve tert-butyl N-[2-[4-[2-(4-amino-6-chloro-2-methyl-pyrimidin-5-yl)ethyl]-1-piperidyl]-2-oxo-ethyl]carbamate (4.4 g, 10.68 mmol) in DCM (53.4 mL) and treat the resulting solution dropwise with TFA (53.4 mL, 706 mmol). Stir the solution for 2 hours and concentrate under vacuum. Dissolve the resulting residue in MeOH and apply to a SCX column (5 g, prewashed with 20 mL water and 20 mL MeOH). Wash the column with water (40 mL), MeOH (20 mL) and elute the desired product with 2M ammonia in MeOH (60 mL). Concentrate under reduced pressure to obtain a thick oil. Azeotrope with 1:1 DCM/hexane (3×100 mL) and dry resulting residue under vacuum to obtain the title compound as a crude off-white foam (3.8 g) of sufficient purity for use without further purification. LC-ES/MS m/z ($^{35}$Cl/$^{37}$Cl) 312.3/314.3 (M+H).

Preparation 16

(2S)-2-Amino-1-[4-[2-(4-amino-6-chloro-2-methyl-pyrimidin-5-yl)ethyl]-1-piperidyl]propan-1-one dihydrochloride

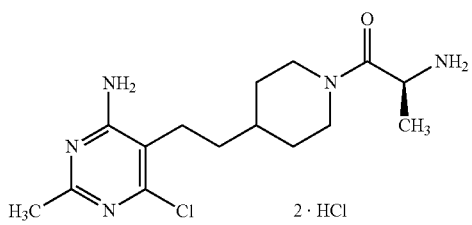 [SMILES: Cc1nc(N)c(CCC2CCN(C(=O)[C@H](C)N)CC2)c(Cl)n1]

Heat IPA (154 mL) to 50° C. and add acetyl chloride (19.3 mL, 271 mmol) slowly due to an exothermic reaction. Stir the reaction at 50° C. for 10 min and then add tert-butyl N-[(1S)-2-[4-[2-(4-amino-6-chloro-2-methyl-pyrimidin-5-yl)ethyl]-1-piperidyl]-1-methyl-2-oxo-ethyl]carbamate (21.0 g, 45.3 mmol). Stir the reaction for 2 hours monitoring via LC-MS (low pH). Cool the reaction to room temperature and add diethyl ether (386 mL). Stir the slurry for 15 min. Filter the solid washing with diethyl ether (2×50 mL) in a brisk manner as the material is hydroscopic. Filter the material, dry via filtration for 1 min and then in a vacuum drying oven at 50° C. overnight to give the title compound as a crude white powder (18.4 g) of sufficient purity for use without further purification. Counterion analysis by ion chromatography is consistent with the dihydrochloride salt. LC-ES/MS m/z ($^{35}$Cl/$^{37}$Cl) 326.1/328.2 (M+H).

Preparation 17

6-Chloro-2-methyl-5-(2-trimethylsilylethynyl)pyrimidin-4-amine

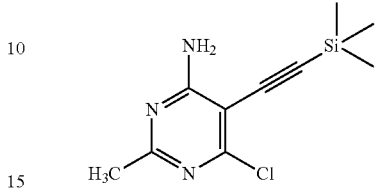

Add 6-chloro-5-iodo-2-methyl-pyrimidin-4-amine (128 g, 475 mmol) and TEA (2600 mL) to a 3-neck round bottom flask and degas for 10 min. Add copper(I) iodide (4.5 g, 23.63 mmol) and bis(triphenylphosphine)palladium(II) chloride (8.3 g, 11.82 mmol) to obtain a yellow suspension. Heat the reaction mixture to 70° C. to get a clear solution and add (trimethylsilyl)acetylene (73 mL, 518 mmol) in 60 min. Stir the solution at 70° C. for 6.5 hours. Cool the mixture to room temperature, filter the solid over diatomaceous earth and wash with EtOAc (3×200 mL). Concentrate under reduced pressure. Dissolve the residue in EtOAc (1.5 L), wash with 5% ammonium hydroxide (3×200 mL) and saturated aqueous sodium chloride (3×200 mL). Dry the organic phase over Na$_2$SO$_4$, filter and concentrate under reduced pressure. Slurry with pentane (300 mL) to obtain the title compound as a yellow solid (92 g, 81%). LC-ES/MS m/z ($^{35}$Cl/$^{37}$Cl) 240/242 (M+H).

Preparation 18

6-Chloro-5-ethynyl-2-methyl-pyrimidin-4-amine

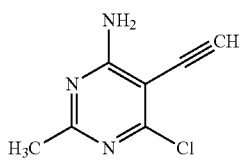

Dissolve 6-chloro-2-methyl-5-(2-trimethylsilylethynyl)pyrimidin-4-amine (92 g, 383.6 mmol) in THF (900 mL) in a 3-neck round bottom flask. Add water (300 mL) and 0.1M sodium hydroxide (38 mL, 3.8 mmol) dropwise in 10 min to give a brown solution. Stir the reaction mixture at room temperature for 30 min. Add ethyl acetate (1 L) and wash with saturated aqueous sodium chloride (1 L). Dry the organic phase over Na$_2$SO$_4$, filter and concentrate under reduced pressure to obtain the title compound as a yellow solid (63 g, 98%). LC-ES/MS m/z ($^{35}$Cl/$^{37}$Cl) 168/170 (M+H).

Preparation 19 tert-Butyl 4-(trifluoromethylsulfonyloxy)-2,3,6,7-tetrahydroazepine-1-carboxylate

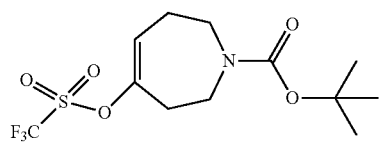

Add lithium hexamethyldisilazide (1M solution in THF, 32.33 mL, 32.33 mmol) dropwise under nitrogen to a solution of tert-butyl 4-oxoazepane-1-carboxylate (5 g, 23.09 mmol) in THF (15 mL) at −78° C. Add a solution of N-phenylbis(trifluoromethane-sulphonimide) (10.72 g, 30.02 mmol) in THF (15 mL) dropwise. Stir the reaction mixture at −78° C. for 1 hour, warm up the reaction to room temperature and stir at this temperature for 1 hour. Cool to 0° C. and quench with water. Add EtOAc, separate the organic phase and wash with saturated aqueous sodium chloride. Dry over Na$_2$SO$_4$, filter and concentrate under reduced pressure. Purify the crude mixture by chromatography (120 g silica gel column) eluting with 0-20% EtOAc in hexane to obtain the title compound (7.9 g, 99%). LC-ES/MS m/z ($^{35}$Cl/$^{37}$Cl) 259/261 (M+H).

Preparation 20 tert-Butyl 4-[2-(4-amino-6-chloro-2-methyl-pyrimidin-5-yl)ethynyl]-2,3,6,7-tetrahydroazepine-1-carboxylate

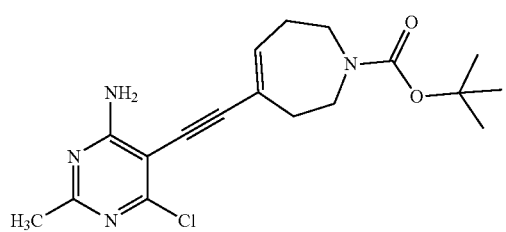 [SMILES: Cc1nc(N)c(C#CC2=CCCN(C(=O)OC(C)(C)C)CC2)c(Cl)n1]

Combine tert-butyl 4-(trifluoromethylsulfonyloxy)-2,3,6,7-tetrahydroazepine-1-carboxylate (11 g, 22.3 mmol), 6-chloro-5-ethynyl-2-methyl-pyrimidin-4-amine (4.48 g, 26.76 mmol), bis(triphenylphosphine)palladium(II) chloride (1.57 g, 2.23 mmol), copper(I) iodide (212 mg, 1.11 mmol), TEA (6.2 mL, 44.59 mmol) and DMF (223 mL) under nitrogen. Stir the mixture at 90° C. overnight. Filter the reaction mixture through a plug of diatomaceous earth rising with EtOAc. Wash the filtrate with saturated aqueous sodium chloride. Dry over Na$_2$SO$_4$, filter and concentrate under reduced pressure. Purify the crude mixture by chromatography (330 g silica gel column) eluting with 0-40% acetone in hexane to obtain the title compound (4.75 g, 59%). LC-ES/MS m/z ($^{35}$Cl/$^{37}$Cl) 363/365 (M+H).

Preparation 21 tert-Butyl (4R,S)-4-[2-(4-amino-6-chloro-2-methyl-pyrimidin-5-yl)ethyl]azepane-1-carboxylate

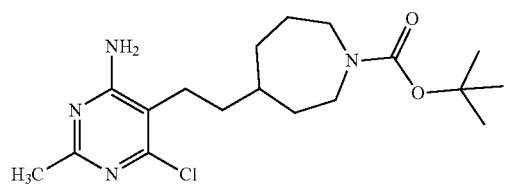 [SMILES: Cc1nc(N)c(CCC2CCCN(C(=O)OC(C)(C)C)CC2)c(Cl)n1]

Dissolve tert-butyl 4-[2-(4-amino-6-chloro-2-methyl-pyrimidin-5-yl)ethynyl]-2,3,6,7-tetrahydroazepine-1-carboxylate (3.2 g, 8.82 mmol) in EtOH (176 mL). Add platinum dioxide (40 mg, 0.172 mmol) and stir the resulting mixture under hydrogen at atmospheric pressure for 5 hours. Filter the mixture through a plug of diatomaceous earth. Remove the solvent under reduced pressure and purify the crude mixture by chromatography (80 g silica gel column) eluting with 0-40% acetone in hexane to obtain the title compound (2.8 g, 85%). LC-ES/MS m/z ($^{35}$Cl/$^{37}$Cl) 369/371 (M+H).

Preparation 22

5-[2-[(4R,S)-Azepan-4-yl]ethyl]-6-chloro-2-methyl-pyrimidin-4-amine

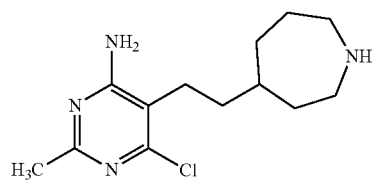 [SMILES: Cc1nc(N)c(CCC2CCCNCC2)c(Cl)n1]

Dissolve tert-butyl (4R,S)-4-[2-(4-amino-6-chloro-2-methyl-pyrimidin-5-yl)ethyl]azepane-1-carboxylate (2.8 g, 7.59 mmol) in 1,4-dioxane (76 mL) and add 4M hydrogen chloride in 1,4-dioxane (38 mL, 152 mmol). Stir the solution at room temperature for 8 hours. Concentrate the mixture under reduced pressure. Dissolve the residue in MeOH and apply it to a SCX column (3×25 g). Wash the column with MeOH and elute the desired product with 2M ammonia in MeOH. Concentrate under reduced pressure to give the title compound as a crude foam (2.04 g) of sufficient purity for use without further purification. LC-ES/MS m/z ($^{35}$Cl/$^{37}$Cl) 269/271 (M+H).

Preparation 23

(2S)-2-Amino-1-[(4R,S)-4-[2-(4-amino-6-chloro-2-methyl-pyrimidin-5-yl)ethyl]azepan-1-yl]propan-1-one

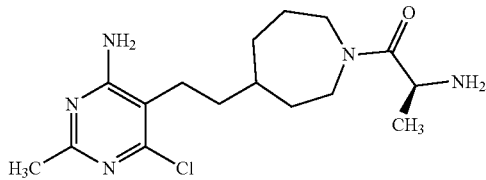 [SMILES: Cc1nc(N)c(CCC2CCCN(C(=O)[C@H](C)N)CC2)c(Cl)n1]

Dissolve tert-butyl N-[(1S)-2-[(4R,S)-4-[2-(4-amino-6-chloro-2-methyl-pyrimidin-5-yl)ethyl]azepan-1-yl]-1-methyl-2-oxo-ethyl]carbamate (2.40 g, 5.45 mmol) in 1,4-dioxane (55 mL). Add 4M hydrogen chloride in 1,4-dioxane (41 mL, 163.6 mmol) and stir at room temperature overnight. Concentrate the mixture under reduced pressure. Dissolve the resulting residue in MeOH and apply to a SCX column (50 g). Wash the column with MeOH and elute the desired product with 2M ammonia in MeOH. Concentrate under reduced pressure to obtain the title compound (1.75 g, 94%) with sufficient purity for use without further purification. LC-ES/MS m/z ($^{35}$Cl/$^{37}$Cl) 340/342 (M+H).

Example 1

N-[(1S)-2-[4-[2-(4-amino-2-chloro-6-methyl-pyrimidin-5-yl)ethyl]-1-piperidyl]-1-methyl-2-oxo-ethyl]-2-methyl-pyrazole-3-carboxamide

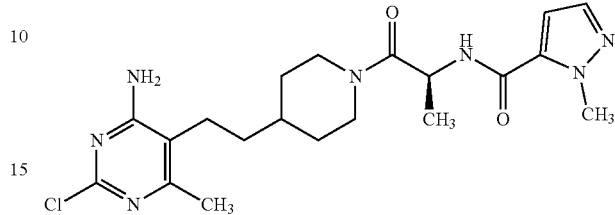

Add (2S)-2-amino-1-[4-[2-(4-amino-2-chloro-6-methyl-pyrimidin-5-yl)ethyl]-1-piperidyl]propan-1-one dihydrochloride (150 mg, 0.38 mmol), 1-methyl-1H-pyrazole-5-carboxylic acid (52 mg, 0.41 mmol), THF (7.5 mL) and TEA (0.31 mL, 2.26 mmol). Stir the mixture for 5 min and add 1-hydroxybenzotriazole (61 mg, 0.45 mmol) and 1-(3-dimethylaminopropyl)-3-ethylcarbodiimide hydrochloride (87 mg, 0.45 mmol). Stir the reaction at room temperature overnight. Add water (20 mL) and extract with EtOAc (3×50 mL). Wash the organic phase with saturated aqueous sodium chloride (3×30 mL), dry over $Na_2SO_4$, filter and concentrate under reduced pressure. Dissolve the crude mixture into a minimal amount of DCM and filter through a SPE cartridge (20 g silica) eluting with 50-100% acetone in hexane. Purify the crude mixture by mass-guided SFC [Waters SFC-MS Prep 100; 30×150 mm 2-ethylpyridine column; 5µ particle size; $CO_2$ (A)/MeOH (B) as mobile phase; isocratic mode (10% B for 1 min, gradient from 10-20% B in 3 min, from 20-40% B in 0.5 min, 1 min wash step at 40% B and back to initial conditions in 0.5 min); flow rate 100 mL/min] to obtain the title compound as a white solid (90 mg, 55%). LC-ES/MS m/z ($^{35}$Cl/$^{37}$Cl) 434/436 (M+H), $T_R$=1.39 min, gradient program 2.

Prepare examples 2-41 essentially as described in Example 1 using the corresponding amine intermediate and the appropriately substituted carboxylic acid. LC-ES/MS data are included in Table 1 below.

TABLE 1

| Ex No. | Chemical Name | Structure | LC-ES/MS m/z ($^{35}$Cl/$^{37}$Cl) |
|---|---|---|---|
| 2 | N-[(1S)-2-[4-[2-(4-Amino-2-chloro-6-methyl-pyrimidin-5-yl)ethyl]-1-piperidyl]-1-methyl-2-oxo-ethyl]-5-methyl-1H-pyrazole-4-carboxamide | 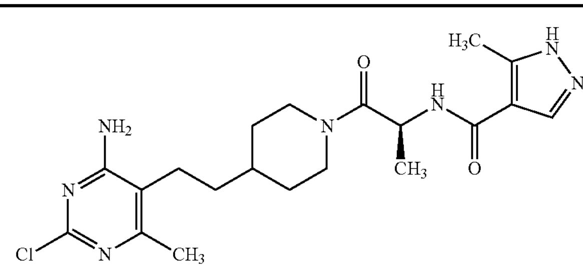 | 434/436 (M + H) |

TABLE 1-continued

| Ex No. | Chemical Name | Structure | LC-ES/MS m/z ($^{35}$Cl/$^{37}$Cl) |
|---|---|---|---|
| 3 | N-[(1S)-2-[4-[2-(4-Amino-2-chloro-6-methyl-pyrimidin-5-yl)ethyl]-1-piperidyl]-1-methyl-2-oxo-ethyl]-1-methyl-pyrazole-4-carboxamide | 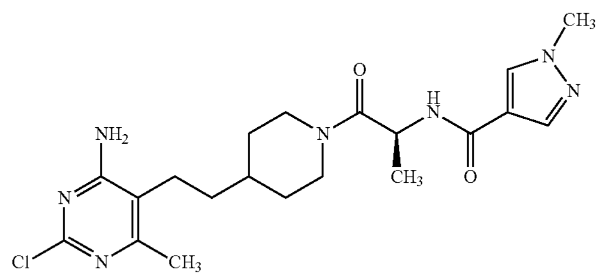 [SMILES: Cc1nc(Cl)nc(N)c1CCC1CCN(C(=O)[C@H](C)NC(=O)c2cnn(C)c2)CC1] | 434/436 (M + H) |
| 4 | N-[(1S)-2-[4-[2-(4-Amino-2-chloro-6-methyl-pyrimidin-5-yl)ethyl]-1-piperidyl]-1-methyl-2-oxo-ethyl]-1-ethyl-pyrazole-4-carboxamide | 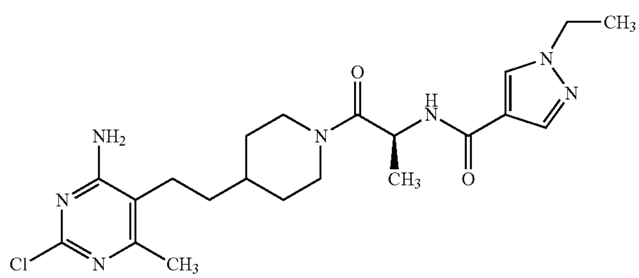 [SMILES: CCn1cc(C(=O)N[C@@H](C)C(=O)N2CCC(CCc3c(C)nc(Cl)nc3N)CC2)cn1] | 448/450 (M + H) |
| 5 | N-[(1S)-2-[4-[2-(4-Amino-2-chloro-6-methyl-pyrimidin-5-yl)ethyl]-1-piperidyl]-1-methyl-2-oxo-ethyl]-2-methyl-thiazole-5-carboxamide | 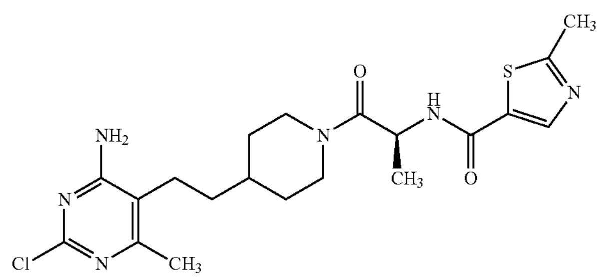 [SMILES: Cc1ncc(C(=O)N[C@@H](C)C(=O)N2CCC(CCc3c(C)nc(Cl)nc3N)CC2)s1] | 451/453 (M + H) |
| 6 | N-[(1S)-2-[4-[2-(4-Amino-2-chloro-6-methyl-pyrimidin-5-yl)ethyl]-1-piperidyl]-1-methyl-2-oxo-ethyl]-2-methyl-thiazole-4-carboxamide | 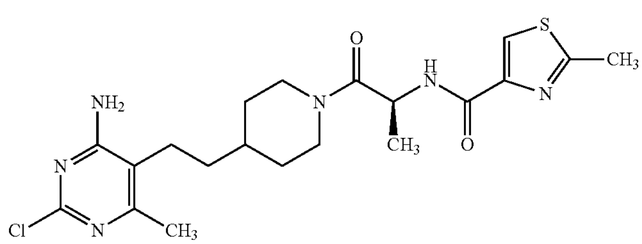 | 451/453 (M + H) |
| 7 | N-[(1S)-2-[4-[2-(4-Amino-2-chloro-6-methyl-pyrimidin-5-yl)ethyl]-1-piperidyl]-1-methyl-2-oxo-2-ethyl]-2-methyl-oxazole-4-carboxamide | 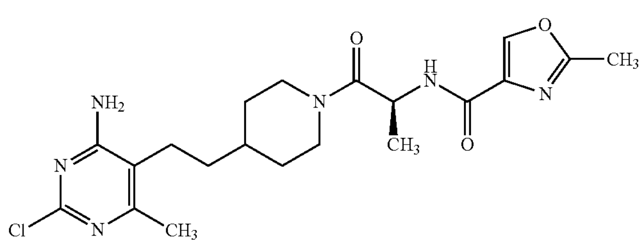 | 435/437 (M + H) |

TABLE 1-continued

| Ex No. | Chemical Name | Structure | LC-ES/MS m/z ($^{35}$Cl/$^{37}$Cl) |
|---|---|---|---|
| 8 | N-[(1S)-2-[4-[2-(4-Amino-2-chloro-6-methyl-pyrimidin-5-yl)ethyl]-1-piperidyl]-1-methyl-2-oxo-ethyl]pyridine-3-carboxamide | 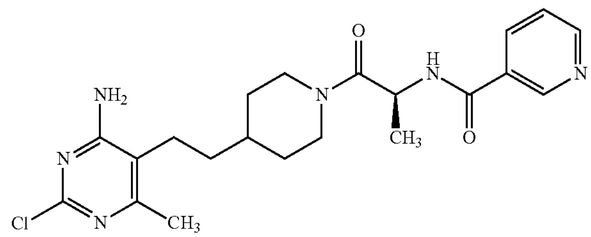 [SMILES: Cc1nc(Cl)nc(N)c1CCC1CCN(C(=O)[C@H](C)NC(=O)c2cccnc2)CC1] | 431/433 (M + H) |
| 9 | N-[(1S)-2-[4-[2-(4-Amino-2-chloro-6-methyl-pyrimidin-5-yl)ethyl]-1-piperidyl]-1-methyl-2-oxo-ethyl]pyridazine-3-carboxamide | 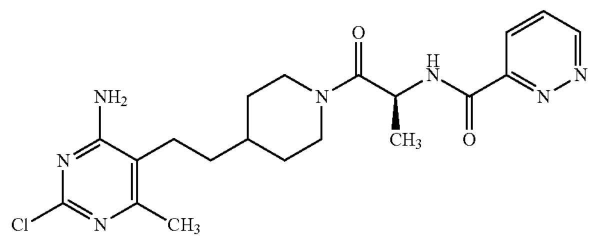 [SMILES: Cc1nc(Cl)nc(N)c1CCC1CCN(C(=O)[C@H](C)NC(=O)c2cccnn2)CC1] | 432/434 (M + H) |
| 10 | N-[(1S)-2-[4-[2-(4-Amino-2-chloro-6-methyl-pyrimidin-5-yl)ethyl]-1-piperidyl]-1-methyl-2-oxo-ethyl]-2-methoxy-benzamide | 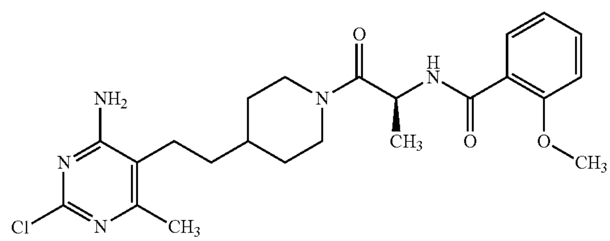 [SMILES: COc1ccccc1C(=O)N[C@@H](C)C(=O)N1CCC(CCc2c(C)nc(Cl)nc2N)CC1] | 460/462 (M + H) |
| 11 | N-[(1S)-2-[4-[2-(4-Amino-2-chloro-6-methyl-pyrimidin-5-yl)ethyl]-1-piperidyl]-1-methyl-2-oxo-ethyl]-3-methoxy-benzamide | 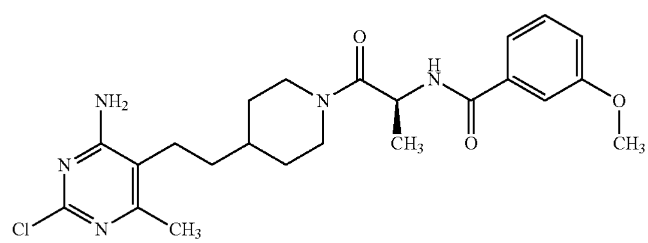 [SMILES: COc1cccc(C(=O)N[C@@H](C)C(=O)N2CCC(CCc3c(C)nc(Cl)nc3N)CC2)c1] | 460/462 (M + H) |
| 12 | N-[(1S)-2-[4-[2-(4-Amino-2-chloro-6-methyl-pyrimidin-5-yl)ethyl]-1-piperidyl]-1-methyl-2-oxo-ethyl]-4-methoxy-benzamide | 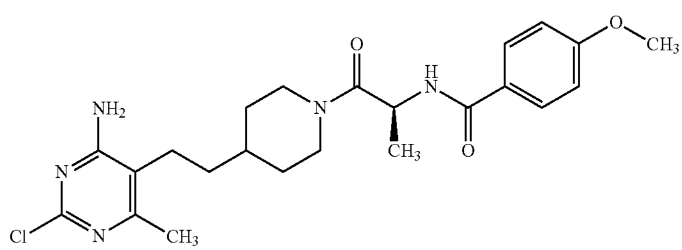 [SMILES: COc1ccc(C(=O)N[C@@H](C)C(=O)N2CCC(CCc3c(C)nc(Cl)nc3N)CC2)cc1] | 460/462 (M + H) |
| 13 | N-[(1S)-2-[4-[2-(4-Amino-2-chloro-6-methyl-pyrimidin-5-yl)ethyl]-1-piperidyl]-1-methyl-2-oxo-ethyl]cyclopropane-carboxamide | 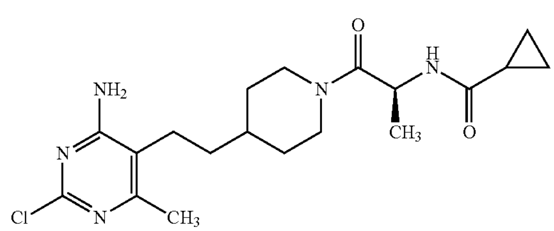 [SMILES: Cc1nc(Cl)nc(N)c1CCC1CCN(C(=O)[C@H](C)NC(=O)C2CC2)CC1] | 394/396 (M + H) |

TABLE 1-continued

| Ex No. | Chemical Name | Structure | LC-ES/MS m/z ($^{35}$Cl/$^{37}$Cl) |
|---|---|---|---|
| 14 | N-[(1S)-2-[4-[2-(4-Amino-2-chloro-6-methyl-pyrimidin-5-yl) ethyl]-1-piperidyl]-1-methyl-2-oxo-ethyl]-2-hydroxy-acetamide | 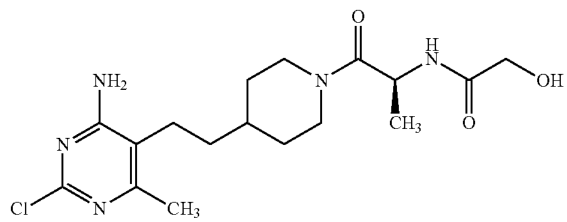 [SMILES: Cc1nc(Cl)nc(N)c1CCC1CCN(C(=O)[C@H](C)NC(=O)CO)CC1] | 384/386 (M + H) |
| 15 | (2R)-N-[(1S)-2-[4-[2-(4-Amino-2-chloro-6-methyl-pyrimidin-5-yl)ethyl]-1-piperidyl]-1-methyl-2-oxo-ethyl]-2-hydroxy-propanamide | 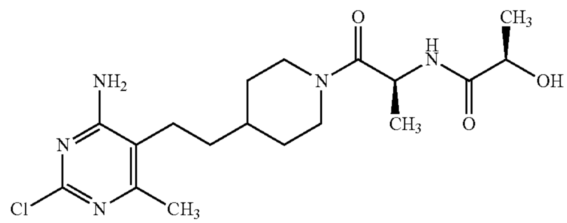 [SMILES: Cc1nc(Cl)nc(N)c1CCC1CCN(C(=O)[C@H](C)NC(=O)[C@@H](C)O)CC1] | 398/400 (M + H) |
| 16 | N-[(1S)-2-[4-[2-(4-Amino-6-chloro-2-methyl-pyrimidin-5-yl) ethyl]-1-piperidyl]-1-methyl-2-oxo-ethyl]-2,5-dimethyl-pyrazole-3-carboxamide | 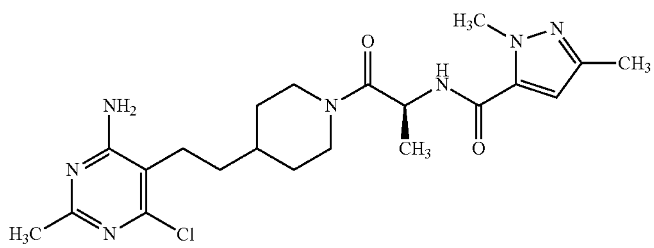 | 451/453 (M + H) |
| 17 | N-[(1S)-2-[4-[2-(4-Amino-6-chloro-2-methyl-pyrimidin-5-yl) ethyl]-1-piperidyl]-1-methyl-2-oxo-ethyl]-2-methyl-oxazole-4-carboxamide | 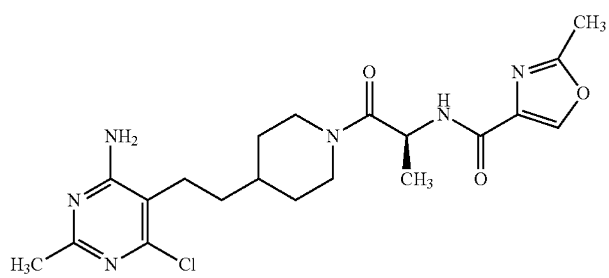 [SMILES: Cc1nc(N)c(CCC2CCN(C(=O)[C@H](C)NC(=O)c3coc(C)n3)CC2)c(Cl)n1] | 435/437 (M + H) |
| 18 | N-[(1S)-2-[4-[2-(4-Amino-6-chloro-2-methyl-pyrimidin-5-yl) ethyl]-1-piperidyl]-1-methyl-2-oxo-ethyl] thiadiazole-4-carboxamide | 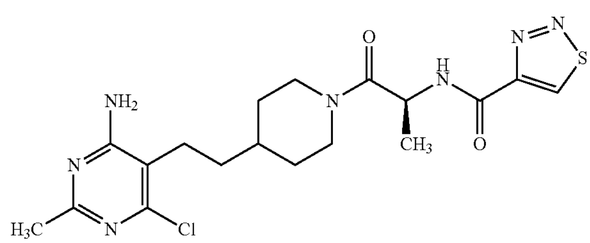 [SMILES: Cc1nc(N)c(CCC2CCN(C(=O)[C@H](C)NC(=O)c3csnn3)CC2)c(Cl)n1] | 438/440 (M + H) |
| 19 | N-[(1S)-2-[4-[2-(4-Amino-6-chloro-2-methyl-pyrimidin-5-yl) ethyl]-1-piperidyl]-1-methyl-2-oxo-ethyl]-3-methyl-1H-pyrazole-4-carboxamide | 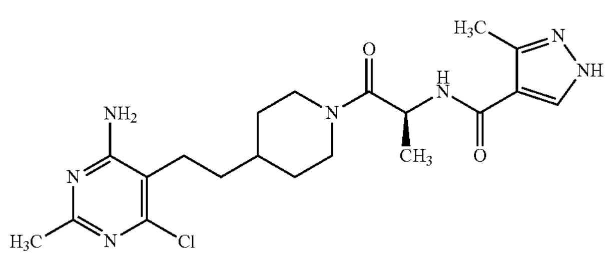 [SMILES: Cc1nc(N)c(CCC2CCN(C(=O)[C@H](C)NC(=O)c3c[nH]nc3C)CC2)c(Cl)n1] | 434/436 (M + H) |

TABLE 1-continued

| Ex No. | Chemical Name | Structure | LC-ES/MS m/z ($^{35}$Cl/$^{37}$Cl) |
|---|---|---|---|
| 20 | N-[(1S)-2-[4-[2-(4-Amino-6-chloro-2-methyl-pyrimidin-5-yl)ethyl]-1-piperidyl]-1-methyl-2-oxo-ethyl]-1,5-dimethyl-pyrazole-4-carboxamide | 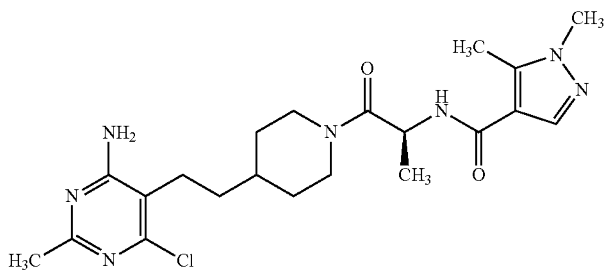 | 451/453 (M + H) |
| 21 | N-[(1S)-2-[4-[2-(4-Amino-6-chloro-2-methyl-pyrimidin-5-yl)ethyl]-1-piperidyl]-1-methyl-2-oxo-ethyl]-1-ethyl-pyrazole-4-carboxamide | 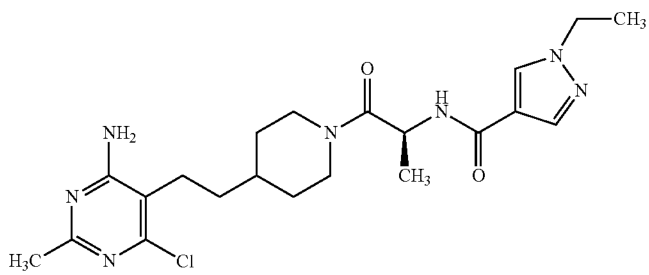 [SMILES: CCn1cc(C(=O)N[C@@H](C)C(=O)N2CCC(CCc3c(N)nc(C)nc3Cl)CC2)cn1] | 448/450 (M + H) |
| 22 | N-[(1S)-2-[4-[2-(4-Amino-6-chloro-2-methyl-pyrimidin-5-yl)ethyl]-1-piperidyl]-1-methyl-2-oxo-ethyl]-1,3-dimethyl-pyrazole-4-carboxamide | 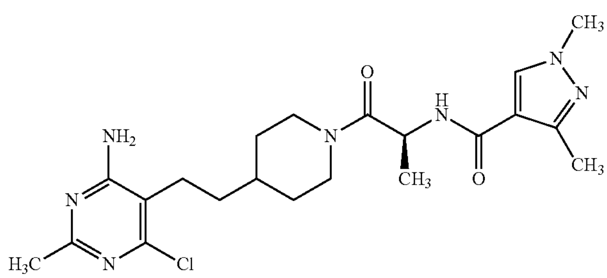 [SMILES: Cc1nc(N)c(CCC2CCN(C(=O)[C@H](C)NC(=O)c3cn(C)nc3C)CC2)c(Cl)n1] | 448/450 (M + H) |
| 23 | N-[(1S)-2-[4-[2-(4-Amino-6-chloro-2-methyl-pyrimidin-5-yl)ethyl]-1-piperidyl]-1-methyl-2-oxo-ethyl]-2-ethyl-pyrazole-3-carboxamide | 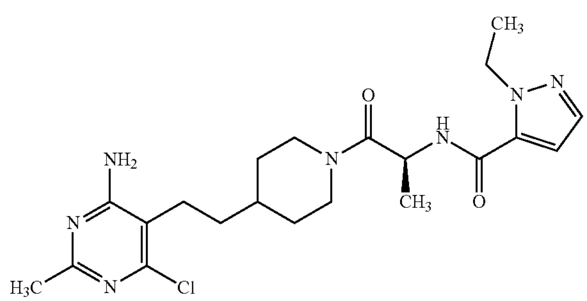 [SMILES: CCn1nccc1C(=O)N[C@@H](C)C(=O)N1CCC(CCc2c(N)nc(C)nc2Cl)CC1] | 448/450 (M + H) |
| 24 | N-[(1S)-2-[4-[2-(4-Amino-6-chloro-2-methyl-pyrimidin-5-yl)ethyl]-1-piperidyl]-1-methyl-2-oxo-ethyl]-1-methyl-pyrazole-3-carboxamide | 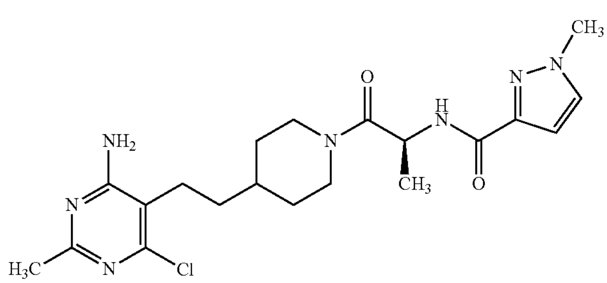 [SMILES: Cc1nc(N)c(CCC2CCN(C(=O)[C@H](C)NC(=O)c3ccn(C)n3)CC2)c(Cl)n1] | 434/436 (M + H) |

TABLE 1-continued

| Ex No. | Chemical Name | Structure | LC-ES/MS m/z ($^{35}$Cl/$^{37}$Cl) |
|---|---|---|---|
| 25 | N-[(1S)-2-[4-[2-(4-Amino-6-chloro-2-methyl-pyrimidin-5-yl)ethyl]-1-piperidyl]-1-methyl-2-oxo-ethyl]butanamide | 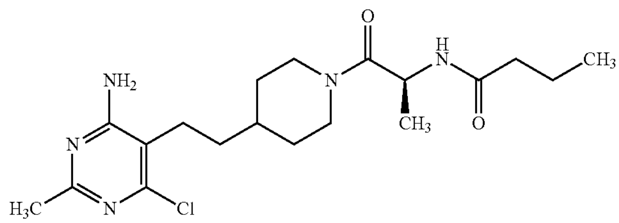 [SMILES: CCCC(=O)N[C@@H](C)C(=O)N1CCC(CCc2c(N)nc(C)nc2Cl)CC1] | 396/398 (M + H) |
| 26 | N-[(1S)-2-[4-[2-(4-Amino-6-chloro-2-methyl-pyrimidin-5-yl)ethyl]-1-piperidyl]-1-methyl-2-oxo-ethyl]-3,3,3-trifluoro-propanamide | 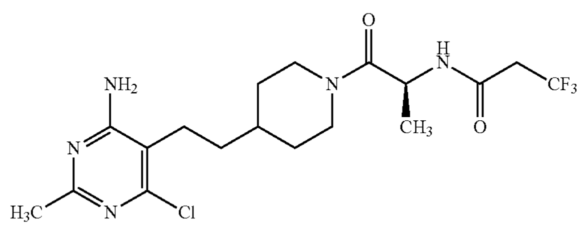 [SMILES: Cc1nc(N)c(CCC2CCN(C(=O)[C@H](C)NC(=O)CC(F)(F)F)CC2)c(Cl)n1] | 436/438 (M + H) |
| 27 | N-[(1S)-2-[(4R,S)-4-[2-(4-Amino-6-chloro-2-methyl-pyrimidin-5-yl)ethyl]azepan-1-yl]-1-methyl-2-oxo-ethyl]-2-methyl-oxazole-4-carboxamide | 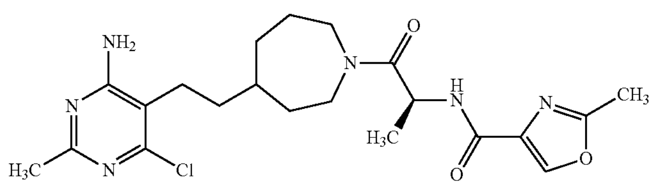 | 449/451 (M + H) |
| 28 | N-[(1S)-2-[(4R,S)-4-[2-(4-Amino-6-chloro-2-methyl-pyrimidin-5-yl)ethyl]azepan-1-yl]-1-methyl-2-oxo-ethyl]-2-methyl-thiazole-4-carboxamide | 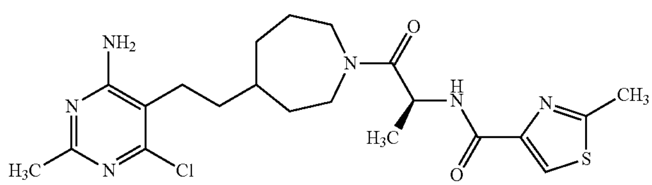 | 465/467 (M + H) |
| 29 | N-[(1S)-2-[(4R,S)-4-[2-(4-Amino-6-chloro-2-methyl-pyrimidin-5-yl)ethyl]azepan-1-yl]-1-methyl-2-oxo-ethyl]-2-methyl-thiazole-5-carboxamide | 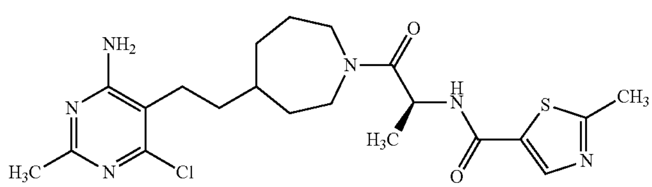 | 465/467 (M + H) |
| 30 | N-[(1S)-2-[(4R,S)-4-[2-(4-Amino-6-chloro-2-methyl-pyrimidin-5-yl)ethyl]azepan-1-yl]-1-methyl-2-oxo-ethyl]-1,5-dimethyl-pyrazole-4-carboxamide | 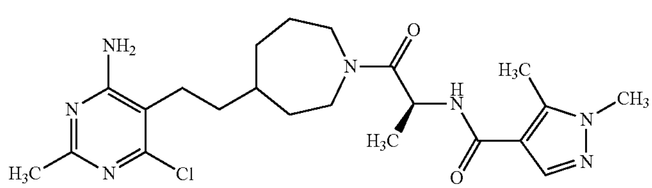 | 462/464 (M + H) |
| 31 | N-[(1S)-2-[(4R,S)-4-[2-(4-Amino-6-chloro-2-methyl-pyrimidin-5-yl)ethyl]azepan-1-yl]-1-methyl-2-oxo-ethyl]-1,3-dimethyl-pyrazole-4-carboxamide | 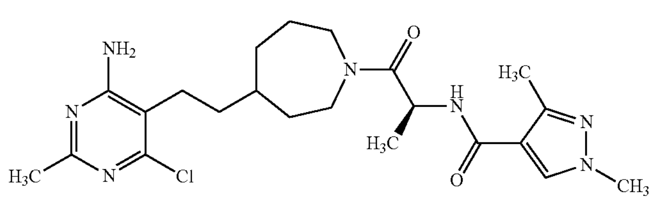 | 462/464 (M + H) |

TABLE 1-continued

| Ex No. | Chemical Name | Structure | LC-ES/MS m/z ($^{35}$Cl/$^{37}$Cl) |
|---|---|---|---|
| 32 | N-[(1S)-2-[(4R,S)-4-[2-(4-Amino-6-chloro-2-methyl-pyrimidin-5-yl)ethyl]azepan-1-yl]-1-methyl-2-oxo-ethyl]-1-methyl-pyrazole-3-carboxamide | 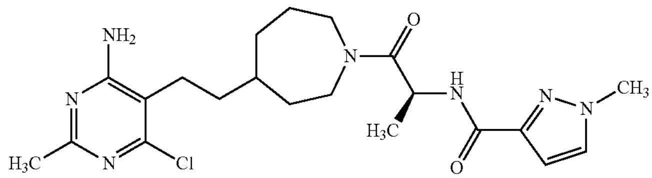 | 448/450 (M + H) |
| 33 | N-[(1S)-2-[(4R,S)-4-[2-(4-Amino-6-chloro-2-methyl-pyrimidin-5-yl)ethyl]azepan-1-yl]-1-methyl-2-oxo-ethyl]-1-methyl-pyrazole-4-carboxamide | 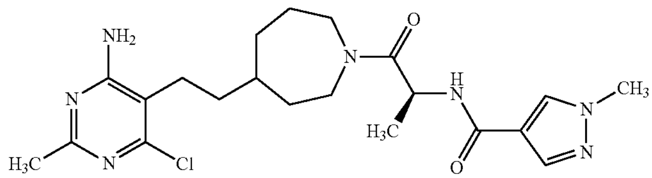 | 448/450 (M + H) |
| 34 | N-[(1S)-2-[(4R,S)-4-[2-(4-Amino-6-chloro-2-methyl-pyrimidin-5-yl)ethyl]azepan-1-yl]-1-methyl-2-oxo-ethyl]-2-methyl-pyrazole-3-carboxamide | 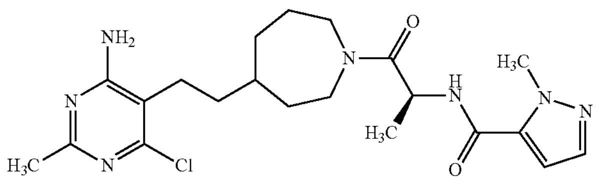 [SMILES: Cc1nc(N)c(CCC2CCCN(C(=O)[C@H](C)NC(=O)c3ccnn3C)CC2)c(Cl)n1] | 448/450 (M + H) |
| 35 | N-[(1S)-2-[(4R,S)-4-[2-(4-Amino-6-chloro-2-methyl-pyrimidin-5-yl)ethyl]azepan-1-yl]-1-methyl-2-oxo-ethyl]pyridine-2-carboxamide | 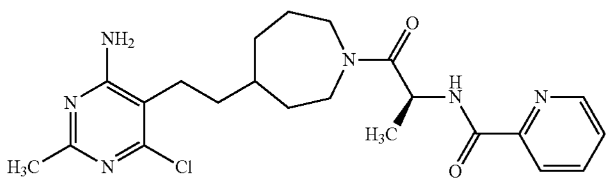 [SMILES: Cc1nc(N)c(CCC2CCCN(C(=O)[C@H](C)NC(=O)c3ccccn3)CC2)c(Cl)n1] | 445/447 (M + H) |
| 36 | N-[(1S)-2-[(4R,S)-4-[2-(4-Amino-6-chloro-2-methyl-pyrimidin-5-yl)ethyl]azepan-1-yl]-1-methyl-2-oxo-ethyl]pyridine-3-carboxamide | 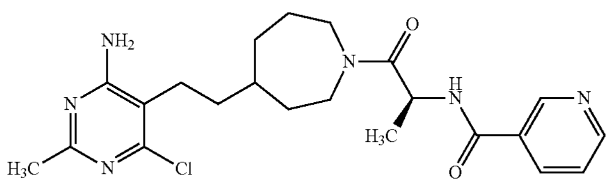 [SMILES: Cc1nc(N)c(CCC2CCCN(C(=O)[C@H](C)NC(=O)c3cccnc3)CC2)c(Cl)n1] | 445/447 (M + H) |
| 37 | N-[(1S)-2-[(4R,S)-4-[2-(4-Amino-6-chloro-2-methyl-pyrimidin-5-yl)ethyl]azepan-1-yl]-1-methyl-2-oxo-ethyl]pyridine-4-carboxamide | 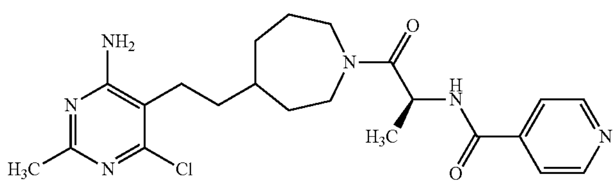 [SMILES: Cc1nc(N)c(CCC2CCCN(C(=O)[C@H](C)NC(=O)c3ccncc3)CC2)c(Cl)n1] | 445/447 (M + H) |
| 38 | N-[(1S)-2-[(4R,S)-4-[2-(4-Amino-6-chloro-2-methyl-pyrimidin-5-yl)ethyl]azepan-1-yl]-1-methyl-2-oxo-ethyl]pyridazine-3-carboxamide | 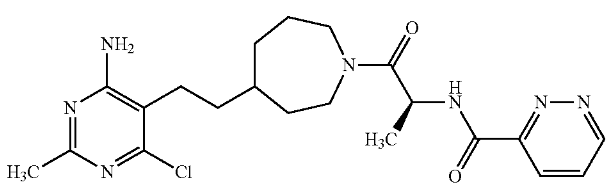 [SMILES: Cc1nc(N)c(CCC2CCCN(C(=O)[C@H](C)NC(=O)c3cccnn3)CC2)c(Cl)n1] | 446/448 (M + H) |
| 39 | N-[(1S)-2-[(4R,S)-4-[2-(4-Amino-6-chloro-2-methyl-pyrimidin-5-yl)ethyl]azepan-1-yl]-1-methyl-2-oxo-ethyl]-2-methoxy-benzamide | 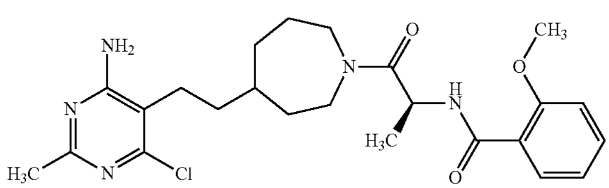 [SMILES: COc1ccccc1C(=O)N[C@@H](C)C(=O)N1CCCC(CCc2c(N)nc(C)nc2Cl)CC1] | 474/476 (M + H) |

TABLE 1-continued

| Ex No. | Chemical Name | Structure | LC-ES/MS m/z ($^{35}Cl/^{37}Cl$) |
|---|---|---|---|
| 40 | N-[(1S)-2-[(4R,S)-4-[2-(4-Amino-6-chloro-2-methyl-pyrimidin-5-yl)ethyl]azepan-1-yl]-1-methyl-2-oxo-ethyl]-3-methoxy-benzamide | 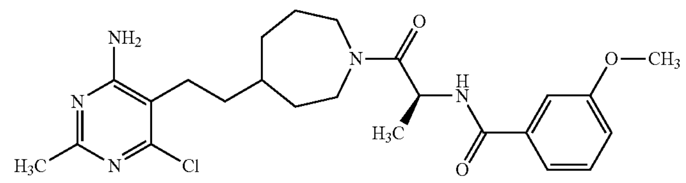 | 474/476 (M + H) |
| 41 | N-[(1S)-2-[(4R,S)-4-[2-(4-Amino-6-chloro-2-methyl-pyrimidin-5-yl)ethyl]azepan-1-yl]-1-methyl-2-oxo-ethyl]-4-methoxy-benzamide | 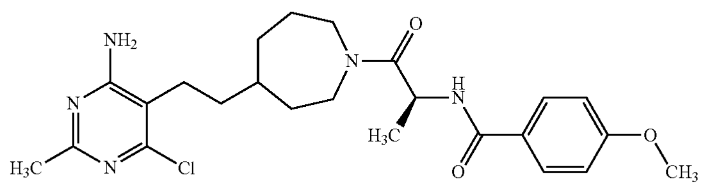 | 474/476 (M + H) |

Example 42

N-[(1S)-2-[4-[2-(4-Amino-6-chloro-2-methyl-pyrimidin-5-yl)ethyl]-1-piperidyl]-1-methyl-2-oxo-ethyl]-2-methyl-thiazole-5-carboxamide

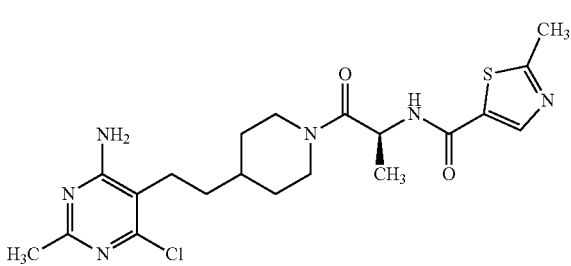 [SMILES: Cc1nc(N)c(CCC2CCN(C(=O)[C@H](C)NC(=O)c3cnc(C)s3)CC2)c(Cl)n1]

Dissolve (2S)-2-amino-1-[4-[2-(4-amino-6-chloro-2-methyl-pyrimidin-5-yl)ethyl]-1-piperidyl]propan-1-one (600 mg, 1.84 mmol) and 2-methylthiazole-5-carboxylic acid (290 mg, 2.03 mmol) in THF (12.3 mL). Add 1-hydroxy-7-azabenzotriazole (281 mg, 2.03 mmol), 1-(3-dimethylaminopropyl)-3-ethylcarbodiimide hydrochloride (430 mg, 2.21 mmol) and TEA (0.77 mL, 5.52 mmol). Stir the mixture at room temperature for 12 hours. Dilute the mixture with EtOAc, filter through a SPE cartridge (ISOLUTE® HM-N) washing with EtOAc and remove the solvent under reduced pressure. Purify the crude mixture by mass-guided SFC (Waters ZQ MS; 4-nitrobenzene-sulfonamide column, eluting with 0.14 mM ammonia in McOH/CO$_2$) to obtain the title compound as a yellow tar (626 mg, 75%). LC-ES/MS m/z ($^{35}Cl/^{37}Cl$) 451/453 (M+H).

Prepare examples 43-65 essentially as described in Example 42 using the corresponding amine intermediate and the appropriately substituted carboxylic acid. LC-ES/MS data are included in Table 2 below.

TABLE 2

| Ex No. | Chemical Name | Structure | LC-ES/MS m/z ($^{35}C/^{37}Cl$) |
|---|---|---|---|
| 43 | N-[(1S)-2-[4-[2-(4-Amino-6-chloro-2-methyl-pyrimidin-5-yl)ethyl]-1-piperidyl]-1-methyl-2-oxo-ethyl]-2-methyl-thiazole-4-carboxamide | 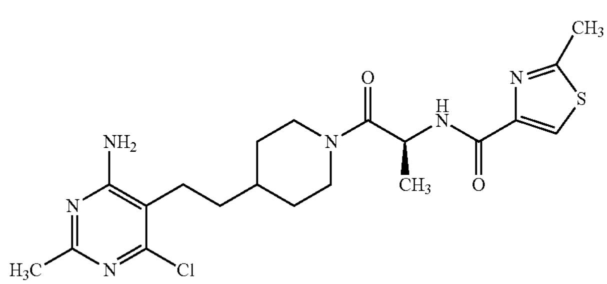 [SMILES: Cc1nc(N)c(CCC2CCN(C(=O)[C@H](C)NC(=O)c3csc(C)n3)CC2)c(Cl)n1] | 451/453 (M + H) |

TABLE 2-continued

| Ex No. | Chemical Name | Structure | LC-ES/MS m/z ($^{35}$C/$^{37}$Cl) |
|---|---|---|---|
| 44 | N-[(1S)-2-[4-[2-(4-Amino-6-chloro-2-methyl-pyrimidin-5-yl)ethyl]-1-piperidyl]-1-methyl-2-oxo-ethyl]-1-methyl-pyrazole-4-carboxamide | 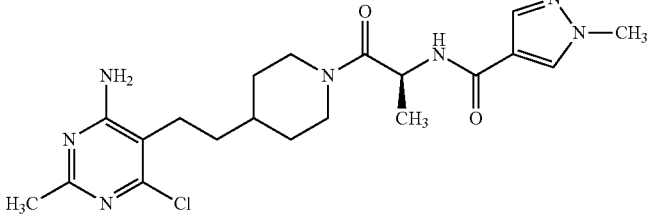 | 434/436 (M + H) |
| 45 | N-[(1S)-2-[4-[2-(4-Amino-6-chloro-2-methyl-pyrimidin-5-yl)ethyl]-1-piperidyl]-1-methyl-2-oxo-ethyl]-pyridine-2-carboxamide | 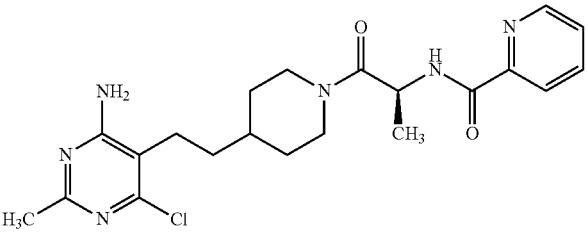 [SMILES: Cc1nc(N)c(CCC2CCN(C(=O)[C@H](C)NC(=O)c3ccccn3)CC2)c(Cl)n1] | 431/433 (M + H) |
| 46 | N-[(1S)-2-[4-[2-(4-Amino-6-chloro-2-methyl-pyrimidin-5-yl)ethyl]-1-piperidyl]-1-methyl-2-oxo-ethyl]-pyridine-3-carboxamide | 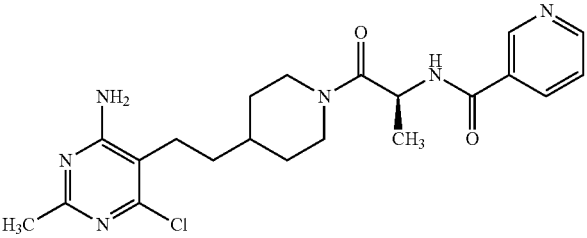 [SMILES: Cc1nc(N)c(CCC2CCN(C(=O)[C@H](C)NC(=O)c3cccnc3)CC2)c(Cl)n1] | 431/433 (M + H) |
| 47 | N-[(1S)-2-[4-[2-(4-Amino-6-chloro-2-methyl-pyrimidin-5-yl)ethyl]-1-piperidyl]-1-methyl-2-oxo-ethyl]-pyridine-4-carboxamide | 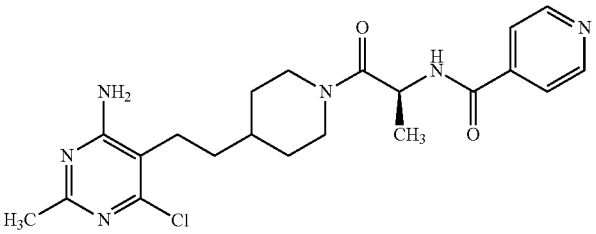 [SMILES: Cc1nc(N)c(CCC2CCN(C(=O)[C@H](C)NC(=O)c3ccncc3)CC2)c(Cl)n1] | 431/433 (M + H) |
| 48 | N-[(1S)-2-[4-[2-(4-Amino-6-chloro-2-methyl-pyrimidin-5-yl)ethyl]-1-piperidyl]-1-methyl-2-oxo-ethyl]-pyridazine-3-carboxamide | 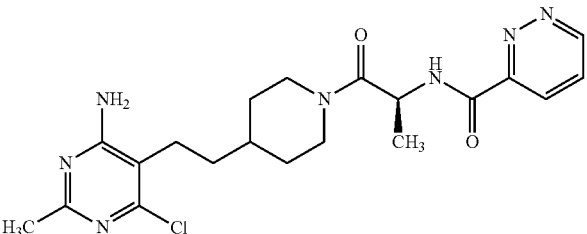 | 432/434 (M + H) |
| 49 | N-[(1S)-2-[4-[2-(4-Amino-6-chloro-2-methyl-pyrimidin-5-yl)ethyl]-1-piperidyl]-1-methyl-2-oxo-ethyl]-pyridazine-4-carboxamide | 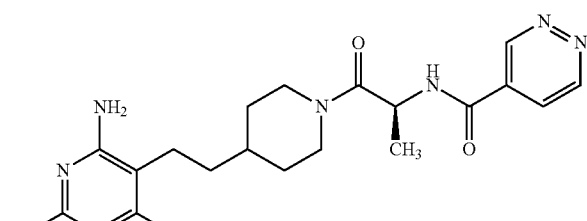 | 432/434 (M + H) |

TABLE 2-continued

| Ex No. | Chemical Name | Structure | LC-ES/MS m/z ($^{35}C/^{37}Cl$) |
|---|---|---|---|
| 50 | N-[(1S)-2-[4-[2-(4-Amino-6-chloro-2-methyl-pyrimidin-5-yl)ethyl]-1-piperidyl]-1-methyl-2-oxo-ethyl]-pyrimidine-4-carboxamide | 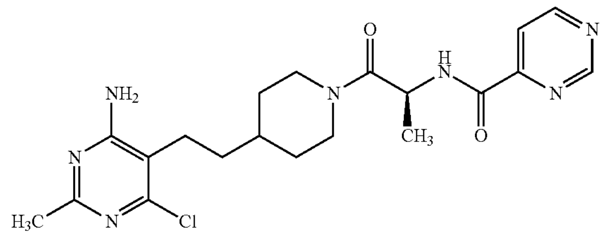 [SMILES: Cc1nc(N)c(CCC2CCN(C(=O)[C@H](C)NC(=O)c3ccncn3)CC2)c(Cl)n1] | 432/434 (M + H) |
| 51 | N-[(1S)-2-[4-[2-(4-Amino-6-chloro-2-methyl-pyrimidin-5-yl)ethyl]-1-piperidyl]-1-methyl-2-oxo-ethyl]-pyrazine-2-carboxamide | 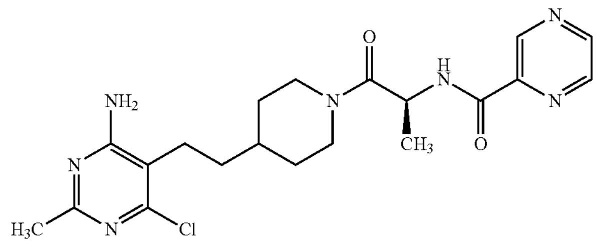 [SMILES: Cc1nc(N)c(CCC2CCN(C(=O)[C@H](C)NC(=O)c3cnccn3)CC2)c(Cl)n1] | 432/434 (M + H) |
| 52 | N-[(1S)-2-[4-[2-(4-Amino-6-chloro-2-methyl-pyrimidin-5-yl)ethyl]-1-piperidyl]-1-methyl-2-oxo-ethyl]-2-methoxy-benzamide | 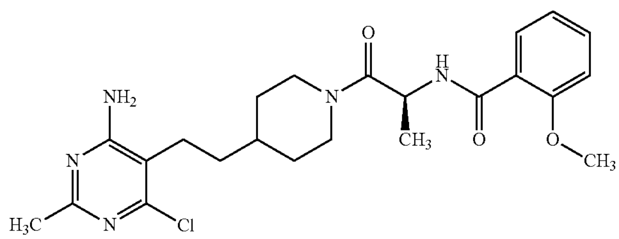 | 460/462 (M + H) |
| 53 | N-[(1S)-2-[4-[2-(4-Amino-6-chloro-2-methyl-pyrimidin-5-yl)ethyl]-1-piperidyl]-1-methyl-2-oxo-ethyl]-3-methoxy-benzamide | 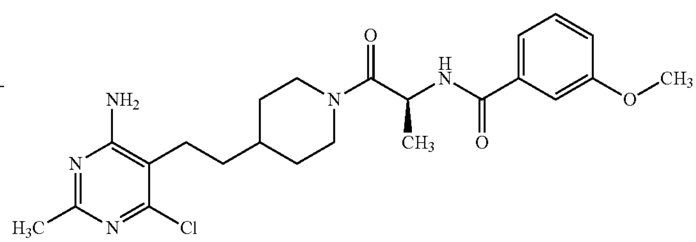 | 460/462 (M + H) |
| 54 | N-[(1S)-2-[4-[2-(4-Amino-6-chloro-2-methyl-pyrimidin-5-yl)ethyl]-1-piperidyl]-1-methyl-2-oxo-ethyl]-4-methoxy-benzamide | 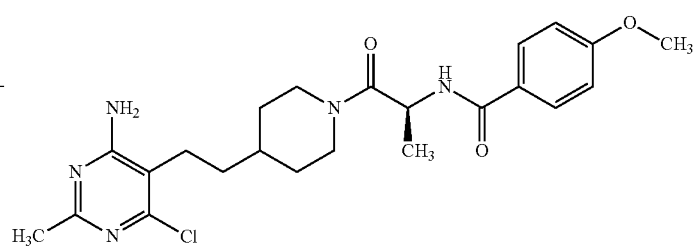 | 460/462 (M + H) |
| 55 | N-[(1S)-2-[4-[2-(4-Amino-6-chloro-2-methyl-pyrimidin-5-yl)ethyl]-1-piperidyl]-1-methyl-2-oxo-ethyl]propanamide | 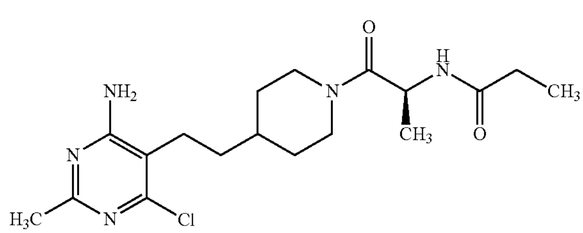 [SMILES: CCC(=O)N[C@@H](C)C(=O)N1CCC(CCc2c(N)nc(C)nc2Cl)CC1] | 382/384 (M + H) |

TABLE 2-continued

| Ex No. | Chemical Name | Structure | LC-ES/MS m/z ($^{35}$Cl/$^{37}$Cl) |
|---|---|---|---|
| 56 | N-[(1S)-2-[4-[2-(4-Amino-6-chloro-2-methyl-pyrimidin-5-yl)ethyl]-1-piperidyl]-1-methyl-2-oxo-ethyl]-2-methyl-propanamide | 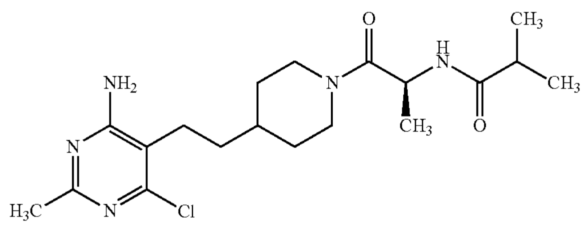 [SMILES: Cc1nc(N)c(CCC2CCN(C(=O)[C@H](C)NC(=O)C(C)C)CC2)c(Cl)n1] | 396/398 (M + H) |
| 57 | N-[(1S)-2-[4-[2-(4-Amino-6-chloro-2-methyl-pyrimidin-5-yl)ethyl]-1-piperidyl]-1-methyl-2-oxo-ethyl]-2-hydroxy-acetamide | 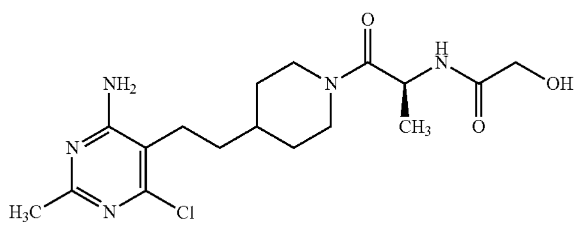 | 384/386 (M + H) |
| 58 | N-[(1S)-2-[4-[2-(4-Amino-6-chloro-2-methyl-pyrimidin-5-yl)ethyl]-1-piperidyl]-1-methyl-2-oxo-ethyl]-2-hydroxy-2-methyl-propanamide | 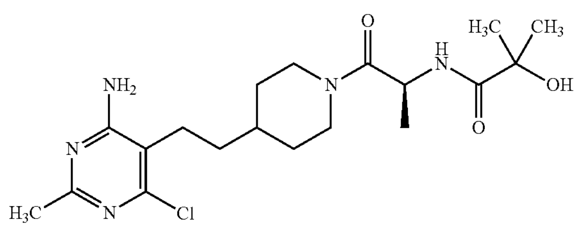 [SMILES: Cc1nc(N)c(CCC2CCN(C(=O)[C@H](C)NC(=O)C(C)(C)O)CC2)c(Cl)n1] | 412/414 (M + H) |
| 59 | N-[(1R)-2-[4-[2-(4-Amino-6-chloro-2-methyl-pyrimidin-5-yl)ethyl]-1-piperidyl]-1-methyl-2-oxo-ethyl]acetamide | 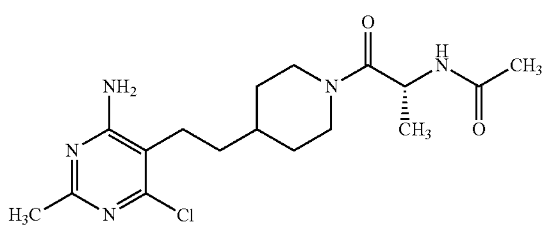 [SMILES: CC(=O)N[C@H](C)C(=O)N1CCC(CCc2c(N)nc(C)nc2Cl)CC1] | 368/370 (M + H) |
| 60 | N-[2-[4-[2-(4-Amino-6-chloro-2-methyl-pyrimidin-5-yl)ethyl]-1-piperidyl]-2-oxo-ethyl]-1-methyl-pyrazole-4-carboxamide | 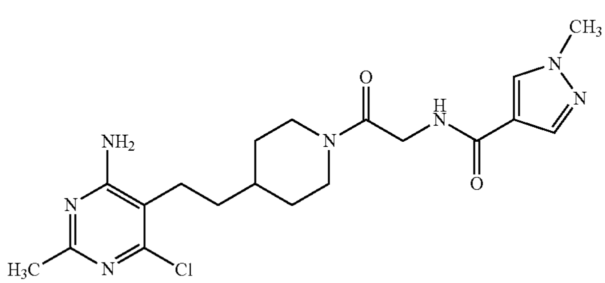 [SMILES: Cc1nc(N)c(CCC2CCN(C(=O)CNC(=O)c3cnn(C)c3)CC2)c(Cl)n1] | 420.2/422. (M + H) |
| 61 | N-[2-[4-[2-(4-Amino-6-chloro-2-methyl-pyrimidin-5-yl)ethyl]-1-piperidyl]-2-oxo-ethyl]pyridine-3-carboxamide | 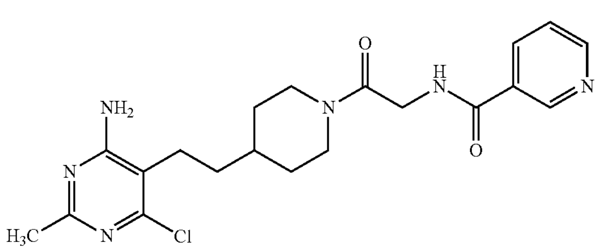 [SMILES: Cc1nc(N)c(CCC2CCN(C(=O)CNC(=O)c3cccnc3)CC2)c(Cl)n1] | 417/419 (M + H) |

TABLE 2-continued

| Ex No. | Chemical Name | Structure | LC-ES/MS m/z ($^{35}C/^{37}Cl$) |
|---|---|---|---|
| 62 | N-[2-[4-[2-(4-Amino-6-chloro-2-methyl-pyrimidin-5-yl)ethyl]-1-piperidyl]-2-oxo-ethyl]pyridine-4-carboxamide | 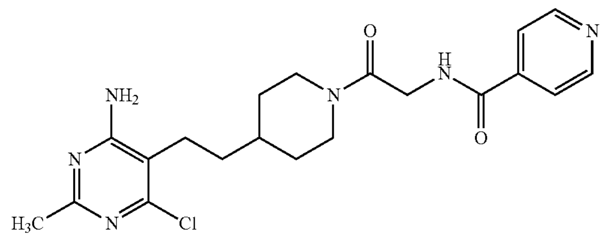 [SMILES: Cc1nc(N)c(CCC2CCN(C(=O)CNC(=O)c3ccncc3)CC2)c(Cl)n1] | 417/419 (M + H) |
| 63 | N-[2-[4-[2-(4-Amino-6-chloro-2-methyl-pyrimidin-5-yl)ethyl]-1-piperidyl]-2-oxo-ethyl]pyridazine-3-carboxamide | 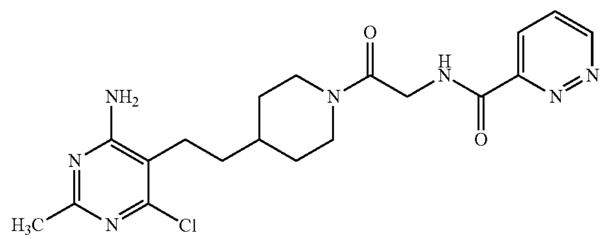 [SMILES: Cc1nc(N)c(CCC2CCN(C(=O)CNC(=O)c3cccnn3)CC2)c(Cl)n1] | 418/420 (M + H) |
| 64 | N-[2-[4-[2-(4-Amino-6-chloro-2-methyl-pyrimidin-5-yl)ethyl]-1-piperidyl]-2-oxo-ethyl]pyridazine-4-carboxamide | 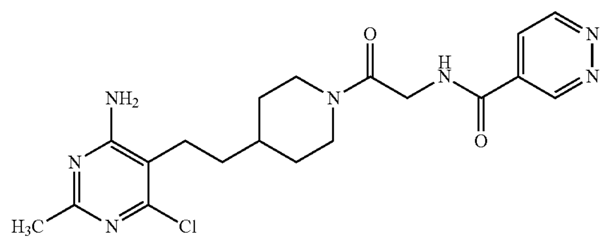 [SMILES: Cc1nc(N)c(CCC2CCN(C(=O)CNC(=O)c3ccnnc3)CC2)c(Cl)n1] | 418/420 (M + H) |
| 65 | N-[2-[4-[2-(4-Amino-6-chloro-2-methyl-pyrimidin-5-yl)ethyl]-1-piperidyl]-2-oxo-ethyl]-4-methoxy-benzamide | 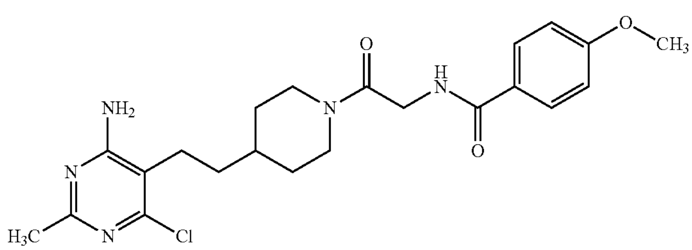 | 446/448 (M + H) |

Alternate route for N-[(1S)-2-[4-[2-(4-Amino-6-chloro-2-methyl-pyrimidin-5-yl)ethyl]-1-piperidyl]-1-methyl-2-oxo-ethyl]-2-methyl-thiazole-5-carboxamide (Example 42)

Dissolve (2S)-2-amino-1-[4-[2-(4-amino-6-chloro-2-methyl-pyrimidin-5-yl)ethyl]-1-piperidyl]propan-1-one dihydrochloride (21.0 g, 52.66 mmol), 2-methyl-5-thiazole-carboxylic acid (11.31 g, 78.99 mmol) and DIPEA (36.7 mL, 210.65 mmol) in DCM (210 mL). Stir until complete dissolution and then cool in an ice bath (internal temperature 5° C.). Add dropwise a solution of 1-propanephosphonic anhydride (50%/solution in EtOAc, 50.27 g, 78.99 mmol) over 5 min to maintain the internal temperature between 5-10° C. Stir in ice bath for 1 hour, allow to warm to room temperature and stir overnight. Dilute with DCM (200 mL) and wash with saturated aqueous sodium bicarbonate (300 mL). Extract the aqueous layer with DCM (3×100 mL) and wash the combined organic layers with saturated ammonium chloride (300 mL), water (300 mL) and brine (500 mL). Dry over MgSO$_4$, filter and remove solvent in vacuum. Purify the crude mixture by chromatography (330 g silica gel column) eluting with 15-60% THF in EtOAc to give the title compound as a pale yellow solid (12.8 g, 54%). LC-ES/MS m/z ($^{35}Cl/^{37}Cl$) 451/453 (M+H).

Example 48, N-[(1S)-2-[4-[2-(4-Amino-6-chloro-2-methyl-pyrimidin-5-yl)ethyl]-1-piperidyl]-1-methyl-2-oxo-ethyl]-pyridazine-3-carboxamide, may be alternately prepared essentially as described in the alternate route to Example 42 above using the corresponding amine intermediate. LC-ES/MS m/z ($^{35}Cl/^{37}Cl$) 432/434 (M+H).

Example 66

N-[(1S)-2-[4-[2-(4-Amino-6-chloro-2-methyl-pyrimidin-5-yl)ethyl]-1-piperidyl]-1-methyl-2-oxo-ethyl]-2-methyl-pyrazole-3-carboxamide

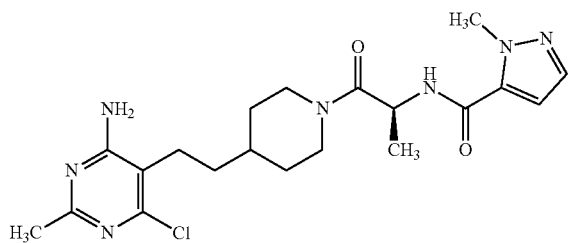 [SMILES: Cc1nc(N)c(CCC2CCN(C(=O)[C@H](C)NC(=O)c3ccnn3C)CC2)c(Cl)n1]

Dissolve DIPEA (15.5 mL, 87.7 mmol) in DCM (100 mL) and add (2S)-2-amino-1-[4-[2-(4-amino-6-chloro-2-methyl-pyrimidin-5-yl)ethyl]-1-piperidyl]propan-1-one dihydrochloride (10.0 g, 25.0 mmol). Stir the solution for 10 min and then add 2-methylpyrazole-3-carboxylic acid (3.32 g, 26.3 mmol) and HATU (9.73 g, 25.6 mmol). Stir the reaction at room temperature for 1 hour with monitoring by LC-MS (low pH). Dilute the mixture with DCM (150 mL) and wash with water (200 mL). Extract the aqueous layer with DCM (2×100 mL). Combine the organic layers and wash with saturated aqueous sodium bicarbonate (100 mL), saturated aqueous ammonium chloride (2×100 mL) and water (100 mL). Dry the organic solution with MgSO$_4$, filter and concentrate under reduced pressure. Dissolve the yellow oil in EtOAc (400 mL) and wash with saturated aqueous ammonium chloride (2×100 mL), water (100 mL) and saturated aqueous sodium chloride (100 mL). Dry the organic solution with MgSO$_4$, filter and concentrate under reduced pressure. Purify the material by chromatography (silica gel) eluting with 0-40% THF in EtOAc. Combine the purified fractions and concentrate under reduced pressure. Dilute the resulting material in iso-hexane (100 mL) and stir for 1 hour. Remove the solvent under reduced pressure to give the title compound as a white powder (9.85 g, 88%). LC-ES/MS m/z ($^{35}$Cl/$^{37}$Cl) 434.2/436.2 (M+H).

Examples 67 (Isomer 1) and 68 (Isomer 2)

N-[(1S)-2-[4-[2-(4-Amino-6-chloro-2-methyl-pyrimidin-5-yl)ethyl]-1-piperidyl]-1-methyl-2-oxo-ethyl]-2-hydroxy-propanamide Isomer 1 and Isomer 2

Isomer 1

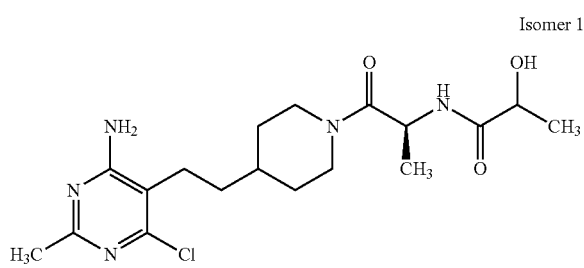

Isomer 2

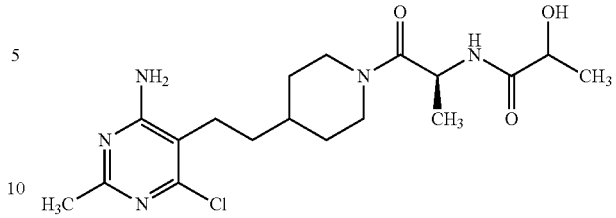

Combine (2S)-2-amino-1-[4-[2-(4-amino-6-chloro-2-methyl-pyrimidin-5-yl)ethyl]-1-piperidyl]propan-1-one (60 mg, 0.184 mmol), lactic acid (85% in water, 0.02 mL, 0.202 mmol), THF (4 mL), 1-hydroxy-7-azabenzotriazole (28.1 mg, 0.202 mmol), 1-(3-dimethylaminopropyl)-3-ethylcarbodiimide hydrochloride (43 mg, 0.221 mmol) and TEA (0.077 mL, 0.55 mmol). Stir the mixture at room temperature for 12 hours. Dilute the mixture with EtOAc, filter through a SPE cartridge (ISOLUTE® HM-N) washing with EtOAc and remove the solvent under reduced pressure. Purify the crude mixture by mass-guided SFC (Waters ZQ MS; 200 A 150×30 mm Phenomenex Luna HILIC column, 5 pt particle size, eluting with 10-20% EtOH/CO2) to obtain N-[(1S)-2-[4-[2-(4-amino-6-chloro-2-methyl-pyrimidin-5-yl)ethyl]-1-piperidyl]-1-methyl-2-oxo-ethyl]-2-hydroxy-propanamide Isomer 1 as a colorless solid (12 mg, 16%) and N-[(1S)-2-[4-[2-(4-amino-6-chloro-2-methyl-pyrimidin-5-yl)ethyl]-1-piperidyl]-1-methyl-2-oxo-ethyl]-2-hydroxy-propanamide Isomer 2 as a colorless solid (12 mg, 16%). Isomer 1: LC-ES/MS m/z ($^{35}$Cl/$^{37}$Cl) 451/453 (M+H). Isomer 2: LC-ES/MS m/z ($^{35}$Cl/$^{37}$Cl) 451/453 (M+H).

Example 69

N-[(1S)-2-[4-[2-(4-Amino-6-chloro-2-methyl-pyrimidin-5-yl)ethyl]-1-piperidyl]-1-methyl-2-oxo-ethyl]acetamide

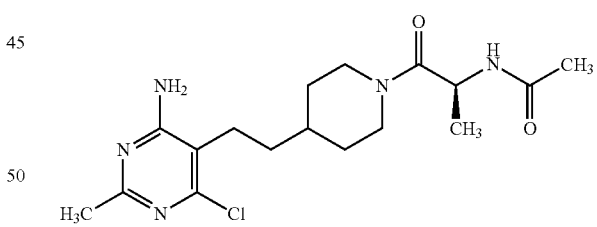

Execute the following procedure in two separate lots.
Dissolve (2S)-2-amino-1-[4-[2-(4-amino-6-chloro-2-methyl-pyrimidin-5-yl)ethyl]-1-piperidyl]propan-1-one hydrochloride (13.5 g, 31.6 mmol) in DCM (114 mL) and add DIPEA (16.5 mL, 95.0 mmol). Add acetic anhydride (12.0 mL, 126 mmol) and stir for 45 min. Dilute the mixture with DCM (100 mL) and wash with saturated aqueous sodium bicarbonate (50 mL), water (3×75 mL), and saturated aqueous sodium chloride (75 mL). Dry the organic portion over MgSO$_4$, filter and concentrate under reduced pressure. Into the resulting residue add diethyl ether (50 mL), swirl, and filter rinsing with diethyl ether (2×15 mL). Dry the resultant solid for 2 hours under vacuum. At this point combine the two lots and dry the combined solid for

Example 70

Methyl N-[(1S)-2-[4-[2-(4-amino-2-chloro-6-methyl-pyrimidin-5-yl)ethyl]-1-piperidyl]-1-methyl-2-oxo-ethyl]carbamate

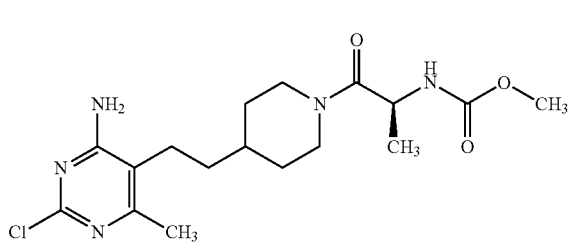 [SMILES: COC(=O)N[C@@H](C)C(=O)N1CCC(CCc2c(C)nc(Cl)nc2N)CC1]

Add (2S)-2-amino-1-[4-[2-(4-amino-2-chloro-6-methyl-pyrimidin-5-yl)ethyl]-1-piperidyl]propan-1-one dihydrochloride (125 mg, 0.31 mmol), DCM (10 mL) and TEA (0.1 mL, 0.7 mmol). Stir the mixture for 5 min and add N,N-dimethyl 4-pyridinamine (4 mg, 0.03 mmol) and dimethyldicarbonate (420 mg, 3.13 mmol). Stir the reaction at room temperature overnight. Add DCM (50 mL) and wash with saturated aqueous sodium bicarbonate (20 mL). Wash the organic phase with saturated aqueous sodium chloride (30 mL), dry over Na$_2$SO$_4$, filter and concentrate under reduced pressure. Dissolve the crude mixture into a minimal amount of DCM and filter through a SPE cartridge (20 g silica) eluting with 30-100% acetone in hexane. Purify the crude mixture by mass-guided SFC [Waters SFC-MS Prep 100; 30×150 mm 2-ethylpyridine column; 5µ particle size; CO$_2$ (A)/MeOH (B) as mobile phase; isocratic mode (10% B for 1 min, gradient from 10-20% B in 3 min, from 20-40% B in 0.5 min, 1 min wash step at 40% B and back to initial conditions in 0.5 min); flow rate 100 mL/min] to obtain the title compound as a white solid (60 mg, 46%). LC-ES/MS m/z ($^{35}$Cl/$^{37}$Cl) 384/386 (M+H), T$_R$=1.34 min, gradient program 2.

Example 71

Methyl N-[(1S)-2-[4-[2-(4-amino-6-chloro-2-methyl-pyrimidin-5-yl)ethyl]-1-piperidyl]-1-methyl-2-oxo-ethyl]carbamate

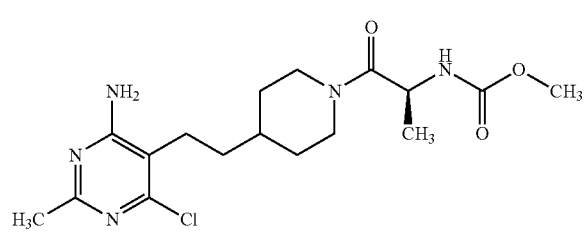

The compound of Example 71 is prepared essentially as described in Example 70 using the corresponding amine intermediate and the appropriately substituted dimethyldicarbonate. LC-ES/MS m/z ($^3$Cl/$^{37}$Cl) 384/386 (M+H).

Example 72 tert-Butyl N-[(1S)-2-[4-[2-(4-amino-6-chloro-2-methyl-pyrimidin-5-yl)ethyl]-1-piperidyl]-1-methyl-2-oxo-ethyl]carbamate

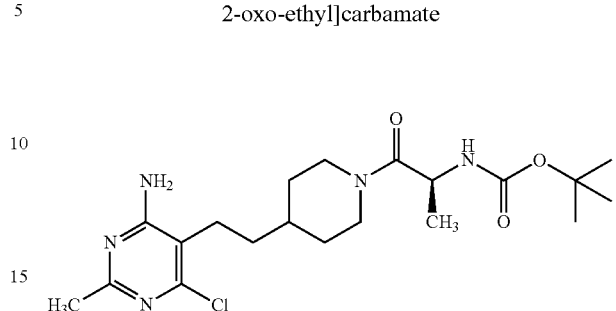

Into each of two round bottom flasks add 6-chloro-2-methyl-5-[2-(4-piperidyl)ethyl]pyrimidin-4-amine hydrochloride (12.50 g, 42.92 mmol), DIPEA (22.46 mL, 128.7 mmol) and DMF (100 mL). Cool the two mixtures in a cold water bath and stir for 5 min. Add to each of the mixtures HATU (17.95 g, 47.21 mmol) and (2S)-2-(tert-butoxycarbonylamino)propanoic acid (8.93 g, 47.21 mmol) in one portion. Stir the mixtures at room temperature for 90 min. Pour the mixtures into separate separatory funnels along with water (300 mL) and EtOAc (400 mL), shake and partition. Extract the aqueous layers with EtOAc (3×300 mL), wash the respective organic layers with water (4×250 mL), saturated aqueous sodium chloride (200 mL) and dry over MgSO$_4$, filter and concentrate under reduced pressure. Purify the combined materials via silica gel chromatography eluting with 70-100% EtOAc in hexane. Combine and concentrate the purified fractions under reduced pressure. Dilute the residue with EtOAc (500 mL) and wash with saturated aqueous ammonium chloride (100 mL), saturated aqueous sodium bicarbonate (100 mL), water (100 mL) and saturated aqueous sodium chloride (100 mL). Dry the organics over MgSO$_4$, filter, and concentrate under reduced pressure to give the title compound as a white solid (28.0 g, 76%). LC-ES/MS m/z ($^{35}$Cl/$^{37}$Cl) 426.2/428.2 (M+H).

Example 73 tert-Butyl N-[(1S)-2-[(4R,S)-4-[2-(4-amino-6-chloro-2-methyl-pyrimidin-5-yl)ethyl]azepan-1-yl]-1-methyl-2-oxo-ethyl]carbamate

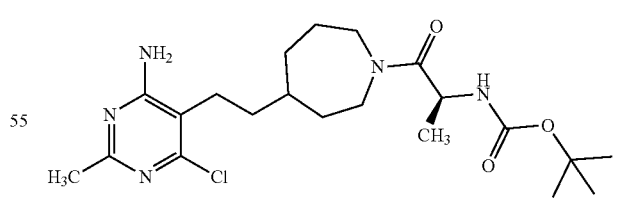

Dissolve 5-[2-[(4R,S)-azepan-4-yl]ethyl]-6-chloro-2-methyl-pyrimidin-4-amine (1.0 g, 3.72 mmol), (2S)-2-(tert-butoxycarbonylamino)propanoic acid (1.06 g, 5.58 mmol) in DCM (4 mL) and THF (10 mL). Add TEA (1.56 mL, 11.16 mmol), 1-hydroxy-7-azabenzotriazole (0.760 g, 5.58 mmol) and 1-(3-dimethylaminopropyl)-3-ethylcarbodiimide hydrochloride (1.43 g, 7.44 mmol). Stir the resulting mixture at room temperature under nitrogen overnight. Remove solvent under reduced pressure, dissolve the residue in EtOAc and wash with water. Dry the organic fraction over Na$_2$SO$_4$, filter and concentrate under reduced pressure. Purify the crude mixture by chromatography (80 g silica gel column) eluting with 0-10% DCM in methanol to obtain the title compound (1.40 g, 86%). LC-ES/MS m/z ($^{35}$Cl/$^{37}$Cl) 440/442 (M+H).

Example 74 tert-Butyl N-[(1R)-2-[4-[2-(4-amino-6-chloro-2-methyl-pyrimidin-5-yl)ethyl]-1-piperidyl]-1-methyl-2-oxo-ethyl]carbamate

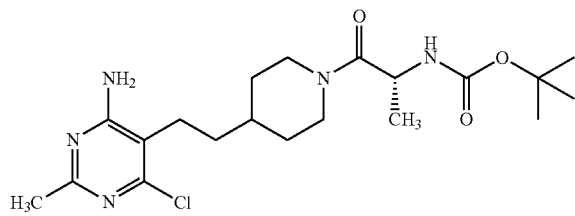 [SMILES: Cc1nc(N)c(CCC2CCN(C(=O)[C@@H](C)NC(=O)OC(C)(C)C)CC2)c(Cl)n1]

The compound of Example 74 is prepared essentially as described in Example 73 using the corresponding amine intermediate and the appropriately substituted carboxylic acid. LC-ES/MS m/z ($^{35}$Cl/$^{37}$Cl) 426/428 (M+H).

Assays

GOAT is the principal enzyme that converts UAG to AG. For reviews of the role of GOAT and ghrelin see: Kristy M. Heppner et al, *The ghrelin O-acyltransferase-ghrelin system: a novel regulator of glucose metabolism*, Current Opinion in Endocrinology, Diabetes & Obesity 2011, 18:50-55; Phillip A. Cole et al., *Glucose and Weight Control in Mice with a Designed Ghrelin OAcyltransferase Inhibitor*, Science. 2010 Dec. 17; 330(6011): 1689-1692. doi:10.1126/science.1196154, Matthias H. Tschöp et al., *Gastric O-acyl transferase activates hunger signal to the brain*, Proc Natl Acad Sci USA. 2008 Apr. 29; 105(17): 6213-6214, and Jesus Gutierrez, et al., *Ghrelin octanoylation mediated by an orphan lipid transferase*, Proc Natl Acad Sci USA., 2008 Apr. 29, 105 (17): 6320-6325.

The role of GOAT is supported by the phenotypes observed in mice devoid of GOAT gene. Therefore, inhibition of GOAT is expected to decrease circulating AG and raise circulating UAG. Consequently, the ratio of AG to total ghrelin (UAG+AG) is reduced after GOAT inhibitor treatment.

In Vitro Cell Free Human GOAT Enzymatic Assay

Human GOAT gene (Accession number: NM_001100916) is subcloned to pAN51 baculoviral expression vector. Baculovirus stock is prepared following the Bac-to-Bac Protocol provided by the vendor, Invitrogen, California, USA. Five mililiters of human GOAT baculoviral stock are added to 500 mL Sf9 cells in HyQ SFX-Insect™ media (HyClone catalog number SH30278.02) at the density of 1×10$^6$ cells per mililiter in a 2 L Erlenmeyer flask. The flask with human GOAT gene infected Sf9 cells is put on a plate shaker at 120 rpm at 28° C. for 48 h. After 48 h incubation, cells are centrifuged at 1,000×g for 10 min at 4° C. The cell pellets are collected and stored at –80° C. in a freezer until ready for further processing.

Preparation of Microsomal Membrane of GOAT Enzyme for the Enzymatic Assay:

One gram cell pellets are suspended in 9 mL chilled homogenization buffer (50 mM Tris-HCl, 250 mM sucrose, adjusted to pH 7.5, and sterile filtered through 0.2 μm Millipore filter). The cell suspension is transferred to a Dounce glass homogenizer. Cell pellets are homogenized with 40 strokes on ice. The homogenate is centrifuged at 3,000 rpm in a Beckman swing bucket rotor at 4° C. for 10 min to remove unbroken cells. The supernatant is collected and centrifuged at 40,000×g for 1 h at 4° C. The resulting membrane pellet is suspended in the homogenization buffer using a Dounce glass homogenizer and stored at –20° C. in the freezer for the assay. For long term storage of the human GOAT enzyme membrane preparation, the suspended membrane is stored in a –80° C. freezer.

Human GOAT Enzymatic Assay Protocol:

Prepare test compounds in DMSO to make up a 0.2 mM stock solution. Serially dilute the stock solution in DMSO for ten concentrations with final compound concentrations ranging from 10 μM to 0.5 nM in a 96-well round-bottom plate. Prepare enzyme and substrate solutions in assay buffer (0.02% TWEEN™-20 in 50 mM Tris, pH 7.5 containing 250 mM sucrose, 1 mg/mL BSA and 10 mM EDTA). Add diluted compound (1 μL) to each well of row A to N of a corresponding low protein binding 384 well plate. Add human GOAT substrate mix (10 μL), consisting of human desacyl-ghrelin-biotin (CPC Scientific Inc., 6.0 μM final), octanoyl-CoA (Sigma, 60 μM final) and an AG specific antibody (WO 2006/091381) (1.0 μg/mL final), to the compounds. Add GOAT-His/sf9 enzyme preparation, that has been prepared in assay buffer (9 μL), to each well of the plate containing substrate and test compounds resulting in a final concentration of 0.01 μg/mL to initiate the reaction. Incubate the mixture for 1 h at RT on a gently rotating oscillator. Add 4 M guanidine hydrochloride (20 μL) to all wells, mix, and incubate for 3 h to stop the reaction.

Prepare ELISA plates (STREPTAVIDIN SPECTRA-PLATE™ 384, Perkin Elmer) by blocking with 2% Heat-Inactivated FBS in PBS (40 μL) (Invitrogen) blocking buffer for 3 h. Aspirate the blocking buffer from ELISA plate and add blocking buffer (23 μL) to columns 1-24, rows A-N. Reserve rows O and P for the acylghrelin standard curve. Add the reaction mixture (2 μL) to the ELISA plates. Prepare a 10 point standard curve (biotin-labeled octanoyl-ghrelin) by serial 2× dilution in blocking buffer containing 0.2M Guanidine hydrochloride starting at 2.5 μM. Incubate the reaction mixture or biotin-labeled AG standard in the ELISA plate overnight at 4° C. The following day, wash the plate 3× with wash buffer (0.1% TWEEN™-20/PBS, 100 μL per well in each wash cycle). Add AG specific antibody (WO 2006/091381) (25 μL of 0.5 μg/mL in blocking buffer) to each well and incubate at RT for 1 h. Wash the plate 3× with the wash buffer, similarly to the previous step. Add Protein G-HRP (25 μL) (Southern Biotech) diluted 3,000× in blocking buffer and incubate 1 h at RT. Wash the late 3× with wash buffer, as in the previous steps. Add TMB reagent (25 μL) (Kirkegaard & Perry Laboratories, Inc.) to each well and let develop for 20 min and stop with 1 M phosphoric acid (25 μL per well). Read plates at 450 nm using an ENVISION® Multilabel plate reader. AG levels are calculated versus a fitted standard curve and percent inhibition calculated. The 10-point inhibition curve is plotted and fitted with the four-parameter logistic equation to obtain IC$_{50}$ values using ACTIVITYBASE® (ver. 7.3.2.1).

Following a protocol essentially as described above, all of the compounds of the Examples herein were tested and exhibited an $IC_{50}$ for the in vitro cell free human GOAT enzymatic assay of lower than 1 µM. The following exemplified compounds of the invention were tested essentially as described above and exhibited the following activity as illustrated in Table 3 below.

TABLE 3

| Example No. | $IC_{50}$ [nM] |
|---|---|
| 2 | 54.4 (n = 1) |
| 37 | 574 (n = 1) |
| 42 | 96.4 ± 28.3 (n = 3) |
| 66 | 68.9 ± 23.6 (n = 4) |
| 69 | 170 ± 103 (n = 10) |
| 71 | 149 ± 46 (n = 3) |

The data in Table 3 demonstrate that the compounds of Table 3 inhibit purified GOAT enzyme activity in vitro.

Comparing the change in the ratio of AG to total ghrelin in the compound treated group and that of the vehicle treated group reflects the degree of GOAT enzyme inhibition in vivo, due to the dynamic processing of UAG to AG by the GOAT enzyme. In the in vivo pharmacodynamic studies herein, the levels of AG and UAG in plasma and stomach in the vehicle and compound treated groups are measured by ELISA specifically to these two analytes. The total ghrelin level of each sample is computed as the sum of AG and UAG by these ELISA measurements. The ratio of AG to total ghrelin is defined by the level of AG in each sample divided by the level of total ghrelin in the same sample. The levels of AG, UAG and ratio of AG to total ghrelin in the vehicle treated group is computed and set as 100%. The relative change of these parameters in the compound treated group is then computed to determine the effectiveness of the test compound.

In Vivo Dose Dependent 3 Day BID Study for GOAT Inhibitor

Animals and Treatment:

Purchase male C57BL/6 mice from Harlan (Indianapolis, Ind.) at 9 weeks of age. House the mice individually in a temperature-controlled (24° C.) facility with a 12 h light/dark cycle (lights on 2200 h), and allow free access to a standard rodent chow (diet 2014, Harlan) and water. Typically, use the mice when they are 10-13 weeks of age at the time of the study. On day 0 of the experiment, randomize the mice into treatment groups (N=7/group) so each group has similar mean body weights. On day 1 and day 2, treat the animals with vehicle (1% hydroxyethylcellulose, 0.25% TWEEN™ 80, 0.05% antifoam) or test compound prepared in the vehicle as suspension at various dosages by oral gavage at 7 am and 7 pm. On day 3, fast the animals, move them into clean cages and dose with vehicle or the test compound again at 8 am by oral gavage. That same day at 1 pm, sacrifice the animals by decapitation to collect blood. For details of blood collection and plasma treatments see Blood collection and Extraction of Ghrelin from Plasma section below.

Blood Collection:

Collect approximately 600 µL blood into a pre-weighed EDTA tube containing 600 µL (defined as $V_{preservative}$) freshly-prepared preservative (4 mM PEFABLOC® [4-(2-aminoethyl) benzenesulfonyl fluoride hydrochloride], 72 mM NaCl, 58 mM NaF, 0.032 N hydrochloric acid, pH 3.0) and mix immediately. Weigh the tube again and keep on ice. To accurately determine the exact blood volume of each sample using this blood collection procedure, the weight of the blood for each mouse is computed using the following equation:

Weight of Blood=(Weight of the tube containing Blood+preservative)−(Weight of the tube containing preservative)

Blood volume($V_{blood}$)=(Weight of blood)/1.06

Note, the density of rodent blood is assumed as 1.06 g/mL.

Within 15 minutes after the blood collection, samples are centrifuged at 5000 rpm at 4° C. for 8 min. Remove plasma (650 µL) to a 5 mL glass tube containing 1 N hydrochloric acid (65 µL), mix and keep on ice.

Ghrelin Extraction by SEP-PAK® Column:

AG and UAG are extracted from plasma using SEP-PAK® $C_{18}$ column to remove interference prior to performing the ELISA. The solid phase extraction of AG and UAG peptides by SEP-PAK® $C_{18}$ columns can be performed on a vacuum manifold (Waters Corp) or using a peristaltic pump. The sample SEP-PAK® column extraction procedure is independently applied to the plasma sample obtained from each individual mouse. The general extraction protocol is described as follows.

All solutions used for the entire protocol of the SEP-PAK® column extraction should be at ice cold condition. Wet SEP-PAK®_columns (WAT054960, Waters Corp, Milford Mass.) with 99.9% ACN/0.1% TFA (1 mL of solution of 100 mL ACN/0.1 mL TFA). Apply pressure to adjust the flow-rate to about 1 ml/min to remove liquid from the column bed but do not allow the column to dry out at any point. Once liquid is removed from the column, stop the pressure. Equilibrate the columns with 3% ACN/0.1% TFA (1 mL of 97 mL water, 3 mL ACN, 0.1 mL TFA). Apply pressure to adjust the flow-rate to about 1 mL/min to remove liquid from the column bed, but do not let the column dry out. Dilute approximately 650 µL acidified plasma (defined as $V_{plasma\ added\ to\ column}$) to 1.4 mL ice cold 0.1% TFA. Load all diluted acidified plasma from the previous step onto the columns. Apply pressure to adjust the flow-rate to about 0.5 mL/min to allow sample passing through the column and ghrelin peptides to absorb onto the resin of the column. Do not let the column dry out. Wash with 3% ACN/0.1% TFA (0.9 mL of 97 mL water, 3 mL ACN, 0.1 mL TFA). Apply pressure to adjust the flow-rate to about 1 mL/min to remove liquid from the column bed but do not let the column dry out. Repeat the wash two more times. Elute with 60% ACN/0.1% TFA (1 mL of 40 mL water, 60 mL ACN, 0.1 mL TFA). Put a collection tube underneath of each column, apply pressure to adjust the flow-rate to about 0.5 mL/min to push liquid through the column and collect the eluent into the collection tube. Freeze the samples on dry ice immediately. Lyophilize the samples in a speed-vacuum (Model# SC110A, Savant) and store at −20° C. until the ELISA assay is performed.

ELISA Assay for Ghrelin:

Coat 96-well MULTI-ARRAY® MSD® plates (Meso Scale Discovery, Gaithersberg, Md., Catalog # L15XA-3) with 100 µL of 1 µg/mL of an antibody (WO 2005/026211 AND WO2006/019577) that recognizes the mid-domain of both the acyl and unacylated forms of ghrelin in PBS (Invitrogen). Tap the sides of the plates to ensure coverage of wells, seal with adhesive plate sealer, and incubate overnight at RT. Discard the contents and add BLOCKER™ Casein in PBS (100 µL) (Thermo Scientific, Rockford, Ill., Catalog #37528) to each well. Reseal the plates and put on a plate shaker at RT for 1 h.

Reconstitute the lyophilized preserved plasma samples from the SEP-PAK® $C_{18}$ column extraction in BLOCKER™ Casein in PBS (400 µL to each sample, this volume is defined as $V_{reconstitution}$), mix well with a vortex mixer and incubate on ice for 45-60 min. Discard the contents from the plates and add reconstituted plasma samples at 25 µL to each well. Prepare acylghrelin and unacylated ghrelin standard curves beginning with 8000 µg/mL and performing serial 1:4 dilutions for 8 total concentrations. Add the prepared standards in duplicate to the blocked plates with 25 µL in each well. Seal the plates and incubate at RT on a plate shaker for 2 h.

Discard the plate contents and wash three times with PBS including 0.1% TWEEN™ 20 (150 µL) (PBS-T). Acylghrelin specific antibody (WO 2006/091381) or unacylated ghrelin specific antibody (WO 2006/055347) labeled with MSD® SULFO-TAG™ (Meso Scale Discovery) are diluted to 0.05 µg/mL in 0.2× Blocker Casein containing 0.05% TWEEN™ 20, named secondary antibody solution. Remove the final wash and add secondary antibody solution (25 µL to each well) which specifically recognizes AG or UAG. The plates are resealed and incubated for 1 h at RT on a plate shaker before finally washing 3× again with PBS-T (150 µL/well).

Discard the final wash and replace with 1×MSD® Read Buffer (150 µL/well). Read the electrochemiluminescent signal generated by activation of the bound MSD® SULFO-TAG™ label to the electrodes on the plates using the MSD® SECTOR® Imager 6000 analyzer (Meso Scale Discovery). Calculate concentrations of acylghrelin or unacylated ghrelin based on the respective standard curve generated by the MSD® software. Determine the actual plasma concentration for each sample by multiplying the measured acylghrelin or unacylated ghrelin level by a dilution factor. The dilution factor for each plasma sample is computed with the following equation.

$$DilutionFactor = \left(\frac{V_{blood} + V_{preservative}}{V_{blood}}\right) \times \left(\frac{V_{reconstitution}}{V_{plasma\ loaded\ to\ column}}\right)$$

Results:

Administration of the compound of Example 42 for 3 days decreases plasma AG by 51%, 57%, and 70%, and increases UAG by 1.61, 2.04, and 2.00 fold, respectively at 0.3, 1, and 3 mg/kg (results in Table 6 below, n=7 for each treatment group). Administration at 0.3, 1, and 3 mg/kg results in 61%, 73% and 81% reduction respectively in AG to total ghrelin ratio when compared to the vehicle-treated control animals.

TABLE 4

| Treatment | AG (% of control) | UAG (% of vehicle control) | AG/Total-ghrelin (% of vehicle control) |
|---|---|---|---|
| Vehicle | 100 (n = 7) | 100 (n = 7) | 100 (n = 7) |
| 0.3 mg/kg | 49 ± 7 (n = 7) | 161 ± 24 (n = 7) | 39 ± 2 (n = 7) |
| 1 mg/kg | 43 ± 6 (n = 7) | 204 ± 24 (n = 7) | 27 ± 1 (n = 7) |
| 3 mg/kg | 30 ± 4 (n = 7) | 200 ± 20 (n = 7) | 19 ± 1 (n = 7) |

The results in Table 4 demonstrate that the compound of Example 42 suppresses AG production and elevates the UAG in circulation, as shown in the GOAT knock-out mouse, in vivo.

Administration of the compound of Example 66 for 3 days decreases plasma AG by 34%, 52%, 72%, 79% and 81%, and increases UAG by 2.13, 2.61, 2.92, 3.02 and 2.79 fold, respectively at 0.2, 0.6, 2, 6 and 18 mg/kg (results in Table 7 below). Administration at 0.2, 0.6, 2, 6 and 18 mg/kg results in 50%, 65%, 79%, 84% and 86% reduction respectively in AG to total ghrelin ratio when compared to the vehicle-treated control animals.

TABLE 5

| Treatment | AG (% of control) | UAG (% of vehicle control) | AG/Total-ghrelin (% of vehicle control) |
|---|---|---|---|
| Vehicle | 100 (n = 7) | 100 (n = 7) | 100 (n = 7) |
| 0.2 mg/kg | 66 ± 12 (n = 7) | 213 ± 27 (n = 7) | 50 ± 3 (n = 7) |
| 0.6 mg/kg | 48 ± 4 (n = 7) | 261 ± 30 (n = 7) | 35 ± 1 (n = 7) |
| 2 mg/kg | 28 ± 3 (n = 14) | 292 ± 43 (n = 14) | 21 ± 1 (n = 14) |
| 6 mg/kg | 21 ± 3 (n = 7) | 302 ± 48 (n = 7) | 16 ± 1 (n = 7) |
| 18 mg/kg | 19 ± 6 (n = 7) | 279 ± 36 (n = 7) | 14 ± 2 (n = 7) |

The results of Table 5 demonstrate that the compound of Example 66 suppresses AG production and elevates the UAG in circulation, as shown in the GOAT knock-out mouse, in vivo.

Administration of the compound of Example 71 for 3 days decreases plasma AG by 13%, 37%, and 66%, and increases UAG by 2.87, 3.44, and 2.90 fold, respectively at 0.3, 1, and 3 mg/kg (results in Table 9 below). Administration at 0.3, 1, and 3 mg/kg results in 59%, 73% and 82% reduction respectively in AG to total ghrelin ratio when compared to the vehicle-treated control animals.

TABLE 6

| Treatment | AG (% of control) | UAG (% of vehicle control) | AG/Total-ghrelin (% of vehicle control) |
|---|---|---|---|
| Vehicle | 100 (n = 7) | 100 (n = 7) | 100 (n = 7) |
| 0.3 mg/kg | 87 ± 18 (n = 7) | 287 ± 43 (n = 7) | 41 ± 3 (n = 7) |
| 1 mg/kg | 63 ± 15 (n = 7) | 344 ± 63 (n = 7) | 27 ± 2 (n = 7) |
| 3 mg/kg | 34 ± 5 (n = 7) | 290 ± 30 (n = 7) | 18 ± 1 (n = 7) |

The results of Table 6 demonstrate that the compound of Example 71 suppresses AG production and elevates the UAG in circulation, as shown in the GOAT knock-out mouse, in vivo.

We claim:
1. A compound of formula

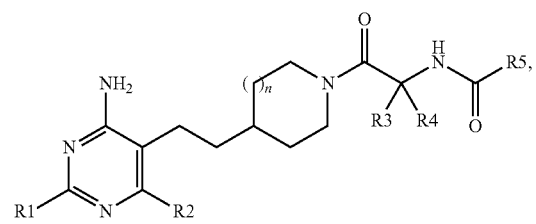

wherein
n is 1 or 2;
$R^1$ and $R^2$ are selected from $CH_3$ and Cl, so long as $R^1$ and $R^2$ are not both —$CH_3$ or both —Cl;

R³ and R⁴ are selected from —H and —CH₃, so long as R³ and R⁴ are not both —CH₃;
R⁵ is selected from —C₁-C₃ alkyl optionally substituted with —OH or —CF₃;
—OC₁-C₄ alkyl; C₃-C₆ cycloalkyl; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, pyrimidinyl, or pyrazinyl; and phenyl optionally substituted with —OCH₃;
provided that when n is 1, R¹ is —CH₃, R² is —Cl, R³ is —CH₃, and R⁴ is —H, then R⁵ cannot be cyclopropyl or a pharmaceutically acceptable salt thereof.

2. The compound of claim 1 wherein n is 1 or 2; R¹ and R² are selected from —CH₃ and —Cl, so long as R¹ and R² are not both —CH₃ or both —Cl; R³ and R⁴ are selected from —H and —CH₃ so long as R³ and R⁴ are not both —CH₃; R⁵ is selected from
—C₁-C₃ alkyl optionally substituted with —OH or —CF₃; —OCH₃ or —OC(CH₃)₃; cyclopropyl; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, pyrimidinyl, or pyrazinyl; and phenyl optionally substituted with —OCH₃; provided that when n is 1, R¹ is —CH₃, R² is
—Cl, R³ is —CH₃, and R⁴ is —H, then R⁵ cannot be cyclopropyl, or a pharmaceutically acceptable salt thereof.

3. The compound of claim 1 of the formula

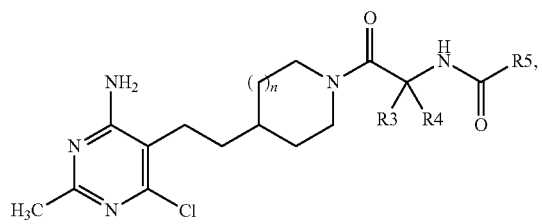

wherein
n is 1 or 2;
R³ and R⁴ are selected from —H and —CH₃, so long as R³ and R⁴ are not both —CH₃;
R⁵ is —C₁-C₃ alkyl optionally substituted with —OH or —CF₃; —OCH₃ or
—OC(CH₃)₃; pyrazolyl, oxazolyl, thiazolyl, or thiadiazolyl, wherein pyrazolyl, oxazolyl, or thiazolyl each may be optionally substituted one to two times with —CH₃ or —CH₂CH₃; pyridinyl, pyridazinyl, pyrimidinyl, or pyrazinyl; and
phenyl optionally substituted with —OCH₃;
or a pharmaceutically acceptable salt thereof.

4. The compound of claim 1 of the formula

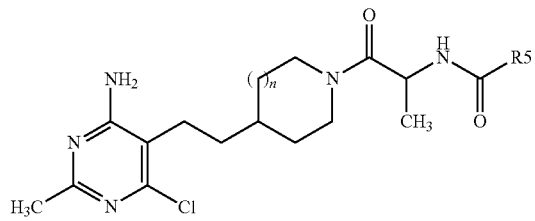

wherein
n is 1 or 2;
R⁵ is —C₁-C₃ alkyl optionally substituted with —CF₃; —OCH₃ or —OC(CH₃)₃; pyrazolyl, oxazolyl, thiazolyl, or thiadiazolyl, wherein pyrazolyl, oxazolyl, or thiazolyl each may be optionally substituted one to two times with —CH₃ or
—CH₂CH₃; pyridinyl, pyridazinyl, or pyrazinyl; or phenyl optionally substituted with —OCH₃; or a pharmaceutically acceptable salt thereof.

5. The compound of claim 1 wherein the compound is

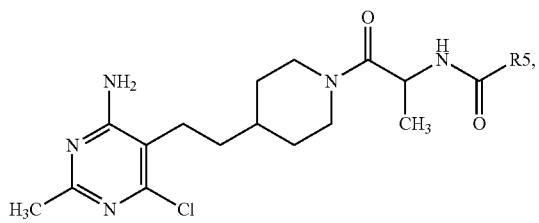

wherein R⁵ is —CH₃; —OCH₃; or pyrazolyl or thiazolyl, wherein pyrazolyl or thiazolyl may be optionally substituted with —CH₃, or a pharmaceutically acceptable salt thereof.

6. The compound of claim 1 wherein when R³ or R⁴ is —CH₃, the configuration of the carbon atom with said —CH₃ is (S); or a
pharmaceutically acceptable salt thereof.

7. The compound of claim 1 wherein the compound is

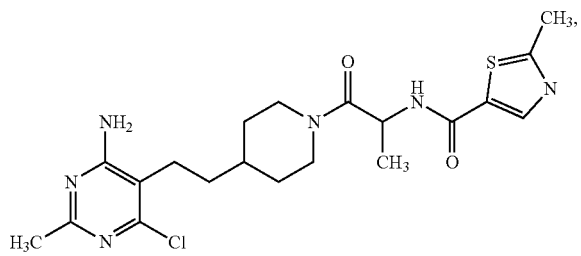

or a pharmaceutically acceptable salt thereof.

8. The compound of claim 7 wherein the compound is

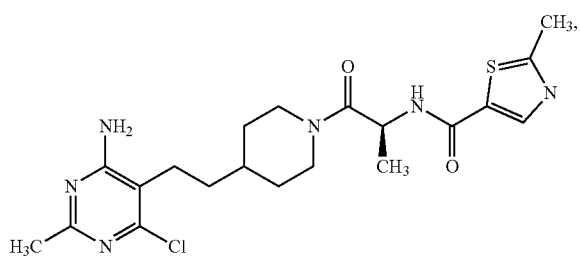

or a pharmaceutically acceptable salt thereof.

9. The compound of claim 1 wherein the compound is

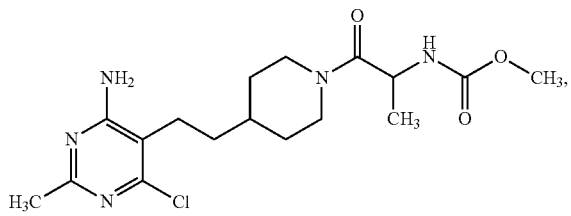 [SMILES: COC(=O)NC(C)C(=O)N1CCC(CCc2c(N)nc(C)nc2Cl)CC1]

or a pharmaceutically acceptable salt thereof.

10. The compound of claim 9 wherein the compound is

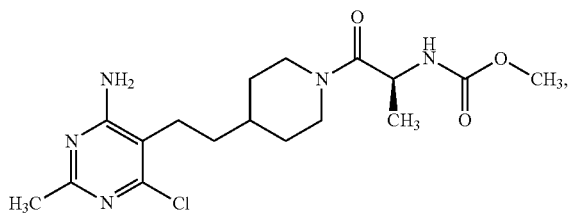 [SMILES: COC(=O)N[C@@H](C)C(=O)N1CCC(CCc2c(N)nc(C)nc2Cl)CC1]

or a pharmaceutically acceptable salt thereof.

11. The compound of claim 1 wherein the compound is

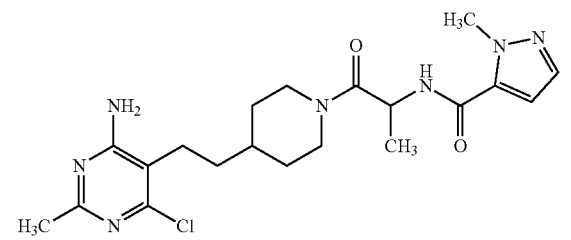 [SMILES: Cc1nc(N)c(CCC2CCN(C(=O)C(C)NC(=O)c3ccnn3C)CC2)c(Cl)n1]

or a pharmaceutically acceptable salt thereof.

12. The compound of claim 11 wherein the compound is

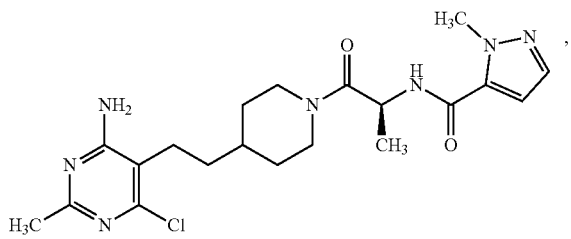 [SMILES: Cc1nc(N)c(CCC2CCN(C(=O)[C@H](C)NC(=O)c3ccnn3C)CC2)c(Cl)n1]

or a pharmaceutically acceptable salt thereof.

13. The compound of claim 1 wherein the compound is

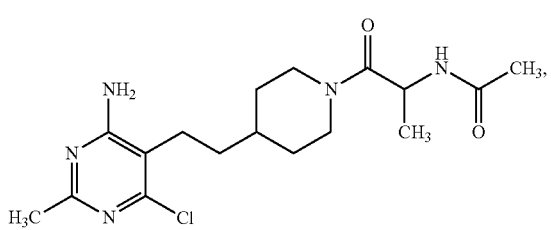 [SMILES: CC(=O)NC(C)C(=O)N1CCC(CCc2c(N)nc(C)nc2Cl)CC1]

or a pharmaceutically acceptable salt thereof.

14. The compound of claim 13 wherein the compound is

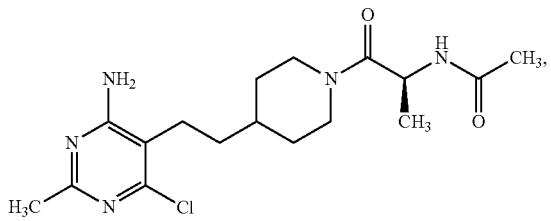 [SMILES: CC(=O)N[C@@H](C)C(=O)N1CCC(CCc2c(N)nc(C)nc2Cl)CC1]

or a pharmaceutically acceptable salt thereof.

15. A pharmaceutical composition comprising a compound of claim 1, or a pharmaceutically acceptable salt thereof, with one or more pharmaceutically acceptable carriers, diluents, or excipients.

16. The pharmaceutical composition according to claim 15 in combination with one or more other therapeutic agents.

17. A method of reducing weight gain comprising administering a compound according to claim 1, or a pharmaceutically acceptable salt thereof, to a patient in need thereof.

18. A method of reducing weight regain comprising administering a compound according to claim 1, or a pharmaceutically acceptable salt thereof, to a patient in need thereof.

19. A method of treating obesity comprising administering a compound according to claim 1, or a pharmaceutically acceptable salt thereof, to a patient in need thereof.

20. A method of treating type 2 diabetes comprising administering a compound according to claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 10,227,310 B2
APPLICATION NO. : 15/561163
DATED : March 12, 2019
INVENTOR(S) : Christopher Stanley Galka et al.

It is certified that error appears in the above-identified patent and that said Letters Patent is hereby corrected as shown below:

On the Title Page

Column 1 Line 1 (Title): Delete "0-ACYL" and insert -- O- ACYL --, therefor.

In the Specification

Column 1 Line 1: Delete "0- ACYL" and insert -- O- ACYL --, therefor.

In the Claims

Column 68 Line 66: In Claim 1, delete "CH$_3$ and Cl," and insert -- --CH$_3$ and –Cl, --, therefor.

Column 70 Lines 38-50:

In Claim 7, delete " 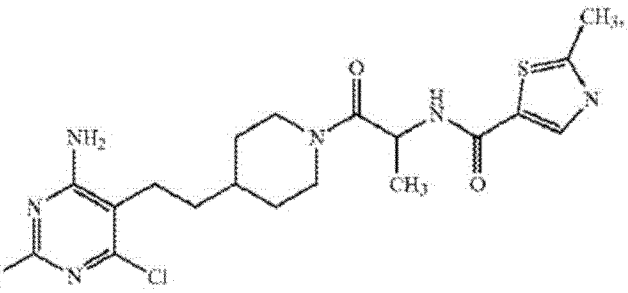 " and insert -- 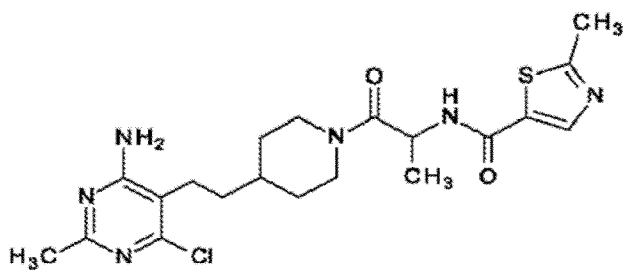 --, therefor.

Signed and Sealed this
Second Day of July, 2019

Andrei Iancu
*Director of the United States Patent and Trademark Office*

CERTIFICATE OF CORRECTION (continued)
U.S. Pat. No. 10,227,310 B2

In Claim 8, delete " 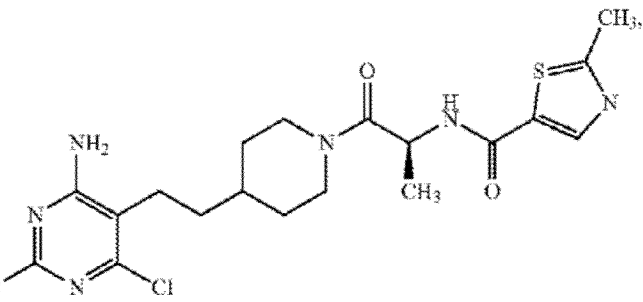 " and insert -- 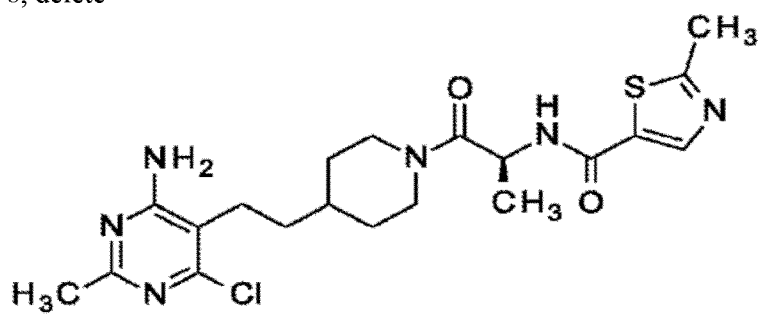 --, therefor.

In Claim 9, delete " 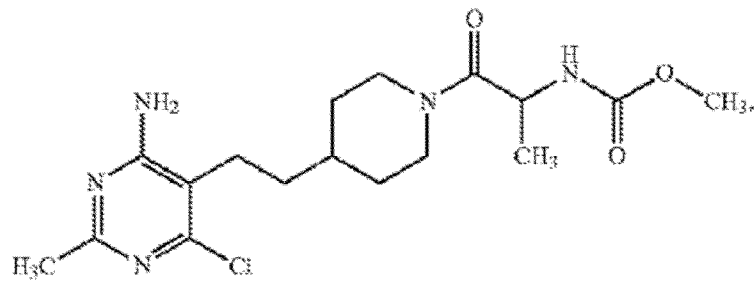 " and insert -- 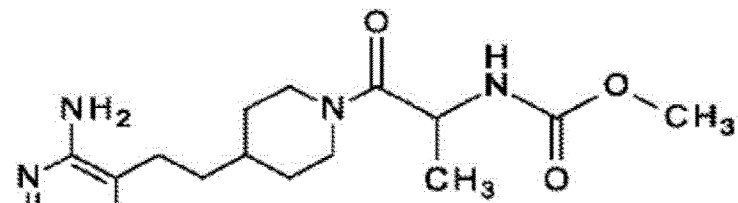 --, therefor.